United States Patent [19]

Saucy

[11] B  3,989,724
[45] Nov. 2, 1976

[54] TETRAHYDROPYRAN-2-OLS
[75] Inventor: Gabriel Saucy, Essex Fells, N.J.
[73] Assignee: Hoffmann-La Roche Inc., Nutley, N.J.
[22] Filed: Mar. 13, 1974
[21] Appl. No.: 450,708
[44] Published under the second Trial Voluntary Protest Program on March 9, 1976 as document No. B 450,708.

Related U.S. Application Data

[60] Division of Ser. No. 57,372, July 22, 1970, Pat. No. 3,816,458, which is a continuation-in-part of Ser. No. 679,989, Nov. 2, 1967, Pat. No. 3,544,598, which is a continuation-in-part of Ser. No. 633,730, April 26, 1967, abandoned, which is a continuation-in-part of Ser. No. 604,124, Dec. 23, 1966, abandoned, which is a continuation-in-part of Ser. No. 549,816, May 13, 1966, abandoned, which is a continuation-in-part of Ser. No. 813,693, April 4, 1969, abandoned.

[52] U.S. Cl. .......................... 260/345.9; 260/244 R; 260/307 FA; 260/327 M; 260/338; 260/340.7; 260/340.9; 260/345.8
[51] Int. Cl.² .................................... C07D 315/00
[58] Field of Search.......... 260/584 A, 340.7, 340.9, 260/327 M, 345.8, 345.9

[56] References Cited

UNITED STATES PATENTS

| | | | |
|---|---|---|---|
| 3,631,039 | 12/1971 | Andrews et al. | 260/584 A X |
| 3,655,695 | 4/1972 | Andrews et al. | 260/345.9 X |
| 3,813,417 | 5/1974 | Cohen et al. | 260/345.9 X |

Primary Examiner—Richard L. Raymond
Attorney, Agent, or Firm—Samuel L. Welt; George M. Gould

[57] ABSTRACT

Stereo-specific total synthesis of steroidal materials. 7-Substituted 3-oxo-1-heptenes or variants thereof are reacted with 2-alkylcycloalkane-1,3-diones yielding 3-substituted 6a β-alkyl-cyclopenta [f] [1] benzopyrans or naphtho [2,1-b] pyrans. These are then subjected to a selective catalytic hydrogenation followed by an introduction of a hydroxy, alkoxy or acyloxy group at the 4a-position to produce a 3-substituted 6a β,4a-hydroxy, alkoxy or acyloxy perhydrocyclopenta [f] [1] benzopyran or perhydro-naphtho [2,1-b] pyran. These latter compounds are then converted into 4- or 5-(3-oxoalkyl)perhydroindene-5-ones or perhydronaphthalene-6-ones which in turn can be converted to known steroidal materials by known methods.

8 Claims, No Drawings

TETRAHYDROPYRAN-2-OLS

Related Applications

This application is a divisional of applicants' co-pending application Ser. No. 57,372, filed July 22, 1970 now U.S. Pat. No. 3,816,458 which is a continuation-in-part of applicants' co-pending application Ser. No. 679,989, filed Nov. 2, 1967 U.S. Pat. No. 3,544,598, which is a continuation-in-part of applicants' co-pending application Ser. No. 633,730, filed Apr. 26, 1967 now abandoned, which was filed as a continuation-in-part of applicants' co-pending application Ser. No. 604,124, filed Dec. 23, 1966 now abandoned, which was filed as a continuation-in-part of applicants' co-pending application Ser. No. 549,816, filed May 13, 1966 now abandoned. This application is also a continuation-in-part of co-pending application Ser. No. 813,693, filed Apr. 4, 1969 now abandoned, inventors Gabriel Saucy and Michael Rosenberger, entitled, Preparation of 3-Oxo-19-nor-$\Delta^4$-Steroids from 10-[3-substituted alkyl]-desA Steroids.

BACKGROUND OF THE INVENTION

Cyclopenta[f][1]-benzopyrans and 7H-naphtho[2,1-b]pyrans are valuable as intermediates in the total synthesis of steroids. Total syntheses utilizing these compounds as intermediates are described in U.S. Pat. applications of Gabriel Saucy: Serial No. 549,816, filed Dec. 23, 1966 now abandoned; Ser. No. 604,124 filed May 13, 1966 now abandoned; Ser. No. 633,730, filed Apr. 26, 1967 now abandoned. Other related applications include Ser. No. 633,693, filed Apr. 26, 1967 now abandoned.

DETAILED DESCRIPTION OF THE INVENTION

This invention is concerned with certain polycyclic compounds and with processes for their synthesis. More particularly, this invention relates to novel cyclopenta[f][1]-benzopyrans and 7H-naphtho[2,1-b]pyrans, and to methods for their production. These compounds are useful as intermediates in syntheses of steroids and D-homosteroids, respectively. In synthesis of steroidal materials steric considerations are of great significance. The most used steroidal compounds are those having a C/D-trans ring junction with the substituent in the 13-position being in the β-stereoconfiguration. The present invention provides a facile total synthesis of 13β-C/D-trans-steroidal materials. This desirable result is obtained via a unique asymmetric induction with optical specificity preserved in subsequent reaction steps.

In a major aspect, this invention is concerned with novel cyclopenta[f][1]benzopyrans having the tricyclic nucleus

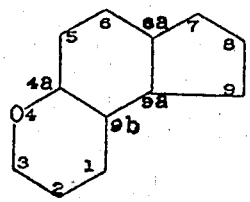

and novel naphtho[2,1-b]pyrans having the tricyclic nucleus

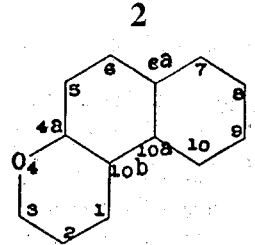

These novel compounds are generally defined by the formula

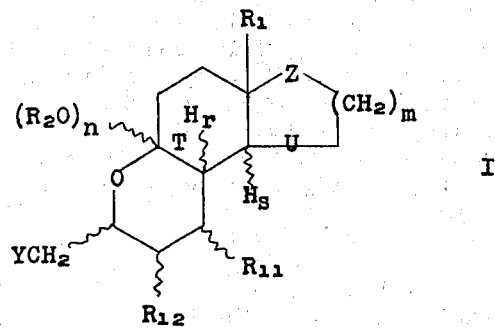

I wherein Y is hydrogen; an alkyl group of from 1 to 6 carbons; or a group of the formula $R_5CH_2C(R_3,R_4)CH(R_{14}) CH(R_{15})-$ wherein $R_3$, when taken alone, is hydroxy or a conventional hydrolyzable ether or ester group convertible to a hydroxy group by hydrolysis, $R_4$, when taken alone is hydrogen, and $R_3$ $R_4$, when taken together, are oxo or a conventional hydrolyzable ketal group convertible to an oxo moiety by hydrolysis; $R_1$ is a primary alkyl group of from 1 to 5 carbon atoms; $R_2$ is hydrogen, lower primary alkyl, or lower acyl;

$R_5$, $R_{11}$, $R_{12}$, $R_{14}$ and $R_{15}$ are each independently hydrogen or lower alkyl; Z is carbonyl or a group of the formula

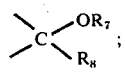

$R_7$ is hydrogen or lower acyl; $R_8$ is hydrogen or lower aliphatic hydrocarbyl; T represents either a single or a double bond; U represents a single or a double bond and is a single bond when T is a single bond; m is an integer having a value of from 1 to 2; n is an integer having a value of from 0 to 1 and is 0 when T represents a double bond and is 1 when T represents a single bond; r is an integer having a value of from 0 to 1 and is 0 when T is a double bond and 1 when T is a single bond; and s is an integer having a value of from 0 to 1 and is 0 when U is a double bond and 1 when U is a single bond.

As used throughout the specification and appended claims, the term "hydrocarbyl group" denotes a monovalent substituent consisting solely of carbon and hydrogen and having from 1 to 20 carbon atoms; the term "hydrocarbylene" denotes a divalent substituent consisting solely of carbon and hydrogen containing 1 to 20 carbon atoms and having its valence bonds from different carbons; the term "aliphatic" with reference to hydrocarbyl or hydrocarbylene groups, denotes groups containing no aromatic unsaturation, but which can be otherwise saturated or unsaturated, i.e., an alkyl or alkylene, or an aliphatic group containing olephinic or acetylenic unsaturation; the term "alkyl group" denotes a saturated hydrocarbyl group, whether straight or branched chain having 1 to 20 carbon atoms; the term "primary alkyl group" denotes an alkyl group having its valence bond from a carbon bonded to at least two hydrogens; the term "acyl group" denotes a group consisting of the residue of a hydrocarbyl monocarboxylic acid having 1 to 18 carbon atoms formed by removal of the hydroxyl portion of the carboxyl group; the term "oxyhydrocarbyl" denotes a monovalent saturated cyclic or acyclic group consisting of carbon, hydrogen, and oxygen containing only one oxygen in the form of an ether linkage; and the term "lower", as applied to any of the foregoing groups, denotes a group having a carbon skeleton containing up to and including eight carbons, such as methyl, ethyl, butyl, tert.-butyl, hexyl, 2-ethylhexyl, vinyl, butenyl, hexenyl, ethynyl, ethylene, methylene, formyl, acetyl, 2-phenylethyl, benzoyl, methoxymethyl, 1-methoxyethyl, and the like. The phraseology "conventional hydrolyzable ether or ester group convertible to a hydroxy group by hydrolysis" is meant to include ether groups such as lower alkoxy groups, e.g., methoxy, ethoxy, propoxy, t-butoxy (most preferable) and the like and lower oxyhydrocarbyloxy groups such as tetrahydropyran-2-yl-oxy, methoxymethyl-oxy, 1-methoxyethyl-oxy and the like; and ester groups such as acyl groups, e.g., formyloxy, acetyloxy, propionyloxy, pivaloyloxy, undecenoyloxy, benzoyloxy and the like. The phraseology "conventional hydrolyzable ketal group convertible to an oxo moiety by hydrolysis" comprehends moieties of the formula —OR$_9$O—, —OR$_9$S—, —OR$_9$N— or —SR$_9$S— wherein R$_9$ is alkylene having from 1 to 4 carbon atoms. Exemplary moieties are 1,2-ethylenedioxy, 2,2-dimethyl-1,3-propylenedioxy, 1,2-ethylenedimercapto, 2,3-butylenedioxy and the like.

In the formulas presented herein, the various substituents on cyclic compounds are joined to the cyclic nucleus by one of three notations, a solid line (——) indicating a substituent which is in the β-orientation (i.e., above the plane of the paper), a dotted line (······) indicating a substituent which is in the α-orientation (below the plane of the paper), or a wavy line (∼∼∼) indicating a substituent which may be either the α- or β-orientation. The position of R$_1$ has been arbitrarily indicated as the β-orientation, although the products obtained in the examples are all racemic compounds unless otherwise specified.

Preferred compounds are those wherein Y is n-alkyl, especially methyl, 3,3-(alkylenedioxy)butyl wherein the alkylenedioxy group, when taken with the 3-carbon of the butyl radical; forms a dioxolane ring system, especially 3,3-(ethylenedioxy)-butyl and 3,3-(2',3'-butylenedioxy)-butyl; 3-hydroxybutyl, 3-tert.alkoxybutyl, especially 3-tert.-butoxybutyl, or 3-(tetrahydropyran-2-yloxy)butyl; R$_1$ is n-alkyl, especially methyl and ethyl; and, when $s$ has a value of 1, the 9a- (when $m$ is 1) or 10a-(when $m$ is 2) hydrogen is trans-oriented with respect to R$_1$.

Subgeneric to the tricyclic compounds of formula I are the 3-substituted-6aβ-alkyl-1,2,3,5,6,6a,7,8-octahydrocyclopenta[f][1]benzopyrans and the 3-substituted-6aβ-alkyl-1,2,5,6,6a,7,8,9-octahydro-3H-naphtho[2,1-b]pyrans (by alternate nomenclature 3-substituted-6aβ-alkyl-1,2,3,5,6,6a,8,9-octahydro-7H-naphtho[2,1-b]pyrans), hereinafter referred to as "dienes", having the formula:

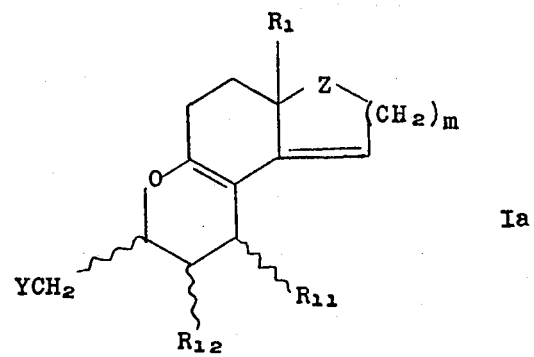

Ia wherein R$_1$, R$_{11}$, R$_{12}$, Z, Y and $m$ are as defined above; the 3-substituted-6aβ-alkyl-1,2,3,5,6,6a,7,8,9,9a-decahydrocyclopenta[f][1]benzopyrans and the 3-substituted-6aβ-alkyl-1,2,5,6,6a,7,8,9,10,10a-decahydro-3H-naphtho[2,1-b]pyrans), hereinafter referred to as "monoenes", represented by the formula:

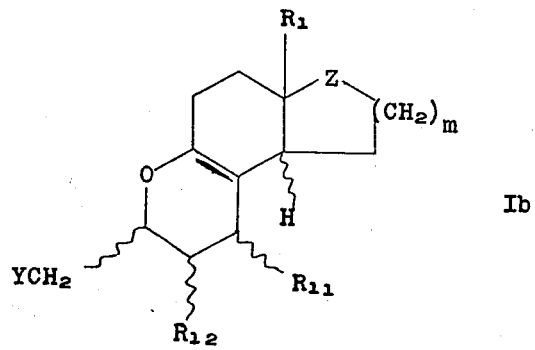

Ib wherein $R_1$, $R_{11}$, $R_{12}$, Z, Y, and m are as defined above; and the 3-substituted-6a$\beta$-alkyl-4a-hydroxyperhydrocyclopenta[f][1]benzopyrans and the 3-substituted-6a$\beta$-alkyl-4a-hydroxyperhydronaphtho[2,1-b]pyrans and their lower alkyl ethers and monoacyl esters, hereinafter referred to as "perhydro" compounds, represented by the formula:

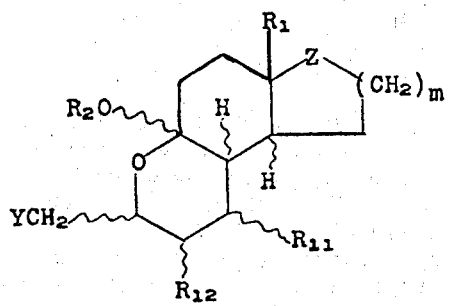

Ic wherein $R_1$, $R_2$, $R_{11}$, $R_{12}$, Z, Y, and m are defined as above.

Alternatively, the tricyclic compounds of formula I can be classified according to the nature of Y, which determines the utility of the compounds of this invention. The first of these classes are the 3-alkyl compounds of the formula:

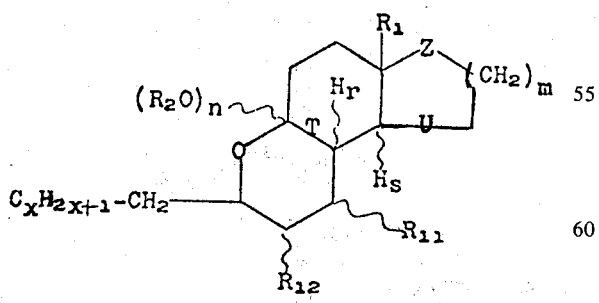

Id wherein $R_1$, $R_2$, $R_{11}$, $R_{12}$, Z, m, n, r, s, T, and U are as defined above and x is an integer having a value of from 0 to 6, inclusive.

These products are useful as intermediates for the synthesis of members of a recently discovered class of 9$\beta$, 10$\alpha$- or retro- steroids, and also are useful as intermediates for the synthesis of 10$\alpha$-steroids, and other steroidal materials.

The second class of intermediates classified according to utility are the 3-(4-substituted pentyl) compounds of the formula:

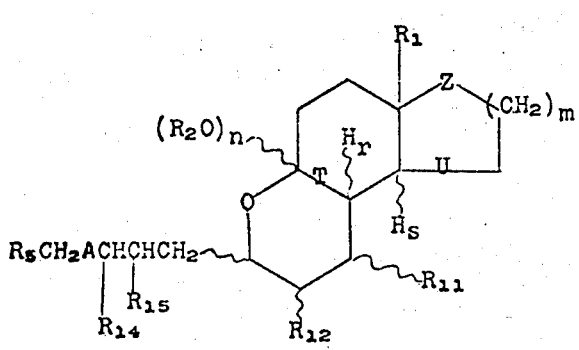

Ie wherein $R_1$, $R_2$, $R_5$, $R_{11}$, $R_{12}$, $R_{14}$, $R_{15}$, Z, m, n, r, s, T, and U are as defined above; A is carbonyl or —$CR_3R_4$—; and $R_3$ and $R_4$ are as defined above.

These compounds, which are useful as intermediates for the synthesis of 19-nor-steroids of the normal series, and other steroidal materials, can be further classified as:

1. The 3-(4-oxopentyl)-substituted cyclopentabenzopyrans and naphthopyrans of the formula:

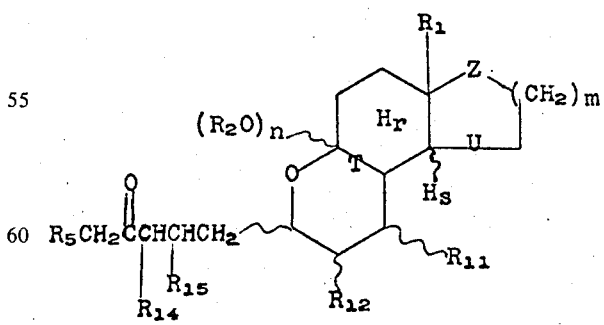

Ie-1 wherein $R_1$, $R_2$, $R_5$, $R_{11}$, $R_{12}$, $R_{14}$, $R_{15}$, $Z$, $m$, $n$, $r$, $s$, $T$, and $U$ are as defined above.

2. The 3-[4,4-(ketal)pentyl]-substituted cyclopentabenzopyrans and naphthopyrans of the formula:

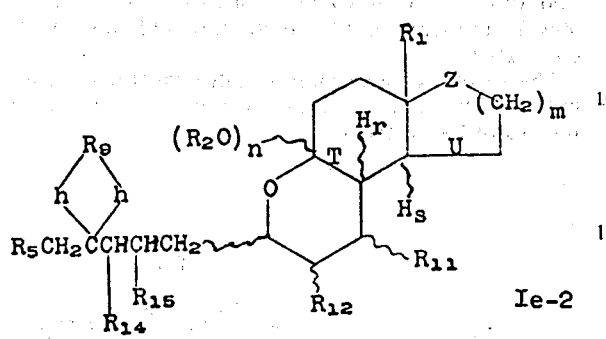

Ie-2 wherein $R_1$, $R_2$, $R_5$, $R_9$, $R_{11}$, $R_{12}$, $R_{14}$, $R_{15}$, $Z$, $m$, $n$, $r$, $s$, $T$, and $U$ are as defined above; and both $h$ are either sulfur or oxygen, or one $h$ is oxygen and the other is sulfur or nitrogen.

and

3. The 3-(4-hydroxypentyl)-substituted cyclopentabenzopyrans and naphthopyrans and ethers thereof of the formula:

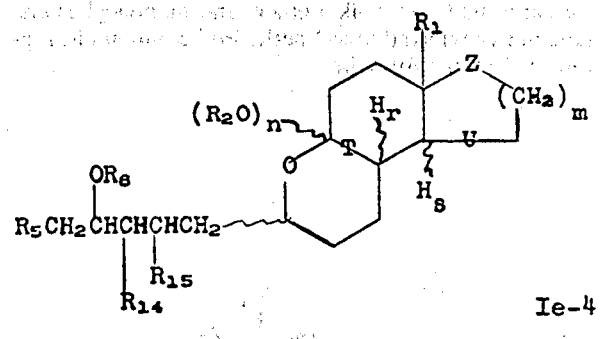

Ie-4 wherein $R_1$, $R_2$, $R_5$, $R_{11}$, $R_{12}$, $R_{14}$, $R_{15}$, $Z$, $m$, $n$, $r$, $s$, $T$, and $U$ are as defined above and $R_6$ is hydrogen, lower alkyl, lower acyl or lower oxyhydrocarbyl.

In compounds of formula Ie-4, $R_6$ as t-butyl is especially preferred.

In a second aspect, this invention is concerned with a method for producing the compounds of formula I via the following general reaction scheme:

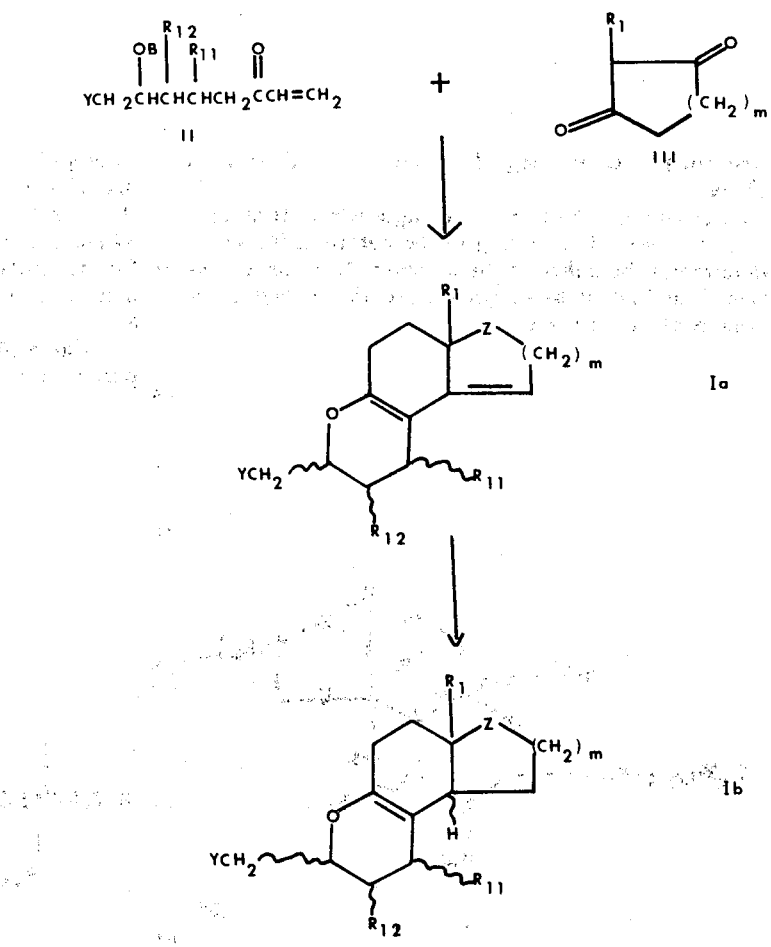

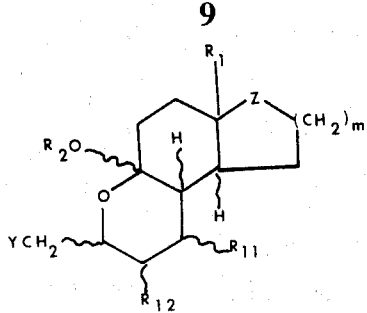

wherein Y, $R_1$, $R_2$, $R_{11}$, $R_{12}$, Z, and $m$ are as defined above; and B is hydrogen, lower alkyl or lower acyl.

Thus, the process of this invention comprises the general steps of (1) condensation of a 7-hydroxy-1-alken-3-one or a variant thereof (II), as defined below, with a 2-alkylcycloalkane-1,3-dione (III), as defined below, to produce diene (Ia); (2) saturation of the 9,9a- or 10,10a-double bond of diene (Ia) to produce monoene (Ib); and (3) introduction of a hydroxy, alkoxy, or acyloxy group at the 4a-position and a hydrogen atom at the 9b- or 10b-position of monoene (Ib) to produce perhydro compound (Ic). It is to be understood that the foregoing reaction sequence is merely schematic in nature, and that each depicted step can represent only one or more than one reaction, as will be more fully described herein.

It will be noted that the diene, monoene and perhydro compounds of this invention can bear a 3-(4-oxopentyl)-substituent. When such a side chain is desired, it is however preferable to perform the reaction sequence with compounds having the oxo moiety of the 4-oxopentyl side chain in protected form. Protection can be effected by ketalization (to form lower alkylenedioxy or other hetero variants thereof), or by reduction to a hydroxy moiety optionally followed by etherification or esterification. The oxo moiety can be regenerated at any intermediate stage as desired. 1-Alken-3-one compounds of formula II are employed as one of the starting materials for the foregoing reaction sequence. Illustrative examples of these 1-alken-3-ones include 7-hydroxy-1-octen-3-one, 7-hydroxy-1-nonen-3-one, 7-hydroxy-1-dodecen-3-one, 7-acetoxy-1-nonen-3-one, 7-benzoyloxy-1-nonen-3-one, 7-methoxy-1-nonen-3-one, 7-benzyloxy-1-nonen-3-one, 11,11-ethylenedioxy-7-hydroxy-1-dodecen-3-one, 7,11-dihydroxy-1-dodecen-3-one, 11-tert.-butoxy-7-hydroxy-1-dodecen-3-one, 11-(tetrahydropyran-2-yloxy)-7-hydroxy-1-dodecen-3-one, and the like.

The 7-hydroxyalken-3-ones of formula II above are readily synthesized from (A) a glutaric acid anhydride, (B) a 2-alkylcyclohexane-1,3-dione, (C) a glutaraldehyde or (D) a butyrolactone, as is illustrated by the following sequences leading to 7-hydroxynonen-3-ones:

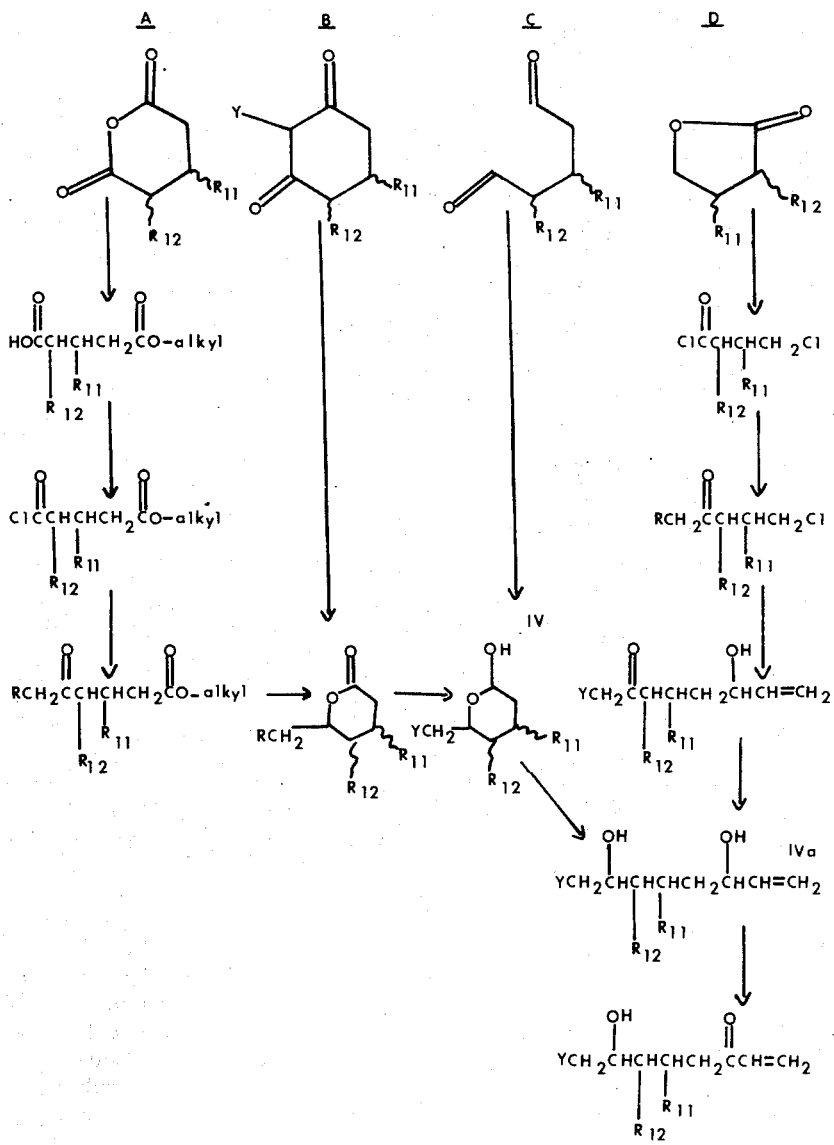

In sequence A, a six-membered ring cyclic anhydride such as glutaric anhydride is reacted with a lower alkanol, for example, ethanol, to produce a monoalkyl glutarate half-ester. This half-ester is reacted with thionyl chloride to produce the corresponding acid chloride, which in turn is reacted with a dialkyl cadmium compound [$(RCH_2)_2Cd$] to produce a 5-alkyl-substituted 5-oxopentanoate. This ketone is then hydrogenated in the presence of a noble metal catalyst to form 5-substituted-5-valerolactone. The lactone is reduced by reaction with diisopropylaluminum hydride to form 6-substituted-tetrahydropyran-2-ol. The tetrahydropyranol is then reacted with vinyl magnesium bromide or chloride to form 7-substituted-1-heptene-3,7-diol which, on reaction with manganese dioxide, is converted to 7-substituted-7-hydroxy-1-hepten-3-one.

Sequence B comprises preparing the 5-alkyl-substituted-5-valerolactone employed in sequence A from 2-substituted-cyclohexane-1,3-dione. This transformation can be effected, for example, by hydrogenating the cyclohexanedione in the presence of sodium hydroxide and a Raney nickel catalyst to produce sodium 5-hydroxyvalerate, followed by acidification with, for example, hydrochloric acid. Alternatively, the cyclohexanedione can be reacted with barium hydroxide to produce 5-substituted-5-oxopentanoic acid which, on hydrogenation in the presence of sodium hydroxide and Raney nickel followed by acidification, yields 5-substituted-5-valerolactone.

Sequence C involves reacting a 1,5-alkylenedial such as glutaraldehyde with a Grignard reagent of the formula $$YCH_2MgX$$

wherein Y is as defined above and X is bromine or chlorine to form a 6-substituted-tetrahydropyran-2-ol. This reaction and the products obtained thereby are described in greater detail in United States patent application of David A. Andrews and Gabriel Saucy, Ser. No. 633,693, filed Apr. 26, 1967 now abandoned, entitled "6-SUBSTITUTED TETRAHYDROPYRAN-2-OLS AND PROCESS FOR THEIR PRODUCTION".

Sequence D comprises reacting, for example, butyrolactone with thionyl chloride in the presence of zinc chloride to produce a 4-chlorobutyric acid chloride. The acid chloride is reacted with the dialkyl compound [$(RCH_2)_2Cd$] as defined above to produce 5-substituted-1-chloropentan-4-one. The chloroketone, in the form of its ketal, for example, the ethylenedioxy ketal, is reacted with magnesium to form 4-(ethylenedioxy)-5-substituted pentyl magnesium chloride. This Grignard reagent is reacted with acrolein to yield, upon hydrolysis, 8-substituted-3-hydroxyocten-7-one. This hydroxy ketone is reduced to 7-substituted-1-heptene-3,7-diol by reaction with lithium aluminum hydride, and the diol converted to 7-substituted-7-hydroxyhepten-3-one by reaction with manganese dioxide.

Because of the susceptibility of the vinyl group of the 7-hydroxy-1-alken-3-one to oxidation, it is desirable, although not essential, that this compound be converted to more stable variants, such as those of the formula:

$$YCH_2\underset{\underset{R_{12}}{|}}{\overset{\overset{OB}{|}}{C}H}\underset{\underset{R_{11}}{|}}{C}HCHCH_2\overset{O}{\overset{||}{C}}-(-CH_2)_{\overline{2}}-R_{16} \qquad IIa$$

wherein $R_{11}$, $R_{12}$, Y and B are as defined above; and $R_{16}$ is chloro, hydroxy, lower alkoxy, lower hydrocarbylamino or di(lower hydrocarbyl)amino.

Variants of formula IIa and methods for their preparation are described in detail in my United States Pat. application Ser. No. 604,124, filed Dec. 23, 1966 now abandoned, entitled "α-OLEFINS".

As exemplary, these compounds of formula IIa are readily produced from the vinyl ketones of formula II by known techniques. For example, 1-chloro-7-hydroxyalkan-3-ones are obtained by the anti-Markownikoff reaction of the vinyl compound with hydrogen chloride in known manner. 1-Hydroxy and 1-alkoxy derivatives are obtained by the base-catalyzed reaction of water or a lower alkanol, for example, methanol, with the vinyl ketone. Additional derivatives are formed by the reaction of the vinyl ketone with a mono(lower hydrocarbyl)- or di(lower hydrocarbyl)-amine to form the Mannich base 1-(lower hydrocarbyl)amino- or 1-di(lower hydrocarbyl)amino-7-hydroxyalkan-3-one. A particularly advantageous procedure is to oxidize a hydroxy vinyl compound of formula IVa with manganese dioxide in the presence of such an amine. In some instances, particularly in large scale commercial operation, it may be desirable to convert the Mannich base to its crystalline acid addition salts, particularly quaternary ammonium salts. All of the chloro, hydroxy, alkoxy, and aminoalkanones yield the alkenones of formula II under the conditions of the condensation with the 2-alkylcycloalkane-1,3-dione.

The compounds of formula II can be used in the form of still another variant. This is the cyclized variant comprising a cyclic hemiketal, i.e., 2-tetrahydropyranol of the formula:

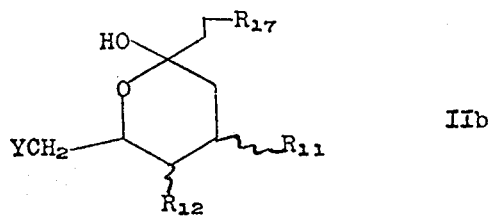

IIb wherein Y is as defined above and $R_{17}$ is lower hydrocarbylamino or di(lower hydrocarbyl)amino.

The variants of formula IIb can be prepared from compounds of formula II by reaction with the same reactants as are used to produce those compounds of formula IIa wherein $R_{18}$ is lower hydrocarbylamino or di(lower hydrocarbyl)amino. As is apparent, those compounds of formula IIa wherein $R_{16}$ has the aforesaid meanings and the compounds of formula IIb are isomers. These isomers exist in the form of a ketone of formula IIa or in the form of a cyclic hemiketal of formula IIb or as an equilibrium mixture of the two forms, Whether a particular Mannich base of formula IIa exists in that form or the hemiketal form or in an equilibrium mixture consisting primarily of one or the other will depend upon the environmental conditions in which it is placed, such as temperature, solvent and pH of reaction medium, as well as the particular meaning of Y and $R_{16}$ or $R_{17}$. Either form is useful for the purposes of this invention since these isomers are used in a reaction with compounds of formula III, infra, and either the acyclic form of formula IIa or the cyclic hemiketal form of formula IIb is useful for this purpose. A particular advantage of the cyclic form is its greater stability as compared with the acyclic form and also as compared with the vinyl ketones of formula II. In order to obtain the cyclic form it is essential that in the compound of formula IIa, B is hydrogen. Acidic conditions shift the equilibrium away from the cyclic form. Use of an optically active amine, e.g., phenylethylamine, offers the advantage of resolving the compound, for example, via salt formation, to give an optically pure isomer of formula IIa or IIb which is then used in the remainder of the reaction sequence of this invention and when coupled with the unique asymmetric induction and preservation of optical specificity thereof offers a facile route to optically pure steroidal materials.

In a further aspect of this invention optically active compounds of formula IIb where Y is 3-oxobutyl are prepared from optically active precursors according to the following reaction sequence:

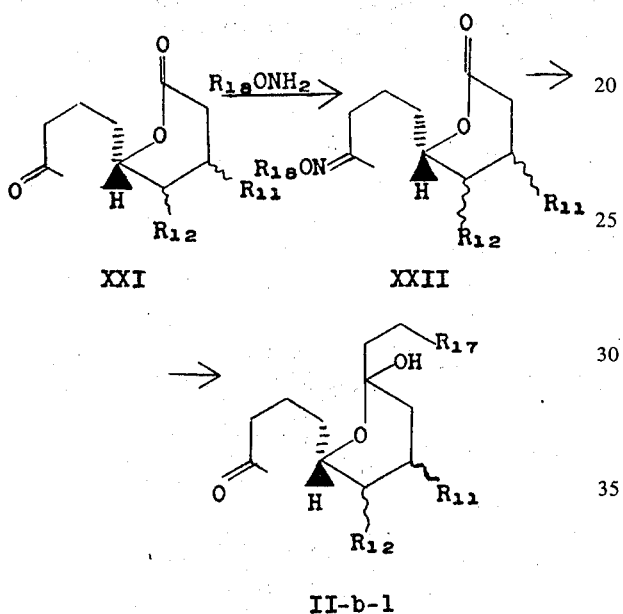

where $R_{18}$ is lower alkyl; and $R_{11}$, $R_{12}$ and $R_{17}$ are as above.

As indicated an optically active 9-oxo-decanoic acid δ-lactone of formula XXI is treated with a lower alkoxy amine or an acid addition salt thereof, e.g., a mineral acid salt such as the hydrochloride, hydrogen sulfate, hydrobromide and the like to form the corresponding lower alkoxy, imino compound XXII. A preferred lower alkoxyamine for this purpose is methoxyamine, most preferably in the form of its hydrochloride salt. This reaction is conducted at a temperature in the range of from about −10° to 50°C., most preferably in the range of from about 25° to 30°C. A solvent may be employed to facilitate the course of the reaction. Preferred solvents include organic nitrogen bases such as for example, pyridine, triethylamine, diemethylamine, trimethylamine and the like. After completion of the reaction wherein a mineral acid salt of the lower alkoxyamine is employed it is desirable to add a basic organic amine to the reaction mixture to neutralize the acid produced. Suitable basic organic amines for this purpose include the tertiary amines, e.g., trialkylamines such as triethylamine.

In the second step of this sequence the keto lactone XXII is treated first with vinyl Grignard, e.g., vinyl magnesium bromide or chloride in an ethereal solvent, e.g., tetrahydrofuran at a temperature in the range of from about 0° to −70°C; preferably in the range of from about −45° to −55°C. The resulting intermediate having the following tautomeric structure

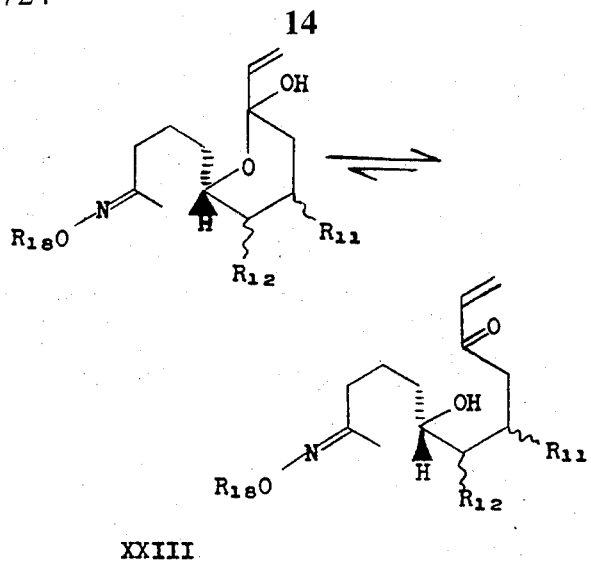

XXIII where $R_{11}$, $R_{12}$ and $R_{18}$ are as above
is then treated with a lower hydrocarbylamine or a di(lower hydrocarbyl)amine, e.g., diethylamine in an etheral solvent, e.g., diethyl ether at a temperature in the range of from about 0° to 50°C., preferably at about room temperature to yield an intermediate of the formula

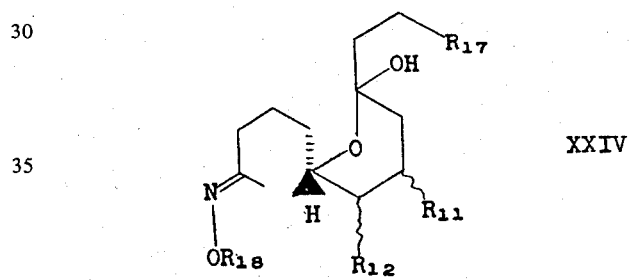

where $R_{11}$, $R_{12}$, $R_{17}$ and $R_{18}$ are as above.

The intermediate oxime compound XXIV when treated with dilute aqueous acid, such as aqueous mineral acid, e.g., 2N sulfuric acid is hydrolyzed to the ketone with concomitant purification of the amine to yield the desired compound of formula II-b-1. This acid treatment step is conveniently carried out in the presence of a suitable inert organic solvent, preferably a ketonic solvent such as acetone, at a temperature in the range of from about 0° to 50°C., preferably in the range of from about 20° to 30°C., e.g., 25°C.

It should be noted that intermediate compounds XXIII and XXIV need not be isolated or otherwise purified during the aforementioned transformations but can be utilized in crude form for further steps.

The optically active 9-oxo-decanoic acid δ-lactone of the indicated configuration may be prepared from racemic 5,9-dioxodecanoic acid by microbiological reduction followed by lactonization. This procedure, which is not part of the present invention, is described in detail in U.S. Pat. Application Ser. No. 57,371, now U.S. Pat. No. 3,657,070, "MICROBIOLOGICAL PREPARATION OF OPTICALLY ACTIVE 9-OXO-5(S)-HYDROXY-DECANOIC ACID AND THE LACTONE Thereof," inventors Julius Berger and Michael Rosenberger.

As is indicated above, the 7-hydroxy group of the 7-hydroxyalkanone of formula II or IIa can be esterified or etherified for the condensation reaction with the cycloalkanedione. These reactions can be effected in known manner. For example, the 7-hydroxyalkan-3-one can be reacted with a carboxylic acid or an acid chloride to produce an ester, or can be converted to an ether by either (1) preferably, known acid catalyzed etherifications, e.g., with isobutylene or dihydropyran or (2) conversion of the 7-hydroxyalken-3-one to its sodium salt followed by reaction of the salt with an alkyl halide. In the event $R_8$ is hydrogen, this hydroxyl group is also etherified or esterified.

The starting material of formula II or variant thereof can either be used in racemic form or in optically active form. When used in optically active form, the 7S-antipode is preferred for reasons more fully explained below.

The second reactant employed in the condensation as generally mentioned above is a 2-(lower alkyl)cycloalkane-1,3-dione of the formula:

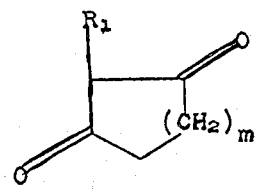

III wherein $R_1$ and m are as defined above.

These compounds are known compounds and description of their synthesis is accordingly unnecessary. Suitable compounds include 2-methylcyclopentane-1,3-dione, 2-ethylcyclopentane-1,3-dione, 2-propylcyclopentane-1,3-dione, 2-butylcyclopentane-1,3-dione, 2-methylcyclohexane-1,3-dione, and the like.

The conditions for the condensation of ketone (II) or variant (IIa, IIb or IIb-1) with cyclic dione (III) are not narrowly critical, although it is preferred, particularly when the acyclic ketone is charged as the vinyl ketone, that a non-oxidizing atmosphere, e.g., nitrogen or argon, be employed. It is further preferred that an antioxidant, for example, phenolic compounds such as hydroquinone, be present. Furthermore, the reaction can be conducted in the absence or presence of acid or base promoters. Suitable basic promoters include those heretofore known to promote the Michael condensation, including inorganic bases, for example, alkali metal hydroxides, such as sodium hydroxide or potassium hydroxide, and organic bases, including alkali metal alkoxides, for example, sodium or potassium methoxide or ethoxide, and ammonium hydroxides, particularly benzyltrialkylammonium hydroxide. A preferred class of base promoters are the amines, especially tertiary amines and most preferably pyridine-type compounds such as pyridine and the picolines. Acid promoters which can be employed include organic carboxylic acids such as acetic acid or benzoic acid; organic sulfonic acids such as p-toluenesolfonic acid; and mineral acids such as sulfuric acid, phosphoric acid, hydrochloric acid, and the like. The amount of promoter employed is not narrowly critical and can vary from catalytic amounts to molar amounts.

The ratio of ketone (II) or variant (IIa, IIb or II-b-1) to cyclic dione (III) is not narrowly critical, although approximately equimolar amounts are preferred. Although there is no particular advantage to the use of excesses of either reactant, the cycloalkanedione can be more readily employed in excess because, due to its general low solubility in known organic solvents, unreacted cycloalkanedione can be easily recovered from the reaction mixture.

The reaction temperature is not critical and can vary from room temperature or below to reflux temperature or higher. The condensation is preferably conducted in the presence of an inert solvent to insure a fluid reaction mixture and uniform reaction temperatures. Primary alcohols are not desirable due to their tendency to react with vinyl ketones. Suitable solvents include tertiary alcohols such as tert.-butanol, aliphatic and aromatic hydrocarbons such as cyclohexane, hexane, octane, benzene, xylene, toluene, and the like; ethers such as diethyl ether, tetrahydrofuran, and the like; chlorinated hydrocarbons such as carbon tetrachloride, chloroform, and the like; as well as dipolar aprotic solvents such as dimethylsulfoxide and the N,N-disubstituted amides such as dimethylformamide or dimethylacetamide.

The product of the condensation, depending upon the nature of vinyl ketone or variant (II, IIa, IIb or II-b-1) and/or the reaction promoter employed, can be one or more of the compounds having the formulae:

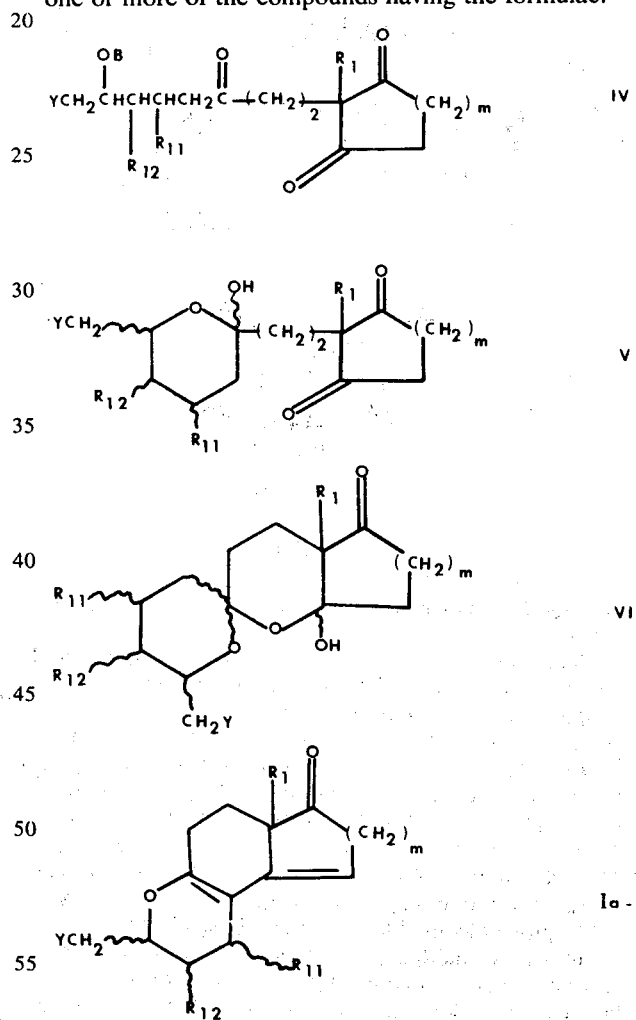

wherein $R_1$, $R_{11}$, $R_{12}$, B, Y, and m are as defined above.

When vinyl ketone (II) is a 7-alkoxy- or 7-acyloxy compound, the product will be a compound of formula IV. However, when the vinyl ketone is a 7-hydroxy compound, or the reaction conditions are sufficient to convert a 7-alkoxy- or 7-acyloxy group, if present, the product will depend upon the promoter.

When the promoter is an acid or a relatively weak base, such as pyridine, or when no promoter is employed at all, the reaction product obtained from the 7-hydroxy vinyl ketone is the diene, i.e., tricyclic enol ether (Ia-1). When a strong base, such as sodium or potassium hydroxide, is employed as a promoter, a crystalline product having the formula VI is isolated, although compounds of formulae IV and V are also present in the reaction mixture. However, the compounds of formulae IV, V and VI, upon treatment with an acid, such as acetic acid, para-toluenesulfonic acid, or sulfuric acid, readily form the diene, i.e., tricyclic enol ether (I$a$-1). It should also be noted that the conversion of the acyloxy or alkoxy groups of compound (IV) to a hydroxy group in an acidic medium is accompanied by cyclization to enol ether (I$a$-1).

The condensation of a vinyl ketone of formula II or a variant thereof of formula II$a$ or II$b$ with a cycloalkanedione of formula III is one of the key features of this reaction. It is in this condensation that specific stereochemical induction at one member of the critical C/D-ring junction of the eventual steroidal product occurs. Thus, this invention is particularly advantageous in that it involves a unique asymmetric induction. Thus, the products of the condensation, i.e., the dienones of formula I$a$-1, have at least two asymmetric centers at positions 3 and 6$a$ permitting theoretically of two racemates or four optical antipodes. However, as a result of the condensation of this invention, when using a racemic starting material of formulas II, II$a$ or II$b$ wherein $R_{11}$ and $R_{12}$ are both hydrogen only a single racemate of formula I$a$-1 results and when using an optically active starting material of formulas II, II$a$, II$b$ or II$b$-1 wherein $R_{11}$ and $R_{12}$ are both hydrogen only a single optical antipode of formula I$a$-1 results. It has further been found that when starting with a compound of formula II or II$a$ with a 7S-stereoconfiguration or of formula IIB with corresponding stereoconfiguration there is obtained the more desirable optical antipode of formula I$a$-1 having a 6a$\beta$-stereoconfiguration. Thus, to prepare steroidal materials having the more desired 13$\beta$-stereoconfiguration by the synthesis of this invention one can either start with the antipode of formula II, II$a$, II$b$ or II$b$-1, which can be prepared by resolving a racemic compound of formula II, II$a$ or II$b$, or one can resolve at some intermediate stage subsequent to the condensation with a cycloalkanedione of formula III or one can resolve the end-product steroidal material. In any event, the unique asymmetric induction concurrent to the condensation of this invention renders the obtention of a single optical antipode as an end-product more facile. The simultaneous formation of the dienol ether of formula I$a$-1 with unique asymmetric induction is a special advantage of this invention.

The dienes of formula I$a$ in the presence of water and acid, e.g., sulfuric acid in acetone, aqueous acetic acid or aqueous hydrochloric acid in dioxane, undergo acid hydrolysis to form indenones of the formula

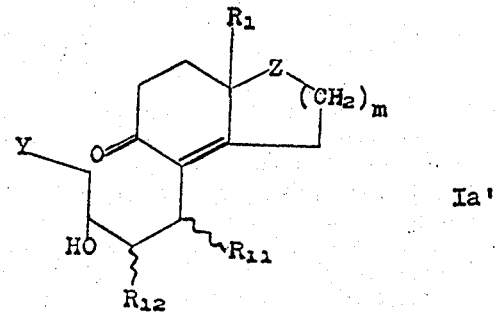

I$a'$ wherein $R_1$, $R_{11}$, $R_{12}$, Y and m have the same meaning as above.

The indenones of formula I$a'$ are themselves convertible to compounds of formula I$a$ via dehydration, for example, via acid catalyzed azeotropic distillation in benzene. Suitable acid catalysts are p-toluenesulfonic acid, potassium bisulfate, boron trifluoride etherate and the like. This reversible hydrolysis of compounds of formula I$a$ is useful in their preparation and purification. Thus, in instances where the direct purification of compounds of formula I$a$ is difficult it is often more facile to hydrolyze the compound of formula I$a$ to a compound of formula I$a'$, which can then be purified, for example, by chromatography, and subsequently be reconverted to the desired compound of formula I$a$ via dehydration.

The ketodienes of formula I$a$-1 are readily converted to the corresponding 7$\beta$-alcohols and their esters as represented by the formula:

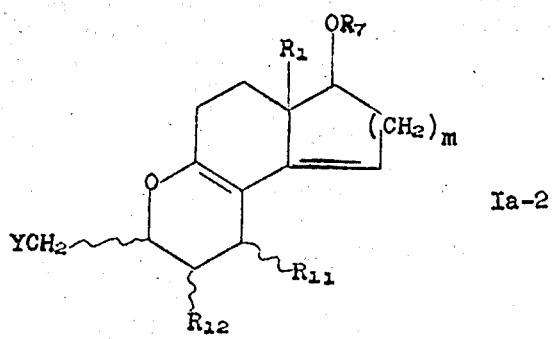

I$a$-2 wherein Y, $R_1$, $R_7$, $R_{11}$, $R_{12}$ and m are as previously defined,
by the sequence of reactions comprising reduction of the ketone to the alcohol and, if desired, subsequent esterification.

The reduction can be effected by any of the known methods for the chemical reduction of a ketone, e.g., by reaction of dienone (I$a$-1) with an alkali metal or Group III-metal reducing agent. By the term "alkali metal," as employed herein, is meant a Group I-metal having an atomic number of from 3 to 19, inclusive, i.e., lithium, sodium, and potassium. Group III-metals include those having atomic numbers of from 5 to 13, inclusive, i.e., boron and aluminum. Illustrative examples of these reducing agents include an alkali metal, preferably lithium or sodium, in liquid ammonia or a liquid aliphatic amine; tri(lower alkoxy)-aluminum compounds such as triisopropoxyaluminum; di(lower alkyl)-aluminum hydrides such as diethylaluminum hydride and diisobutyl-aluminum hydride; alkali metal-Group III-metal complex hydrides such as lithium aluminum hydride, sodium aluminum hydride, and sodium borohydride; tri(lower alkoxy)alkali metal-Group III-metal complex hydrides such as trimethoxy lithium aluminum hydride and tributoxy lithium aluminum hydride; diisobutyl aluminum hydride and the like. The alkali metal-Group III-metal complex hydrides are preferred as reducing agents, with the nonalkaline reagents, such as lithium aluminum hydride, being especially preferred.

This reaction is effected in any suitable inert reaction medium, such as hydrocarbons, e.g., cyclohexane, benzene, toluene, and xylene; ethers, e.g., diethyl ether, diisopropyl ether, and tetrahydrofuran. Protic solvents, such as water or alcohols, should not be employed when lithium aluminum hydride is the reducing agent, but can be employed with sodium borohydride.

The remaining reaction conditions are not narrowly critical, although it is generally preferred to effect the reduction at reduced temperatures, i.e., below about room temperature (about 20°–25°C.). Temperatures in the range of from about 0°C. to about room temperature are normally employed.

In the reduction of a dienone of formula Ia-1 to a dienol of formula Ia-2 any keto group in the side chain symbolized by Y is simultaneously reduced and any acyloxy group is hydrolyzed, in both cases yielding a corresponding hydroxy group. Any such side chain hydroxy group can be converted to an oxo moiety by treatment with conventional oxidizing means such as manganese dioxide. It is, however, preferable to use starting materials with etherified hydroxy moieties or ketalized oxo moieties in the side chain since these are unaffected by the reduction.

The free alcohol is recovered from the reaction mixture after treatment of the mixture with acid. The alcohol can be esterified in known manner, for example, by base-catalyzed reaction with a carboxylic acid halide or carboxylic acid anhydride. Illustrative bases include inorganic bases such as sodium hydroxide and potassium hydroxide and organic bases such as a sodium alkoxide or an amine, especially a tertiary amine, and more particularly, pyridine and the picolines.

The ketodienes of formula Ia-1 can also be converted to their $7\beta$-hydroxy-$7\alpha$-hydrocarbyl derivatives represented by the formula:

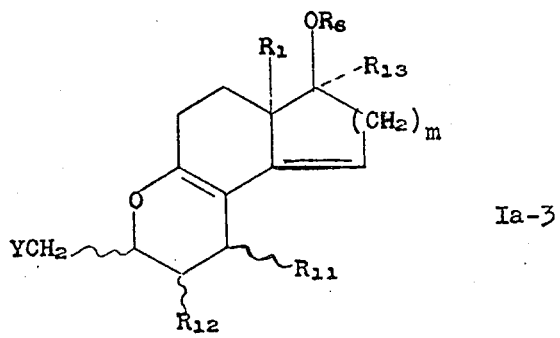

Ia-3 wherein Y, $R_1$, $R_8$, $R_{11}$, $R_{12}$ and $m$ are as previously defined and $R_{13}$ is lower hydrocarbyl by reaction of the ketodiene with a Grignard reagent of the formula:

    VII $R_{13}MgX$ wherein $R_{13}$ is as previously defined and X is a halogen having an atomic number of from 17 to 35, inclusive (i.e., chlorine or bromine).

This Grignard reaction is conducted in known manner. For example, the Grignard reagent is prepared by reacting a hydrocarbyl halide with magnesium in an ether reaction medium, for example, ethyl ether or tetrahydrofuran, at elevated temperature, generally in the range of from about 40°C. to about 75°C. The ketodiene (Ia-1) is then added to the Grignard solution at about room temperature, although higher or lower temperatures can be employed. The resulting reaction product is hydrolyzed to produce the free alcohol, which can be esterified as discussed above.

Alternatively, the alcohols can be prepared by reaction of ketodiene (Ia-1) with a hydrocarbyl alkali metal compound such as methyl lithium, sodium acetylide, potassium acetylide, and the like.

If a dienone of formula Ia-1 is to be converted to a diene of formula Ia-3 then a starting material of formula Ia-1 wherein the side chain Y includes an oxo group should not be used. Also, during the course of such conversion any ester moieties present in the side chain will be hydrolyzed.

Illustrative examples of the dienes represented by formulae Ia-2 and Ia-3 include 3,6a$\beta$-dimethyl-7$\beta$-hydroxy-1,2,3,5,6,6a,7,8-octahydro-cyclopenta[f][1]benzopyran; 3,6a$\beta$-diethyl-7$\beta$-hydroxy-1,2,3,5,6,6a,7,8-octahydrocyclopenta[f][1]benzopyran; 3-ethyl-6a$\beta$-methyl-7$\beta$-acetoxy-1,2,3,5,6,6a,7,8-octahydrocylopenta[f][1]-benzopyran; 3-ethyl-6a$\beta$-methyl-7$\beta$-benzoyloxy-1,2,3,5,6,6a,7,8-octahydrocylcopenta[f][1]benzopyran; 3-ethyl-6a$\beta$,7$\alpha$-dimethyl-7$\beta$-hydroxy-1,2,3,5,6,6a,7,8-octahydrocylcopenta[f][1]benzopyran; 3,7$\alpha$-diethyl-6a$\beta$-methyl-7$\beta$-hydroxy-1,2,3,5,6,6a,7,8-octahydrocyclopenta[f][1]benzopyran; 3-ethyl-7$\beta$-hydroxy-6a$\beta$-methyl-7$\alpha$-vinyl-1,2,3,5,6,6a,7,8-octahydro-cyclopenta[f][1]benzopyran; 3-ethyl-7$\alpha$-ethynyl-7$\beta$-hydroxy-6a$\beta$-methyl-1,2,3,5,6,6a,7,8-octahydrocyclopenta[f][1]benzoypyran; 7$\beta$-acetoxy-3-ethyl-6a$\beta$7$\alpha$-dimethyl-1,2,3,5,6,6a,7,8-octahydrocyclopenta[f][1]benzopyran; 3-ethyl-7$\beta$-hydroxy-6a$\beta$-dimethyl-1,2,3,5,6,6a,8,9-octahydro-7H-naphtho[2,1-b]pyran; 7$\beta$-hydroxy-6a$\beta$-methyl-3-(4-oxopentyl)-1,2,3,4,5,5a,7,8-octahydrocyclopenta[f][1]benzopyran; 6a$\beta$-ethyl-7$\beta$-hydroxy-3-(4-oxopentyl)-1,2,3,5,6,6a,7,8-octahydrocyclopenta [f][1]benzopyran; 3-[(4,4-ethylenedioxy)pentyl]-7$\beta$-hydroxy-6a$\beta$-methyl-1,2,3,5,6,6a,7,8-octahydrocyclopenta[f][1]benzopyran; 3-[4,4-(2',3')-butylenedioxy-pentyl]-6a$\beta$-ethyl-7$\beta$-hydroxy-1,2,3,5,6,6a,7,8-octahydrocyclopenta[f][1]benzopyran; 3-(4-t-butoxypentyl-7$\beta$-hydroxy-6a$\beta$-methyl-1,2,3,5,6,6a,7,8-octahydrocyclopenta[f][1]benzopyran; 3-(4-t-butoxypentyl)-6a$\beta$-ethyl-7$\beta$-hydroxy-1,2,3,5,6,6a,7,8-octahydrocyclopenta[f][1]benzopyran; 7$\beta$-hydroxy-3-(4-hydroxypentyl)-6a$\beta$-methyl-1,2,3,5,6,6a,7,8-octahydrocyclopenta[f][1]benzopyran and the like.

The second step of the general synthesis of the tricyclic compounds of this invention comprises conversion of the dienes of formula Ia to the monoenes of formula Ib by catalytic hydrogenation. Suitable catalysts include the noble metals, such as platinum, palladium, rhodium, and the like, as well as Raney nickel and other hydrogenation catalysts. These catalysts can be employed in the form of the metal alone, or can be deposited on suitable support materials, such as carbon, alumina, calcium carbonate, barium sulfate, and the like. Palladium and rhodium are preferred as catalysts. The hydrogenation is preferably conducted in the presence of inert solvents such as hydrocarbons, alcohols, ethers, and the like. The reaction conditions of pressure and temperature are not narrowly critical, and normally a hydrogen pressure of about one atmosphere and a temperature of about room temperature are employed. These ambient conditions are generally preferred to avoid significant hydrogenation of the 4a,9b(10b)-double bond, although more severe conditions, for example, up to about 100°C. and up to about 100 atmospheres, can be employed if desired. The hydrogenation medium can be acidic, neutral, or basic, as may be desired, although neutral media, such as hydrocarbons, e.g., toluene or hexane, or basic media, such as alcohol-base, e.g., methanol-sodium hydroxide, mixture are preferred for best results. In general, hydrogenation of the diene of formula Ia leads to the corresponding monoene of formula Ib. However, in the event $R_a$ is an unsaturated hydrocarbyl radical, the hydrogenation, in addition to hydrogenating the ring double bond, also hydrogenates the 7$\alpha$-hydrocarbyl substituent, converting it to an alkyl group.

Via the aforesaid catalytic hydrogenation C/D-trans compounds are formed in a major proportion when hydrogenating a diene of formula Ia-2. This method thus provides an advantageous synthesis of C/D-trans steroidal materials. When hydrogenating a diene of formula Ia-1, C/D-cis compounds are formed in a major proportion. This method thus provides an advantageous synthesis of C/D-cis steroidal materials.

Compounds wherein Z is carbonyl, as represented by the formula:

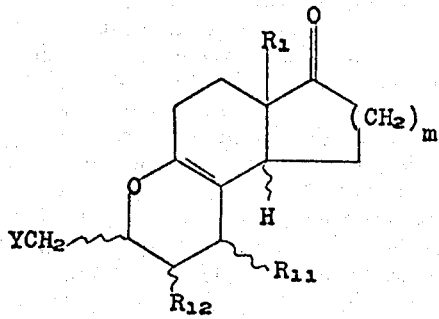

wherein Y, $R_1$, $R_{11}$, $R_{12}$ and $m$ are as previously defined, can be converted to the corresponding alcohols or esters of the formula:

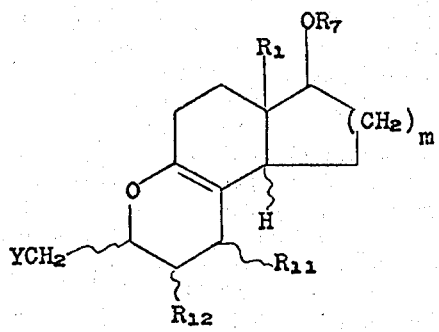

wherein Y, $R_1$, $R_7$, $R_{11}$, $R_{12}$ and $m$ are as previously defined,
or to the 7β-hydroxy-7α-hydrocarbyl compounds of the formula:

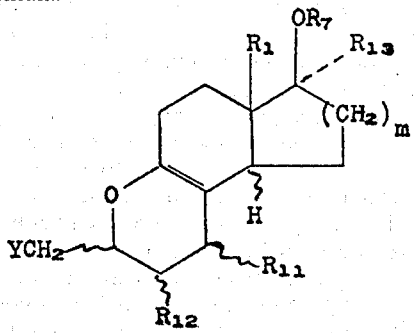

wherein Y, $R_1$, $R_7$, $R_{11}$, $R_{12}$, $R_{13}$ and $m$ are as previously defined,
by the techniques discussed above regarding the dienes of formula Ia.

When Z is carbonyl and the hydrogenation is effected under basic conditions, there is a tendency toward the production of predominantly the 6a/9a(10a)-cis-compound; that is, the hydrogen atom in the 9a(10a)-position of formula Ib-1 is predominantly in the β-orientation. When these compounds are intended as intermediates for the synthesis of steroids having the C/D-trans-orientation, this technique is not particularly desirable. Although the ratio of β- to α-orientation falls to about 1:1 at neutral conditions when hydrogenating a compound wherein Z is carbonyl, it is preferred to hydrogenate a 7β-alcohol or ester of formula Ia-2 because the products of this hydrogenation are predominantly the 6a/9a(10a)-trans-compounds. Compounds of formula Ia-3 when subjected to the hydrogenation yield a ratio of β- to α-orientation in between that of the compounds of formula Ia-1 and that of the compounds of formula Ia-2. When monoenes of formula Ib-1 having C/D-trans configuration are desired, it is preferable to first reduce the dienone of formula Ia-1 to a corresponding hydroxy compound of formula Ia-2 prior to the catalytic hydrogenation. Following the catalytic hydrogenation the carbonyl moiety in formula Ib-1 can be regenerated by conventional means, such as oxidation with chromium trioxide.

The monoene compounds of formula Ib prepared by the abovedescribed hydrogenation contain at least three asymmetric centers, at positions 3, 6a and 9a when $m$ is one and at positions 3, 6a and 10a when m is two. With respect to these three centers there are thus eight antipodal configurations possible. By virtue of the unique asymmetric induction of this invention, proceeding from a racemic starting material of formula II, IIa or IIb only four of these antipodes of formula Ib are prepared and proceeding from an optically active starting material of formula II, IIa, IIb or IIb-1 only two of these antipodes of formula Ib are prepared. Moreover, by the above-described hydrogenation of this invention and by appropriate selection of the 7-substituent in the diene of formula Ia subjected to the hydrogenation there can predominantly be prepared the desired 6a,9a-(10a)-trans-stereo-configuration. Thus, the eventual obtention of the more desired 13β-C/D-trans-configuration in the ultimate steroidal products is rendered more facile by the stereoselective reactions provided by this invention.

Illustrative examples of the monoenes of formula Ib include 3,6aβ-dimethyl-1,2,3,5,6,6a,9,9a-octahydrocyclopenta[f][1]-benzopyran-7(8H)-one; 3,6aβ-diethyl-1,2,3,5,6,6a,9,9a-octahydrocyclopenta[f][1]-benzopyran-7(8H)-one; 3,6aβ-dipropyl-1,2,3,5,6,6a,9,9a-octahydrocyclopenta[f][1]benzopyran-7(8H)-one; 3,6aβ-dimethyl-7β-hydroxy-1,2,3,5,6,6a,7,8,9,9a-decahydrocyclopenta[f][1]-benzopyran; 7β-acetoxy-3,6aβ-dimethyl-1,2,3,5,6,6a,7,8,9,9a-decahydrocyclopenta[f][1]benzopyran; 7β-hydroxy-3,6aβ,7α-trimethyl-1,2,3,5,6,6a,7,8,9,9a-decahydrocyclopenta[f][1]benzopyran; 3,6aβ,7α-triethyl-7β-hydroxy-1,2,3,5,6,6a,7,8,9,9a-decahydrocyclopenta[f][1]benzopyran; 3,6aβ-dimethyl-1,2,3,5,6,6a,8,9,10,10a-decahydro-7H-naphtho-[2,1-b]pyran-7-one; 6aβ-methyl-3-(4-oxopentyl)-1,2,3,5,6,6a,9,9a-octahydrocyclopenta[f][1]benzopyran-7(8H)-one; 6aβ-ethyl-3-(4-oxopentyl)-1,2,3,5,6,6a,9,9a-octahydrocyclopenta[f][1]benzopyran-7(8H)-one; 3-[(4,4-ethylenedioxy)pentyl]-6aβ-methyl-1,2,3,5,6,6a,9,9a-octahydrocyclopenta[f][1]benzopyran-7(8H)-one; 3-(4-t-butoxypentyl)-6aβ-methyl-1,2,3,5,6,6a,9,9a-octahydrocyclopenta[f][1]benzopyran-7-(8H)-one; 3-(4-hydroxypentyl)-6aβ-methyl-1,2,3,5,6,6a,9,9a-octahydrocyclopenta[f][1]-benzopyran-7(8H)-one, 3-(4-hydroxypentyl)16aβ-methyl-1,2,3,5,6,6a,7,8,9,9a-decahydrocyclopenta[f][1]-benzopyran-7-ol, 6aβ-ethyl-3-(4-hydroxypentyl)-1,2,3,5,6,6a,7,8,9,9a-decahydrocyclopenta[f][1]-benzopyran-7-ol and the like.

The final reaction of applicant's general process for the compounds of this invention is the conversion of the monoene of formula Ib to the perhydro compound of formula Ic by reaction of the monoene with a compound having the formula:

$$R_2OH \qquad\qquad VIII$$

wherein $R_2$ is as previously defined.
That is, the monoene of formula Ib is reacted with water, a primary alcohol, or a carboxylic acid. This reaction is catalyzed by mineral or organic acids, for example, hydrochloric acid, phosphoric acid, sulfuric acid, para-toluenesulfonic acid, and the like. Sulfuric acid is the preferred acid catalyst, and water the preferred reactant. Although not necessary, it is desirable to conduct this reaction in the presence of an added solvent, particularly in the event the compound of formula VIII is water. In this case, it is desirable to employ a solvent which is both miscible with water and a solvent for the monoene of formula Ib. Solvents of this nature include acetone, tert.-butanol, dioxane, and the like. The reaction temperature is not critical, and ambient temperature is normally employed, although higher and lower temperatures could be employed if desired.

In addition to the addition of the $R_2OH$ compound, this step effects the conversion of a ketalized side chain such as the 3-[(4,4-alkylenedioxy)pentyl]-group, if present, to the 3-(4-oxopentyl)-group.

As with the compounds of formulae Ia-1 and Ib-1, the compounds of general formula Ic where Z is carbonyl:

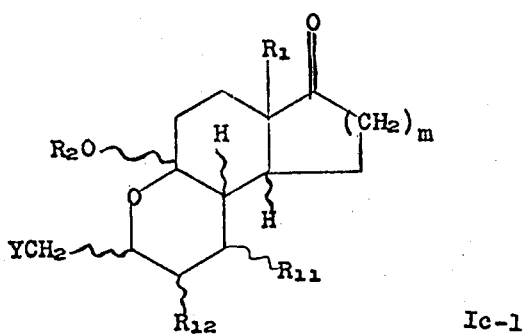

Ic-1 wherein Y, $R_1$, $R_2$, $R_{11}$, $R_{12}$ and m are as previously defined,
are readily converted to their corresponding alcohols:

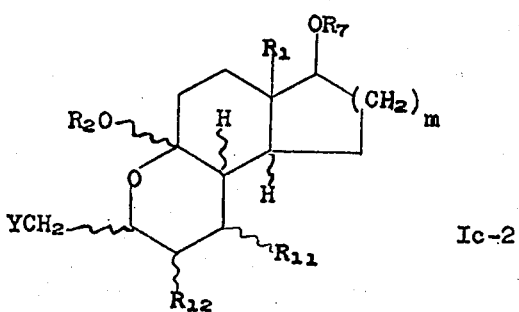

Ic-2 wherein Y, $R_1$, $R_2$, $R_7$, $R_{11}$, $R_{12}$ and m are as previously defined,
or the β-hydroxy-α-hydrocarbyl compounds:

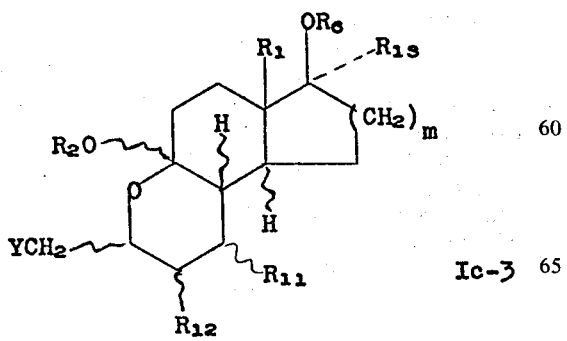

Ic-3 wherein Y, $R_1$, $R_2$, $R_6$, $R_{11}$, $R_{12}$, $R_{13}$ and m are as previously defined, by the previously described methods.

In a modification of the general technique outlined above, one can simultaneously effect the hydrogenation and hydration steps, for example, by hydrogenation of a diene of formula Ia in aqueous sulfuric acid. When this simultaneous hydrogenation-hydration reaction is effected, it is preferred to begin with a diene having a hydroxyl group in the 7β-position.

Illustrative examples of the compounds falling within the scope of formula Ic include 4a-hydroxy-3,6aβ-dimethyl-perhydrocyclopenta[f][1]benzopyran-7-one; 4a-acetoxy-3,6aβ-dimethyl-perhydrocyclopentaf][1-]benzopyran-7-one; 4a-methoxy-3,6aβ-dimethyl-perhydrocyclopenta[f][1]benzopyran-7-one, 3,6aβ-diethyl-4a-hydroxyperhydro-cyclopenta[f][1]benzopyran-7-one, 3-[4,4-(2′,3′) butylenedioxy pentyl]-6aβ-ethyl-4a-hydroxyperhydrocyclopenta[f][1]benzopyran-7-one, 4a,7β-dihydroxy-3,6aβ-dimethyl-perhydrocyclopenta[f][1]benzopyran; 4a,7β-dihydroxy-3,6aβ-7α-trimethyl-perhydrocyclopenta[f][1]-benzopyran; 4a,7β-di(acetoxy)-3,6aβ-dimethyl-perhydrocyclopenta-[f][1]benzopyran; 4a,7β-di(acetoxy)-3,6aβ-dimethyl-perhydronaphtho [2,1-b]pyran; 4a-hydroxy-6aβ-methyl-3-(4-oxopentyl)-perhydrocyclopenta[f][1-]benzopyran-7-one; 3[(4,4-ethylenedioxy) pentyl]-4a-hydroxy-6aβ-methyl-perhydrocyclopenta[f][1]benzopyran-7-one; 3-(4-t-butoxypentyl)-4a-hydroxy-6aβ-methyl-perhydrocyclopenta[f][1]benzopyran-7-one; 4a-hydroxy-3-(4-hydroxypentyl)-6aβ-methyl-perhydrocyclopenta[f][1]benzopyran-7-one, 3-(4-hydroxypentyl)-6aβ-methyl-perhydrocyclopenta[f][1]benzopyran-4a,7-diol, 3-(4-hydroxypentyl)-6aβ-ethyl-perhydrocyclopenta[f][1]benzopyran-4a,7-diol, 6aβ-methyl-3-(4-oxopentyl)-perhydrocyclopenta[f][1]benzopyran-4a,7-diol, and the like.

Although in the various compounds of formula I, as well as their precursors of formulas II, IIa and IIb, the symbol Y comprehends a 3-oxobutyl moiety, it should be noted that it is not preferred to work directly with such oxo-substituted compounds. This is because in many of the reaction steps utilized herein such an oxo moiety would itself be affected. Accordingly, it is preferred to protect such an oxo moiety and regenerate the oxo moiety from its protected form at any desirable stage of the reaction sequence. Protection of the oxo moiety can be effected according to means known per se. Similarly, regeneration of the oxo moiety from its protected form can be effected by means known per se. Thus, one preferred method of effecting protection of the oxo moiety is to convert it to its ketal by reaction with an alkanediol in a known manner. Advantageous results are obtained where protection of the oxo moiety is effected at an early stage in the synthesis. An especially preferred alkanediol is butanediol which affords excellent resistance to attack by nucleophilic reagents. When butanediol is employed, $R_3$ and $R_4$ when taken together are for example, 2,3-butylenedioxy. Similarly an oxo moiety can be converted to its dithia ketal by reaction with dithioethane in a known manner, for example, in acetic acid at room temperature and in the presence of boron trifluoride. Moreover, a monothia ketal can similarly be prepared in a known manner, for example, by reaction of the oxo moiety with 2-mercaptoethanol in dioxane at room temperature in the presence of zinc chloride and sodium sulfate. Also, the monoaza ketals can be prepared in a known manner, for example, by reaction of the oxo moiety with 2-hydroxyethylamine in the presence of acid. Finally, the oxo moiety can be reduced to the corresponding hydroxy compound which can then be etherified or esterified. As indicated above, the oxo moiety can be regenerated from its protected form at any desired stage of the reaction sequence. Thus, it can be readily produced by hydrolysis of the alkylenedioxy ketals in a known manner. Similarly, it can be regenerated from the dithia ketal in a known manner, for example, by treatment with phenylmercuric chloride and calcium carbonate in ethanol or by treatment with dioxane in methanolic hydrochloride. Also, it can be regenerated from a monothia ketal in a known manner, for example, by treatment under strong acidic conditions, for example, by treatment with aqueous sulfuric acid in dioxane or hydrochloride in acetic acid. Moreover, it can be regenerated from a monoaza ketal in a known manner, for example, by treatment with a strong aqueous acid. Also, ethers and/or esters can be reconverted to the free hydroxy group which in turn can be oxidized to give the oxo moiety.

As indicated above, the tricyclic compounds of this invention are useful as intermediates for the preparation of various steroid compounds, depending upon the nature of Y. For example, compounds wherein Y is hydrogen or alkyl lead to $9\beta,10\alpha$-steroids or $10\alpha$-steroids, whereas compounds wherein Y is 3-substituted-butyl, lead to 19-nor-steroids of the normal series, as illustrated by the following reaction scheme.

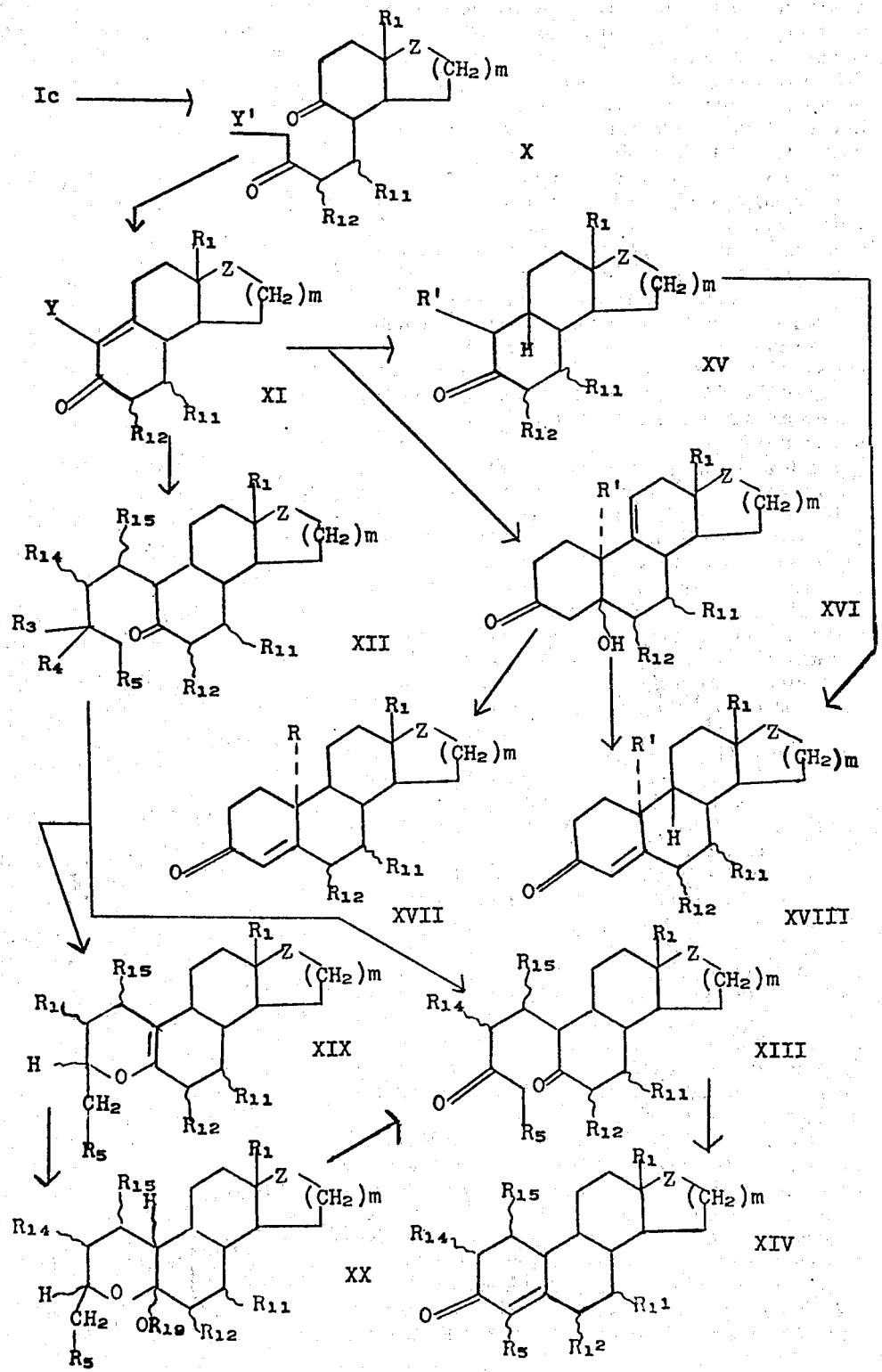

where R' is hydrogen or alkyl; $R_{19}$ is lower alkyl and the remaining symbols are as above.

In the first step of this reaction scheme, the compound of formula Ic is oxidized to form bicyclic compound of the formula X wherein Y' is hydrogen, alkyl, 3-ketalbutyl, or etherified 3-hydroxybutyl, by contact with such oxidizing agents as chromic acid, potassium dichromate, or potassium permanganate. Jones reagent (chromic acid, sulfuric acid and acetone), or a chromic acid-acetic acid mixture are preferred as oxidizing agents. The nature of Z is unchanged in this reaction, except when Z is hydroxymethylene [—CH(OH)—]. In this instance, unless the hydroxyl group is protected, as by formation of a lower acyl ester, it is oxidized to form a carbonyl group. Similar oxidation is effected when compound (Ic) contains as Y a 3-hydroxybutyl group. A hydroxylated product is readily obtained, however, by hydrolysis of a product ester. The reaction temperature is not narrowly critical, and temperatures in the range of from 0°C. to about 75°C. are suitable, although ambient temperatures are preferred.

In the second step, bicyclic compound (X) is treated with acid or base to effect cyclization to (XI). In this reaction, it is preferred that the water of reaction be removed, as by refluxing the reaction mixture with an azeotroping agent in the presence of a strong acid and separating the water from the condensate. Suitable strong acids are sulfuric acid, p-toluenesulfonic acid, potassium bisulfate and the like. Alternatively, base catalyzed dehydration can be utilized, for example, by refluxing compound (X) in the presence of methanolic sodium hydroxide.

The hydrogenation of cyclo-olefin XI to tricyclic compounds XV or XII is preferably effected with a noble metal catalyst, e.g., a palladium-charcoal catalyst or a rhodium catalyst. In formula XV R' represents hydrogen or alkyl. Thus, when compounds of formula XI wherein Y represents hydrogen or alkyl are hydrogenated, compounds of formula XV are obtained, whereas when compounds of formula XI wherein Y represents $R_5CH_2C(R_3,R_4)CH(R_{14})CH(R_{15})$—, hydrogenation yields compounds of formula XII. Hydrogenation products of formula XI are converted to retrosteroids by base catalyzed reaction with methyl vinyl ketone to yield a 9β,10α-androst-4-ene-3-one of formula XVIII. The conversion of compounds of formula XI to compounds of formula XV and of the latter to compounds of formula XVIII are described in greater detail in Belgian Pat. No. 663,197.

Compounds of formula XI wherein Y is R' can also be directly reacted with methyl vinyl ketone yielding a 5-hydroxy-tetracyclic compound of formula XVI. These latter compounds can then be subjected to dehydration followed by hydrogenation or to hydrogenation followed by dehydration to yield 9-,10α- or 10α-steroids of formulas XVII and XVIII. These procedures are described in greater detail in Netherlands Octrooiaanvrage No. 6412939. Still other methods of utilizing compounds of formula XI are described in the literature and other patents.

In those compounds of formula XI where Y is a 3-substituted butyl radical, catalytic hydrogenation over a noble metal catalyst such as palladium gives a 19-nor-4,5-seco compound of formula XII. The 3-substituted butyl radical is then converted to a 3-oxobutyl radical, thus giving a compound of formula XIII.

The conversion of the 3-substituted butyl radical of the compound of formula XII to the 3-oxobutyl radical of the compound of formula XIII can be effected for each particular meaning of $R_3$ and $R_4$ in a manner known per se as described hereinabove for generation of a 3-oxobutyl moiety in compounds of formula I. When $R_3$ and $R_4$ taken together are alkylenedioxy, the conversion of compounds of the formula XII to compounds of the formula XIII proceeds directly in the presence of acid, e.g. hydrochloric acid or sulfuric acid and acetone at room temperature.

However, the conversion of the 3-substituted butyl radical of the compounds of formula XII to the 3-oxobutyl radical of the compounds of formula XIII for other specified values of $R_3$ and $R_4$ defined hereinafter, proceeds through a reaction sequence which yields novel intermediates. When $R_3$ taken alone is etherified hydroxy e.g. lower alkoxy and $R_4$ taken alone is hydrogen; compounds of formula XII, for example 10[3-tertiary-butoxy-butyl]-18-methyl-19-nor-desA-androstan-5,17-dione, can be converted by cyclization to a novel class of enol ethers of the formula:

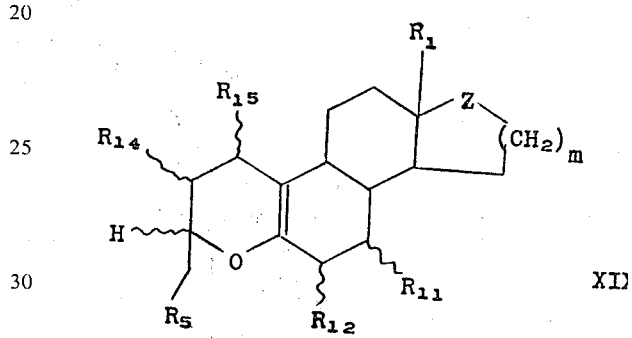

wherein $R_1$, $R_5$, $R_{11}$, $R_{12}$, $R_{14}$, $R_{15}$, Z and m are as above. Exemplary of the compounds of this formula is 6a,9a-trans-2-methyl-6aβ-ethyl-2,3,4,4b,5,6,8,9,9a,9b,10,11-dodecahydrocyclopenta [5,6]naphtho[2,1-b]pyran-7(6aH)-one. Cyclization to the enol ether of formula XIX can be effected by treatment of the alkoxy substituted derivatives of formula XII with acid and heat in a solvent such as for example, benzene or toluene. Suitable acids for the cyclization step are p-toluenesulfonic acid, hydrochloric acid, phosphoric acid, potassium bisulfate and the like. This cyclization is preferably effected at the reflux temperature of the reaction medium although temperatures from between 70° to 130° are suitable.

Further reaction of this novel class of enol ethers by treating with an agent $R_{19}OH$ where $R_{19}$ is hydrogen or lower alkyl, can be accomplished utilizing the same conditions described previously for the reaction of compounds of formulae Ib and VIII e.g. preferably hydration with acid such as sulfuric acid, hydrochloric acid, p-toluenesulfonic acid and the like, in the previously named solvents at room temperature yields compounds of the formula:

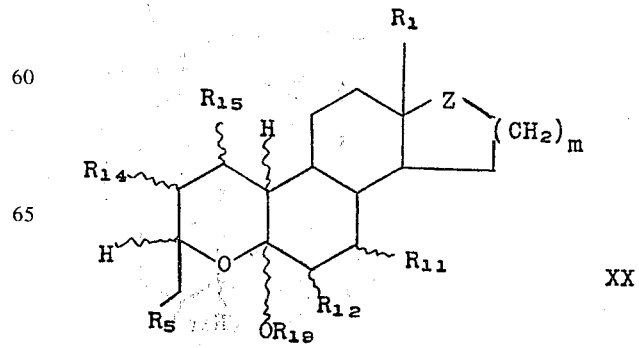

wherein $R_1$, $R_5$, $R_{11}$, $R_{12}$, $R_{14}$, $R_{15}$, $R_{19}$, Z and $m$ are as above. Exemplary of compounds of this formula is 6a,9a-trans-2-methyl-6aβ-ethyl-7-oxo-perhydrocyclopenta[5,6]-naphtho[2,1-b]pyran-11a-ol.

The compounds of formula XX can be further reacted by an oxidation process to produce the diketone compounds of structure XIII. Moreover, where $R_1$ in formula XX is ethyl, i.e., 6a,9a-trans-2-methyl-6aβ-ethyl-7-oxo-perhydrocyclopenta[5,6]naptho[2,1-b]pyran-11a-ol, the oxidation reaction affords the novel compound 10[3-oxo-butyl]-18-methyl-19-nor-desA-androstan-5,17-dione. Exemplary of the suitable oxidizing agents for the reaction, are chromic acid and potassium dichromate. Jones Reagent (chromic acid, sulfuric acid and acetone) is an especially preferred reagent for this purpose. The reaction is carried out in the presence of a mineral acid such as hydrochloric acid or sulfuric acid at room temperature.

Cyclization of the compounds of formula XIII can then be effected to yield 19-nor-androst-4-ene-3-one of the formula XIV. The cyclization reaction of compounds of formula XIII to compounds of formula XIV can be effected by treatment of the compound of formula XIII with acid or base. In this reaction it is preferred that the water of reaction be removed, as by refluxing the reaction mixture with an azeotroping agent in the presence of a strong acid and separating acid, p-toluenesulfonic acid, potassium bisulfate and the like. Alternatively, base-catalyzed dehydration can be utilized, for example, by heating compound XIII in the presence of methanolic sodium hydroxide or potassium t-butylate in t-butanol to about 50°C. Moreover, where $R_1$ in formula XIII is ethyl, for example, 10-[3-oxo-butyl]-18-methyl-19-nor-desA-androstan-5,17-dione, the cyclization process yields the novel 18-homo di-keto compound 13β-ethyl-gon-4-ene-3,17-dione.

Compounds of formula XIV can be selectively alkynylated by a suitable organo metalic acetylide affording norgestrel (13β-ethyl-17α-ethynyl-17-hydroxy-gon-4-ene-3-one). Exemplary of the suitable alkynylating agents to effect the conversion to norgestrel are the alkali acetylides such as lithium acetylide, potassium acetylide, sodium acetylide, etc. The reaction is carried out in the presence of liquid ammonia in a suitable solvent system such as for example, benzene or toluene. The alkynylation is effected preferably at the reflux temperature of the reaction medium although temperatures from between −60° to −30° are suitable. Exemplary of other suitable reagents to effect the acetylenic addition are lithium acetylide ethylenediamine complex in a dimethylformamide solvent and Grignard analogs such as mono and bis acetylenemagnesium halides. The acetylene addition, known with 13-methyl-substituted steroids, is similarly effected with the more bulky 13-ethyl-substituted steroid notwithstanding the increased steric hindrance in the latter configuration.

The above and other methods for utilizing compounds of formulas XII and XIII as intermediates in syntheses of steroidal materials are described in published patents and in the literature, such as French Pat. Nos. 1,364,556; 1,452,898; 1,432,569 and 1,465,400.

In an alternate procedure not depicted in the subject reaction scheme certain compounds of formula XI wherein Y is 3-hydroxybutyl or an ether or ester protected derivative thereof can be converted to enol ethers of formula XIX via novel dienol ethers of formula XXV according to the following scheme:

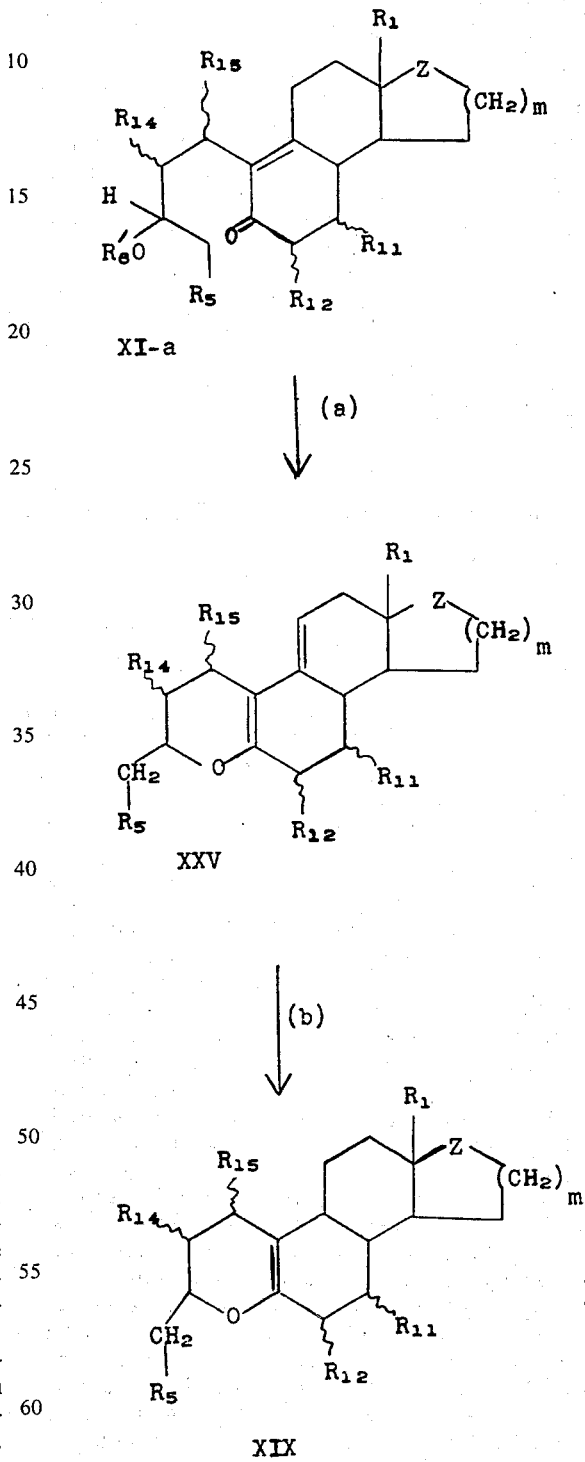

wherein $Z, R_1, R_5, R_{11}, R_{12}, R_{14}$ and $R_{15}$ are as above and $R'_6$ is hydrogen, lower alkyl, acyl, monocyclic carbocyclic aryllower alkyl or a radical of the formula

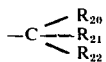

wherein each of $R_{20}$, $R_{21}$ and $R_{22}$ independently is lower alkyl.

It is to be understood that compounds of formula XI-a where $R'_6$ is other than hydrogen, lower alkyl or acyl can be readily prepared from compounds of formula XI where $R_3$ is hydroxy by reacting the latter compound with a halo derivative of the radical to be introduced such as a monocyclic carbocyclic aryl lower alkylhalide or

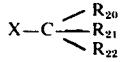

where X is halo using conditions otherwise well known in the art for such reaction.

As used above the term monocyclic carbocyclic aryl denotes a phenyl or substituted phenyl radical. Substituted phenyl radicals have one or more of the same or different substituents attached to any position available for substitution. Substituents on the aryl group may include, for example, lower alkyl, e.g. methyl, ethyl and the like; etherified hydroxyl, such as, lower alkoxy, e.g., methoxy, ethoxy, and the like. The term monocyclic carbocyclic aryl-lower alkyl comprehends, for example, phenyl-lower alkyl, e.g., benzyl, 1-phenylethyl, 2-phenylethyl, and the like included aryl substituted derivatives thereof.

In step (a) of the subject reaction scheme the 10-[3-substituted-alkyl]-$\Delta^{(9-10)}$-des A-steroids of Formula XI-a are cyclized to yield the novel dienol ether compound of formula XXV. The cyclization is suitably effected by the application of heat in the presence of a mineral acid, such as sulfuric acid or hydrogen halides, e.g., hydrochloric acid; or an organic acid, preferably an aryl sulfonic acid such as benzene sulfonic acid or p-toluene sulfonic acid. The cyclization reaction can be conducted in any suitable inert organic solvent, preferably however, a hydrocarbon such as benzene or toluene is employed. The reaction is conveniently carried out at the reflux temperature of the solvent although lower reaction temperatures can also be employed consistent with carrying out the reaction in a minimum of time without undue difficulty. When $R_6$ in the compounds of formula XI-a is hydrogen the aforesaid cyclization can be effected by the application of heat alone, acid treatment alone or a combination of both.

In step (b) of the subject scheme dienol ether compounds of formula XXV are converted into enol ether compounds of formula XIX by a novel selective hydrogenation procedure. The hydrogenation can be suitably effected by employing a nobel metal catalyst such as, palladium, platinum and rhodium with the preferred catalyst being palladium. It is preferred to deposit the catalyst on a suitable support material, carbon being found to be most convenient for the purpose. The hydrogenation is suitably conducted in the presence of an inert organic solvent, preferably a hydrocarbon such as benzene or toluene. Ambient conditions of room temperatures and atmospheric pressure are generally preferred to avoid significant hydrogenation of the $\Delta^{(9-10)}$ bond. The hydrogenation must be effected under basic conditions. A most suitable base has been found to be a tri-lower alkylamine, such as, triethylamine.

Compounds of formulae XI, XIV, XVII, XVIII, XIX and XX wherein Z is carbonyl can be converted into corresponding pregnane compounds, i.e., compounds in which Z is of the formula

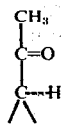

by known procedures. Thus, for example, 19-nor-14$\beta$-androst-4-ene-3,17-dione can be converted into 19-nor-14$\beta$,17$\alpha$-progesterone and desA-androst-9-ene-5,17-dione can be converted into desA-pregn-9-en-5-one. These procedures for converting androst-17-ones into pregnanes are best effected if all carbonyl groups other than that in the 17-position are initially protected.

As has been pointed out above, the products of this invention are produced in the form of various optically active antipodes, which can be carried through the entire reaction sequence, or which can be resolved at suitable places during the reaction sequence. For example, at any stage wherein a compound having a secondary hydroxyl group is present, such as hydroxytetrahydropyran (IV), or any of the hydroxy compounds of formula I, one can react the secondary alcohol with a dicarboxylic acid to form a half-ester. Suitable dicarboxylic acids include lower alkyl dicarboxylic acids such as oxalic acid, malonic acid, succinic acid, glutamic acid, adipic acid, or aromatic carboxylic acids such as phthalic acid. The resulting half-ester is then reacted with an optically active base, such as brucine, ephedrine, or quinine, to produce a diastereomeric salt. The salts, after separation, are then readily reconverted to optically active alcohols. As an alternative, the secondary alcohol can be reacted with an optically active acid, for example, camphorsulfonic acid. The resulting diastereomeric esters are then separated and reconverted to the alcohols.

It is preferred that the resolution be effected at some stage in the synthesis of alken-3-one, as by the above-mentioned resolution of hydroxytetrahydropyran (IV). In a more preferred technique optically active 5-alkyl-5-valerolactone is obtained from 5-alkyl-5-oxopentanoic acid via known microbiological processes. The S-form of this lactone is the preferred form for use in accordance with this invention. In a third method, the racemic lactone can be hydrolyzed to the corresponding hydroxy acid, which is then resolved by treatment with an optically active base in the manner described above. Still other methods will be apparent to those skilled in the art. Resolution at such early stages in the overall process described herein is highly preferred because of the improved efficiency in the production of steroids having a desired stereo-configuration. Because the stereo-configuration is retained throughout the synthesis of alken-3-one (II), and further, because the condensation of alken-3-one or variant (II, IIa or IIb) with cycloalkanedione (III) is stereo-specific, one, by proper selection of stereo-isomers at these early stages, can ensure that substantially all of the tricyclic compounds of this invention and the steroids derived therefrom have a selected stereo-configuration. Thus, by this technique, the production of compounds of the undesired configuration is minimized or prevented entirely, with an attendant increase in the efficiency of the production of compounds of the desired configuration.

In the claims, all compounds shall be construed to include, independently, the racemic form of the compound and independently, each enantiomeric form, i.e., the d and l configurations unless specifically indicated otherwise.

The following examples are illustrative. All temperatures are in degree Centigrade and all products having centers of asymmetry are racemic unless specifically indicated otherwise.

EXAMPLE 1 a. A mixture of 38 grams of 2-methylcyclohexane-1,3-dione, 51 grams of sodium hydroxide, and 450 milliliters of water was hydrogenated over Raney nickel catalyst at a maximum temperature of 140°C. and a maximum pressure of 750 p.s.i. The reaction mixture was filtered and the filtrate, containing sodium 5-hydroxyheptanoate, was acidified with concentrated hydrochloric acid (to a pH of 1), and then refluxed for 30 minutes. The resulting solution was cooled and filtered. The filtrate was extracted with three 1-liter portions of benzene and the combined benzene extracts, after washing with water, drying over sodium sulfate, and evaporation, yielded 26 grams of 5-ethyl-5-hydroxyvaleric acid lactone.

b. A suspension of 5.2 grams of lithium aluminum hydride in 250 milliliters of anhydrous ether was added with stirring over one hour to a solution of 64 grams of 5-ethyl-5-hydroxyvaleric acid lactone in 500 milliliters of anhydrous ether maintained at 0°–5°C. and under a nitrogen atmosphere. After the addition of 250 milliliters of 3N sulfuric acid, the reaction mixture was extracted with three 100-milliliter portions of ether. The combined ether extracts were then washed with two 100-milliliter portions of sodium bicarbonate solution, then with two 150-milliliter portions of water. After drying over sodium sulfate, the etheric solution was evaporated at 45°C. under vacuum to yield 57.1 grams of 6-ethyl-2-hydroxytetrahydropyran.

c. To 7.6 grams of magnesium in 7 milliliters of anhydrous tetrahydrofuran containing a few drops of ethyl bromide and a few milligrams of iodine maintained at 45°–48°C. was added, over a 4-hour period, 120 milliliters of a 20.8 weight per cent solution of vinyl chloride in tetrahydrofuran. The resulting reaction mixture was cooled to 30°C. and a solution of 13 grams of 6-ethyl-2-hydroxytetrahydropyran in 40 milliliters of tetrahydrofuran was added. After standing overnight, there was added ice and ammonium chloride. Extraction of the resulting mixture with three 250-milliliter portions of ether, washing with three 100-milliliter portions of sodium chloride, drying over sodium sulfate, and evaporation gave 16 grams of 3,7-dihydroxy-1-nonene.

d. To a solution of 25 grams of 1-nonene-3,7-diol in 1,250 milliliters of 1,2-dichloroethane was added 0.25 gram of hydroquinone and 300 grams of manganese dioxide. The resulting slurry was stirred vigorously for 1 hour without heating, during which time the reaction temperature rose to about 30°C. The resulting reaction mixture was filtered and the manganese dioxide filter cake was washed thoroughly with 500 milliliters of 1,2-dichloroethane. The combined filtrates were evaporated in vacuo at 40°C. to yield 17.3 grams of 7-hydroxy-1-nonen-3-one. This compound is reacted with hydrogen chloride to produce 1-chloro-7-hydroxynonan-3-one, with dimethylamine to produce 1-(N,N-dimethylamino)-7-hydroxy-nonan-3-one, with water to produce 1,7-dihydroxynonan-3-one, or with ethanol to produce 1-ethoxy-7-hdyroxynonan-3-one.

EXAMPLE 2

Employing procedures similar to those described in Example 1, except that cyclohexane-1,3-dione is substituted for 2-methylcyclohexane-1,3-dione, 7-hydroxyoct-1-en-3-one is produced.

EXAMPLE 3

Employing procedures similar to those described in Example 1, except that 2-ethylcyclohexane-1,3-dione is substituted for 2-methylcyclohexane-1,3-dione, 7-hydroxydec-1-en-3-one is produced.

EXAMPLE 4

A 20 per cent solution of diisobutyl aluminum hydride in 31.4 milliliters of toluene was added over a 30-minute period to a solution of 5 grams of L-(-)-5-pentyl-5-hydroxy-valeric acid lactone in 50 milliliters of toluene at −70°C. After workup of the resulting reaction mixture as described in Example 1(b), there was obtained 5 grams of practically pure optically active 6-pentyl-2-hydroxytetrahydropyran.

To a solution of this product in 20 milliliters of tetrahydrofuran was added at 30°C. a solution of vinyl magnesium chloride in tetrahydrofuran prepared from 3.5 grams of magnesium and excess vinyl chloride in the manner described in Example 1(c). After hydrolysis of the reaction product with an ammonium chloride-ice mixture, followed by extraction with ether, there was obtained 5.72 grams of 3(R,S),7(S)-dihydroxy-1-dodecene as an oil. After crystallization from isopropyl ether-pentane at 0°C., the diol melted at 65.5°–67.5°C. and had an optical rotation $[\alpha]_D^{25} = +5.9°$ as determined from a 1 per cent solution in chloroform.

A solution of 5.22 grams of the diol in 1,2-dichloroethane was stirred with 63 grams of manganese dioxide in the presence of 50 milligrams of hydroquinone for one hour. After filtration to remove the manganese dioxide, washing with additional dichloroethane and ether, and evaporation of the filtrate at 30°C., there was obtained 3.98 grams of optically active 7(S)-hydroxy-1-dodecen-3-one.

EXAMPLE 5

A solution of racemic 7-hydroxy-1-nonen-3-one [21.3 g.; crude obtained as in Example 1(d)] in hexane (200 ml.) was treated for 15 hours at 25°C. with a solution of (−)-α-phenylethylamine (11.5 g.) in hexane (115 ml.). The reaction mixture was then purified by chromatography on alumina (660 g.). Elution with hexane first gave unpolar by-products. Hexane-ether-(4:1)-, (1:1), and straight ether then eluted 2-[2-(1-phenylethylamino)-ethyl]-6-ethyl-2-tetrahydropyranol obtained in solid form after evaporation of the solvents.

EXAMPLE 6

To a solution of the 2-[2-(1-phenylethylamino)ethyl]-6-ethyl-2-tetrahydropyranol (prepared and purified as described in Example 5; 13.87 g., purified by chromatography) in dioxane (200 ml.) a solution of oxalic-acid (4.55 g.; 99.0% anhydrous powder) in dioxane (215 ml.) was added. After standing at 25°C. (65 hours) the precipitated white crystals were filtered off and washed with cold dioxane (20 ml.). Thus, the oxalate of 2-[2-(1-phenylethylamino)ethyl]-6(S)-ethyl-2-tetrahydropyranol was obtained, m.p. 123°–128°, $[\alpha]_D^{25} = -28.2°$ ($c = 1.0$; methanol).

EXAMPLE 7

To 20 g. of magnesium turnings in a 500 ml. flask equipped with dry-ice condenser, thermometer, and dropping funnel, 30 ml. of tetrahydrofuran was added followed by dropwise addition of vinyl chloride solution (200 ml.; 26% solution in tetrahydrofuran) while the oil bath in which the flask was immersed was maintained at 70°. The vinyl chloride was added at such a rate so that the reaction temperature remained at 46°–52°. Iodine vapor and methyl iodide were used to initiate the reaction.

Upon completion of the addition of the vinyl chloride, the reaction mixture was cooled to −5°, and 6-[4,4-(ethylenedioxy)-pentyl]-tetrahydrofuran-2-ol (44.63 g.) dissolved in 150 ml. tetrahydrofuran was added dropwise to the Grignard reagent at −5° to 0°. The resulting mixture was stirred overnight at room temperature.

The solution was then treated with ice and ammonium chloride solution (200 ml.), and the mixture extracted three times, each time with 500 ml. of chloroform. The organic phase was washed once with ammonium chloride solution and twice with water, and then dried over anhydrous sodium sulfate. Removal of the solvent in vacuo afforded crude 11,11-ethylenedioxy-3,7-dihydroxy-1-dodecene as pale yellow liquid which solidified upon refrigeration.

A sample of the crude product was recrystallized once from isopropyl ether-hexane to give clusters of colorless needles which upon three additional recrystallizations from the same solvent provided 11,11-ethylenedioxy-3,7-dihydroxy-1-dodecene which melted at 52°–54°.

A solution of 22.0 g. of 11,11-ethylenedioxy-1-dodecene-3,7-diol in benzene (600 ml.) and diethylamine (40 ml.) was treated under vigorous stirring with manganese dioxide (108 g.) at 25°C. After stirring for 18 hours at room temperature, the manganese dioxide was filtered off and washed with benzene. After evaporation of the filtrate crude 2-(2-diethylaminoethyl)-6-(4,4-ethylenedioxypentyl)-2-tetrahydropyranol was obtained.

A sample of the crude 11,11-ethylenedioxy-3,7-dihydroxy-1-dodecene (10 g.; prepared as described above) was dissolved in dichloroethane (250 ml.), and to this solution activated manganese dioxide (60 g.) was added. The mixture was stirred for 1 hour at room temperature, filtered, and the filter cake washed 3 times, each time with 250 ml. of dichloroethane. Concentration of the combined filtrate afforded crude 11,11-ethylenedioxy-7-hydroxy-1-dodecen-3-one.

EXAMPLE 8

A mixture of 8.3 grams of 7-hydroxy-1-nonen-3-one, 7 grams of 2-methylcyclopentane-1,3-dione, 0.1 gram of hydroquinone, 4.2 milliliters of pyridine, and 42 milliliters of toluene was refluxed under a nitrogen atmosphere for two hours employing a Dean-STark water-collection apparatus. The reaction solution, after cooling, was filtered to recover unreacted 2-methylcyclopentane-1,3-dione. The filtrate was evaporated to dryness, yielding 9.78 grams of crude 3-ethyl-6aβ-methyl-1,2,3,5,6,6a hexahydrocyclopenta[f][1]benzopyran-7(8H)-one. A mixture of the crude product, 1 gram of charcoal, and 100 milliliters of ether was refluxed for 5 minutes. After decantation, the resulting solution was concentrated and 20 milliliters of hexane was added to cause crystallization. A frist crop of 3.88 grams was obtained which melted at 96°–99°C. After concentration of the mother liquor and crystallization from a cold diisopropyl ether/hexane mixture, a second crop of crystals melting at 100°–103°C. was obtained.

Employing similar procedures 3-ethyl-6aβ-methyl-1,2,3,5,6,6a, hexahydrocyclopenta[f][1]benzopyran-7(8H)-one is prepared by substituting 1-chloro-7-hydroxynonan-3-one for the 7-hydroxy-1-nonen-3-one.

EXAMPLE 9

A mixture of 16.2 grams of 7-hydroxy-1-nonen-3-one, 11.5 grams of 2-methylcyclopentane-1,3-dione, 210 milliliters of xylene, and 105 milliliters of acetic acid was refluxed for 1½ hours. After evaporation, the crude reaction product, weighing 27.9 grams, was extracted with two 135-milliliter portions of benzene. The remaining residue, which weighed 1.7 grams, was unreacted 2-methylcyclopentane-1,3-dione. The benzene extracts were combined and evaporated to yield 25 grams of crude product. A solution of this product in hexane was filtered through alumina and, after evaporation of the hexane and crystallization of the product from a hexane-pentane mixture, there was obtained 16.6 grams of 3-ethyl-6aβ-methyl-1,2,3,5,6,6a-hexahydrocyclopenta[f][1]benzopyran-7(8H)-one, melting point 104°–106°C.

Employing similar procedures 3-ethyl-6aβ-methyl-1,2,3,5,6,6a-hexahydrocyclopenta[f][1]benzopyran-7(8H)-one is prepared by substituting 1-(N,N-dimethylamino)-7-hydroxynonan-3-one for the 7-hydroxy-1-nonen-3-one.

EXAMPLE 10

A mixture of 1.56 grams of 7-hydroxy-1-nonen-3-one, 1.12 grams of 2-methylcyclopentane-1,3-dione, and 50 milliliters of toluene was refluxed for 6 hours. Workup of the reaction mixture in the manner described in Example 9 yielded 3-ethyl-6aβ-methyl-1,2,3,5,6,6a-hexahydrocyclopenta[f][1]benzopyran-7(8H)-one.

EXAMPLE 11

A mixture of 1.56 grams of 7-hydroxy-1-nonen-3-one, 1.12 grams of 2-methylcyclopentane-1,3-dione, 16 milliliters of p-dioxane, and 80 milligrams of p-toluenesulfonic acid was reacted at 25°C. for 22 hours. Employing the work-up procedures of Example 9, there was obtained 3-ethyl-6aβ-methyl-1,2,3,5,6,6a-hexahydrocyclopenta[f][1]benzopyran-7(8H)-one.

EXAMPLE 12

A mixture of 1.56 grams of 7-hydroxy-1-nonen-3-one, 1.12 grams of 2-methylcyclopentane-1,3-dione, 0.16 grams of p-toluenesulfonic acid, and 16 milliliters of benzene was refluxed for 30 minutes and worked up as described in Example 9 to yield 3-ethyl-6aβ-methyl-1,2,3,5,6,6a-hexahydrocyclopenta[f][1]benzopyran-7(8H)-one.

EXAMPLE 13

A mixture of 1.56 grams of 7-hydroxy-1-nonen-3-one, 1.12 grams of 2-methylcyclopentane-1,3-dione, 16 milliliters of toluene, 0.8 milliliter of pyridine, and 0.16 gram of p-toluenesulfonic acid was refluxed for 30 minutes. After treatment of the reaction mixture as described in Example 9, there was obtained 3-ethyl-6aβ-methyl-1,2,3,5,6,6a-hexahydrocyclopenta[f][1]benzopyran-7(8H)-one.

EXAMPLE 14

A mixture of 1.56 grams of 7-hydroxy-1-nonen-3-one, 1.12 grams of 2-methylcyclopentane-1,3-dione, 25 milliliters of toluene, 5 milliliters of cyclohexanone, and 0.3 gram of aluminum isopropoxide was refluxed under a nitrogen atmosphere for one hour. After workup as described in Example 15 below, there was obtained 3-ethyl-6aβ-methyl-1,2,3,5,6,6a hexahydrocyclopenta[f][1]benzopyran-7(8H)-one, melting point 100°–102°C.

EXAMPLE 15

A mixture consisting of 1.56 grams of 7-hydroxy-1-nonen-3-one, 1.12 grams of 2-methylcyclopentane-1,3-dione, and 0.16 gram of potassium acetate in tert.-butanol, was held at 25°C. for 20 hours. The resulting reaction mixture was extracted with three 200-milliliter portions of ether. After washing each ether extract with three 100-milliliter portions of water, the ether extracts were combined, dried over sodium sulfate, filtered, and evaporated to dryness. The residue which weighed 2.16 grams was dissolved in 22 milliliters of hexane and chromatographed on alumina. After elution with hexane and evaporation of the hexane, there was obtained spiro[4a-methyl-7a-hydroxy-2,3,4,4a,5,6,7,7a-octahydrocyclopenta[b]pyran-5-one-2,2′-(6′-ethyltetrahydropyran)], melting point 88°–95°C. The melting point was 93°–97°C. after sublimation at 65°C. and 0.01 mm.

EXAMPLE 16

A mixture of 0.3 gram of 7-hydroxy-1-nonen-3-one, 0.3 gram of 2-methylcyclopentane-1,3-dione, 6 milliliters of tert.butanol, and 15 milligrams of sodium hydroxide was held at 25°C. for 2½ days yielding spiro[-4a-methyl-7a-hydroxy-2,3,4,4a,5,6,7,7a-octahydrocyclopenta[b]pyran-5-one-2,2′-(6′-ethyltetrahydropyran)]. The same product was obtained when potassium hydroxide was substituted for sodium hydroxide.

EXAMPLE 17

A mixture of 0.3 gram of 7-hydroxy-1-nonen-3-one, 0.3 gram of 2-methylcyclopentane-1,3-dione, 6 milliliters of toluene, and 0.1 milliliter of a 30 per cent solution of benzyl trimethyl ammonium hydroxide in methanol was held at 25°C. for 5½ days and then heated at 50°C. for 15 hours yielding spiro[4a-methyl-7a-hydroxy-2,3,4,4a,5,6,7,7a-octahydrocyclopenta[b]-pyran-5-one-2,2′-(6′-ethyltetrahydropyran)].

EXAMPLE 18

A mixture of 100 milligrams of spiro[4a-methyl-7a-hydroxy-2,3,4,4a,5,6,7,7a-octahydrocyclopenta[b]pyran-5-one-2,2′-(6′-ethyltetrahydropyran)], 5 milliliters of benzene, and 10 milligrams of p-toluenesulfonic acid was held at 25°C. for 20 hours. After workup in the manner described in Example 15 and crystallization from hexane, there was obtained pure 3-ethyl-6aβ-methyl-1,2,3,5,6,6a-hexahydrocyclopenta[f][1]benzopyran-7(8H)-one.

EXAMPLE 19

Employing apparatus and procedures similar to those described in Example 8, except that 2-ethylcyclopentane-1,3-dione is substituted for 2-methylcyclopentane-1,3-dione, there is produced 3,6aβ-diethyl-1,2,3,5,6,6a-hexahydrocyclopenta[f][1]benzopyran-7(8H)-one melting at 57°–59°C.

EXAMPLE 20

Employing apparatus and procedures similar to those described in Example 8, but substituting 2-methylcyclohexane-1,3-dione for 2-methylcyclopentane-1,3-dione, there is produced 3-ethyl-6aβ-methyl-1,2,3,5,6,6a,8,9-octahydro-7H-naphtho[2,1-b]pyran-7-one melting at 91°–92°C.

EXAMPLE 21

Employing apparatus and procedures similar to those described in Example 8, but substituting 2-ethylcyclohexane-1,3-dione for 2-methylcyclopentane-1,3-dione, there is produced 3,6aβ-diethyl-1,2,3,5,6,6a,8,9-octahydro-7H-naphtho[2,1-b]pyran-7-one.

EXAMPLE 22

Employing apparatus and procedures similar to those described in Example 8, but substituting 7-hydroxy-1-octen-3-one for 7-hydroxy-1-nonen-3-one, there is produced 3,6aβ-dimethyl-1,2,3,5,6,6a-hexahydrocyclopenta[f][1]benzopyran-7(8H)-one.

EXAMPLE 23

Employing apparatus and procedures similar to those described in Example 19, but substituting 7-hydroxy-1-octen-3-one for 7-hydroxy-1-nonen-3-one and 2-ethyl-cyclopentane-1,3-dione for 2-methylcyclopentane-1,3-dione, there is produced 6aβ-ethyl-3-methyl-1,2,3,5,6,6a-hexahydrocyclopenta[f][1]benzopyran-7(8H)-one.

EXAMPLE 24

Employing apparatus and procedures similar to those described in Example 8, but substituting 7-hydroxy-1-decen-3-one for 7-hydroxy-1-nonen-3-one, there is produced 6aβ-methyl-3-propyl-1,2,3,5,6,6a-hexahydrocyclopenta[f][1]benzopyran-7(8H)-one.

EXAMPLE 25

A mixture of the optically active 7-hydroxy-1-dodecen-3-one, obtained as described in Example 4, 2.25 grams of 2-methylcyclopentane-1,3-dione, 50 milliliters of xylene, and 25 milliliters of acetic acid was refluxed for 1½ hours under a nitrogen atmosphere. After evaporation under vacuum, the residue was extracted with cold benzene leaving 400 milliliters of unreacted methylcyclopentanedione as an insoluble residue. The benzene solution was then evaporated to yield 5.56 grams of optically active 3-pentyl-6aβ-methyl-1,2,3,5,6,6a-hexahydrocyclopenta]f][1]benzopyran-7(8H)-one. After chromatographing the crude product on alumina, followed by crystallization from methanol-water, the product melted at 60°–61°C., $[\alpha]_D^{25}$ −166°.

EXAMPLE 26

A mixture of 2-methyl-cyclopentane-1,3-dione (2.24 g.), xylene (100 ml.) and glacial acetic acid (25 ml.) was refluxed under a nitrogen atmosphere for 2 minutes. Then optically active 2-[2-(1-phenylethylamino)ethyl]-6-ethyl-2-tetrahydropyranol oxalate (6.4 g., prepared as described in Example 6) was added and the mixture refluxed for 1 hour. The resultant solution was then washed with $H_2O$ (2 × 50 ml.), saturated $NaHCO_3$ solution (2 × 50 ml.) and $H_2O$ (1 × 50 ml.). The aqueous phases were extracted with benzene (2 × 150 ml.). The combined benzene and xylene fractions were evaporated and the residue (2.4 g.) was chromatographed on alumina (160 g.). With hexane and hexan-ether-(19:1) (total 13 fractions, 160 ml. each) pure 3-ethyl-6a$\beta$-methyl-1,2,3,5,6,6a-hexahydro-cyclopenta[f][1]benzopyran-7(8H)-one was eluted. After evaporation of fractions 3-11 (pure by thin layer chromatography analysis) yellow crystals resulted. This product had a rotation of $[\alpha]_D^{25}$ —145.3° (c = 1.0; $CHCl_3$). Recrystallization from pentane afforded 3-ethyl-6a$\beta$-methyl-1,2,3,5,6,6a-hexahydrocyclopenta[f][1]benzopyran-7(8H)-one as beige crystals m.p. 97°–100°, $[\alpha]_D^{25}$ —145.7° (c = 1.0; $CHCl_3$).

EXAMPLE 27

A mixture of 2-methyl-cyclopentane-1,3-dione (8.6 g.), xylene (157 ml.) and glacial acetic acid (78.5 ml.) was refluxed under a nitrogen atmosphere for 2 minutes. Then a solution of crude 2-(2-diethylaminoethyl)-6-(4,4-ethylenedioxypentyl)-2-tetrahydropyranol (23 g., as prepared in Example 7) in xylene (78.5 ml.) was added to the reaction mixture during 15 minutes. The mixture was then refluxed for another 15 minutes and then worked up by extraction with ether (3 times), washing of the combined extracts with sodium bicarbonate solution and water, drying over sodium sulfate, filtration, and evaporation of the filtrate at 50°C. in vacuo to give a crude mixture of 3-(4,4-ethylenedioxypentyl)-6a$\beta$-methyl-1,2,3,5,6,6a-hexahydrocyclopenta[f][1]benzopyran-7(8H)-one, 4-(3-hydroxy-7(oxooctyl)-7a$\beta$-methyl2,3,5,6,7,7a-hexahydroinden-1,5(1H)-dione and 3-(4-oxopentyl)-6a$\beta$-methyl-1,2,3,5,6,6a-hexahydrocyclopenta[f][1]benzopyran7(8H)-one. This mixture was separated by chromatography on alumina. Elution with hexane afforded 3-(4,4-ethylenedioxypentyl)6a$\beta$-methyl-1,2,3,5,6,6a-hexahydrocyclopenta[f][1]benzopyran-7(8H)-one, elution with hexane-ether (9:1) afforded 3-3-(4-oxopentyl)-6a$\beta$-methyl-1,2,3,5,6,6a-hexahydrocyclopenta[f][1]benzopyran7(8H)-one and elution with chloroform afforded 4-(3-hydroxy-7-oxooctyl)-7a$\beta$-methyl-2,3,5,6,7,7a-hexahydroinden-1,5(1H)-dione an oil.

A mixture of pure 3(4,4-ethylenedioxypentyl)-6a$\beta$-methyl1,2,3,5,6,6a-hexahydrocyclopenta[f][1]benzopyran-7(8H)-one (2.86 g.), acetone (56 ml.) and 1N sulfuric acid (5.6 ml.) was allowed to stand at room temperature for 18 hours. The workup by extraction with ether (3 times), washing of the combined extracts with sodium bicarbonate solution and water, drying over sodium sulfate, filtration, and evaporation of the filtrate at 50°C in vacuo gave a crude mixture of 4-(3-hydroxy-7-oxooctyl)-7a$\beta$-methyl2,3,5,6,7,7a-hexahydroinden-1,5(1H)-dione and 3-(4-oxopentyl)-6a$\beta$-methyl-1,2,3,5,6,6a-hexahydrocyclopenta[f][1]benzopyran7(8H)-one. This mixture was separated by chromatography on silica gel (52 g.). Elution with hexane-ether (1:1and ether alone afforded pure 3-(4-oxopentyl)-6a$\beta$-methyl-1,2,3,5,6,6a-hexahydrocyclopenta[f][1]benzopyran-7(8H)-one (m.p. 74°–85°C., thin layer chromatography, one spot). Elution with methanol afforded 4-(3-hydroxy-7-oxooctyl)-7a$\beta$-methyl-2,3,5,6,7,7a-hexahydroinden-1,5(1H)-dione as an oil (thin layer chromatography, one spot).

A mixture of 4-(3-hydroxy-7-oxooctyl)-7a$\beta$-methyl-2,3,5,6,7,7a-hexahydroinden-1,5(1H)-dione (1.7 g.), benzene (50 ml.) and p-toluenesulfonic acid (170 mg.) was refluxed for 2 hours. The workup by extraction with ether (3 times), washing of the combined extracts with sodium bicarbonate solution and water, drying over sodium sulfate, filtration, and evaporation of the filtrate at 50°C. in vacuo gave crude 3-(4-oxopentyl)-6a$\beta$-methyl-1,2,4,5,6,6a-hexahydrocyclopenta[f][1]benzopyran-7(8H)-one which was chromatographed on alumina (46.5 g.). Elution with hexane-benzene (9:1), (4:1), (1:1) and (1:2) afforded pure 3(4-oxopentyl)-6a$\beta$-methyl1,2,3,5,6,6a-hexahydrocyclopenta[f][1]benzopyran-7(8H)-one (thin layer chromatography, one spot).

EXAMPLE 28

A solution of 3-(4-oxopentyl)-6a$\beta$-methyl-1,2,3,5,6,6a-hexahydrocyclopenta[f][1]benzopyran-7(8H)-one (1.36 g.) in tetrahydrofuran (60 ml.) was added at 0°C. within 15 minutes to a mixture of lithium aluminum hydride (262 mg.) in tetrahydrofuran (40 ml.), with stirring and under a nitrogen atmosphere. The reaction mixture was stirred for an additional 30 minutes at 0°C. and then worked up by careful addition of water, filtration and evaporation of the filtrate in vacuo at 38°C. yielding crude 3-(4-hydroxypentyl)-6a$\beta$-methyl-1,2,3,5,6,6a,7,8-octahydrocyclopenta[f][1]benzopyran-7-ol(thin layer chromatography, one spot) was obtained.

EXAMPLE 29

A solution of 1 gram of 3-ethyl-6a$\beta$-methyl-1,2,3,5,6,6ahexahydrocyclopenta[f][1]benzopyran-7(8H)-one in 20 milliliters of tetrahydrofuran was added over a 15-minute period to a stirred mixture of 100 milligrams of lithium aluminum hydride in 25 milliliters of tetrahydrofuran maintained at 0°C. and under a nitrogen atmosphere. After stirring at 0°C. for an additional hour, a few drops of concentrated sodium hydroxide solution was added. The resulting solution was filtered and evaporated to give 0.982 gram of 3-ethyl-6a$\beta$-methyl-1,2,3,5,6,6a,7,8-octahydrocyclopenta[f][1]benzopyran-7-ol melting at 107°–109°C.

Treatment of 235 milligrams of the product for 20 hours at room temperature with 0.28 gram of benzoyl chloride in 2 milliliters of pyridine as a solvent yielded the 7-benzoate ester.

Treatment of 200 milligrams of the product alcohol for 20 hours at 25°C. with 0.5 milliliter of acetic anhydride in 1 milliliter of pyridine yielded the 7-acetate.

EXAMPLE 30

Employing procedures similar to those described in Example 29 but substituting 3,6a$\beta$-diethyl-1,2,3,5,6,6a-hexahydrocyclopenta[f][1]benzopyran-7(8H)-one for the 3-ethyl-6a$\beta$-methyl1,2,3,5,6,6a-hexahydrocyclopenta[f][1]benzopyran-7(8H)-one, 3,6a$\beta$-diethyl-1,2,3,5,6,6a7,8-octahydrocyclopenta[f][1]benzopyran7-ol is produced.

EXAMPLE 31

In a manner similar to that described in Example 29, 3,6aβ-dimethyl-1,2,3,5,6,6a-hexahydrocyclopenta[f][1]benzopyran-7(8H)-one is reduced to its corresponding alcohol.

EXAMPLE 32

Employing procedures similar to those described in Example 29, 6aβ-methyl-3-propyl-1,2,3,5,6,6a-hexahydrocyclopenta[f][1]-benzopyran-7(8 H)-one is reduced to 6aβ-methyl-3-propyl-1,2,3,5,6,6a,7,8-octahydrocyclopenta[f][1]benzopyran-7-ol.

EXAMPLE 33

Employing procedures similar to those described in Example 29, except that 3-ethyl-6aβ-methyl-1,2,3,5,6,6a,8,9-octahydronaphtho[2,1-b]pyran-7-one is substituted for the 3-ethyl-6aβ-methyl-1,2,3,5,6,6a-hexahydrocyclopenta[f][1]benzopyran-7(8H)-one, there is produced 3-ethyl-6aβ-methyl-1,2,4,5,6,6a,8,9-octahydro7H-naphtho[2,1-b]pyran-7-ol.

EXAMPLE 34

In a manner similar to that described in Example 29, 3,6aβ-diethyl-1,2,3,5,6,6a,8,9-octahydro-naphtho[2,1-b]pyran-7-one is reduced to its corresponding alcohol.

EXAMPLE 35

A solution of a 1.37-gram portion of the optically active enol ether produced as described in Example 25 in 25 milliliters of tetrahydrofuran was added over a 15-minute period to a stirred solution of 137 milligrams of lithium aluminum hydride in 30 milliliters of tetrahydrofuran at 0°C. and under a nitrogen atmosphere. After stirring for an additional 30 minutes at 0°C. and the addition of water to the reaction mixture, the mixture was worked up in the manner described in Example 29 to yield 1.39 grams of optically active 3-pentyl-6aβ-methyl-1,2,4,5,6,6a,7,8-octahydrocyclopenta[f][1]benzopyran-7-ol.

EXAMPLE 36

A solution of crude 3-(4-hydroxpentyl)-6aβ-methyl1,2,3,5,6,6a-hexahydrocyclopenta[f][1]-benzopyran-7(8H)-ol (1.52 g., obtained by the procedure of Example 28) in pyridine (15 ml.) was treated with acetic acid anhydride (7.5 ml.) at room temperature. After standing at room temperature for 20 hours the reaction mixture was treated with methanol (23 ml.) at 0°C. After standing for 30 minutes it was then extracted with benzene (3 times), the combined benzene extracts were washed with H₂O, in HCl, saturated NaHCO₃ solution and again with H₂O. The benzene extract was then evaporated and the residue purified by chromatographed on alumina (53.4 g.). Elution with hexane and hexane-ether (9:1) afforded pure 7β-acetoxy-3-(4-acetoxypentyl)-6aβ-methyl1,2,3,5,6,6a,7,8-octahydrocyclopenta[f][1]benzopyran (thin layer chromatography, one spot).

EXAMPLE 37

A mixture of 11,11-ethylenedioxy-1-dodecene-3,7-diol (5.0 g.), acetone (100 ml.) and 1N sulfuric acid (25 ml.) was stirred at room temperature for 6 hours. After the workup by extraction with ether (3 times), washing of the combined extracts with sodium bicarbonate solution and water, drying over sodium sulfate, filtration, and evaporation of the filtrate at 50°C. in vacuo crude 11-oxo-1-dodecene-3,7-diol was obtained. This crude product was used for the next step.

A solution of crude 11-oxo-1-dedecene13,7-diol (3.3 g.) in 1,2-dichlorethane (100 ml.) was treated with vigorous stirring with manganese dioxide (20 g.) at room temperature. After stirring for 1 hour, the manganese dioxide was filtered off and washed with 1,2-dichloroethane. After evaporation of the combined 1,2-dichloroethane filtrates, crude 7-hydroxy-1-dodecene-3,11-dione was obtained. This crude product was used for the next step.

A mixture of crude 7-hydroxy-1-dodecene-3,11-dione (2.6 g.), 2-methyl-cyclopentane-1,3-dione (1.6 g.), toluene (35 ml.), pyridine (3.5 ml.) and hydroquinone (60 mg.) was refluxed with stirring for 2½ hours. After extraction with ether (3 times), washing of the combined extracts with sodium bicarbonate solution and water, drying over sodium sulfate, filtration, and evaporation of the filtrate at 50°C. in vacuo crude 3(4-oxopentyl)-6aβmethyl-1,2,3,5,6,6a-hexahydrocyclopenta[f][1]benzopyran-7(8H)-one was obtained. This material was chromatographed on alumina (90 g.). Fractions (90 ml. each) were taken as follows. 1–4 = hexane-benzene (4:1), 5–8 = hexane-benzene (2:1) and 9–12 = hexane-benzene (1:1). Fractions 3-12 afforded 3-(4-oxopentyl)-6aβ-methyl-1,2,3,5,6,6a-hexahydrocyclopenta[f][1]benzopyran-7(8H-one.

EXAMPLE 38

10.0 grams of 3,7-dihydroxy-1-nonene was dissolved in 300 milliliters of benzene and 20 milliliters of diethylamine (dist.). To this solution there was added, under vigorous stirring, at 25°C. 60.0 grams of activated manganese dioxide. The reaction mixture was then stirred at 25°C. for 15 hours and then at 45°C. for 5 hours. The manganese dioxide was then filtered off and the filtrate washed three times, each time, with 50 milliliters of benzene. It was then evaporated to dryness at 45°C in vacuo yielding a crude product which by thin layer chromatography (Thin layer chromatography system: Silica gel G plates, solvent benzene: diethylamine 9:1, detection 50 per cent aqueous para-toluenesulfonic acid solution, 120°C. Visibility of desired product 1-diethylamino-7-hydroxy-nonan-3-one can be improved with I₂ vapors.) was shown to contain mainly 1-diethylamino-7-hydroxy-nonan-3-one plus traces of unreacted starting material 3,7-dihydroxy-1-nonene. this crude product was used without purification for the next step.

6.47 grams of 2-methylcyclopentane-1,3-dione, 130 milliliters of xylene and 65 milliliters of glacial acetic acid was refluxed for 5 minutes. To the resulting solution there was added under refluxing and a nitrogen atmosphere during 15 minutes a solution of 13.25 grams of the above-prepared crude product containing 1-diethylamino-7-hydroxy-nonan-3-one dissolved in 65 milliliters of xylene. The reaction mixture was then refluxed for 15 minutes. The resultant solution was then cooled to 25°C. with an ice bath and then twice washed, each time with 100 milliliters of H₂O, then twice, each time with 100 milliliters of saturated NaHCl₃ solution and then again with 100 milliliters of H₂O. The aqueous phases were twice extracted, each time with 200 milliliters of benzene. After evaporation of the combined xylene and benzene solutions at 55°C. in vacuo, light brownish crystals were obtained which were diluted with 50 milliliters of hexane, filtered off after 5 minutes, and twice washed, each time with 15 milliliters of hexane, yielding dl-3-ethyl-1,2,3,5,6,6a-hexahydro-6aβmethylcyclopenta[f][1]benzopyran-7(8H)-one (melting point 101°–102.5°C., beige crystals were obtained). Further quantities of this product were obtained from the mother liquor by evaporation to dryness and column chromatography using aluminum oxide (40 grams, activity grade III) and hexane as a solvent.

EXAMPLE 39

To a freshly prepared solution of methyl lithium (0.2 g.) in tetrahydrofuran (50 ml.), a solution of 3-ethyl-1,2,3,5,6,6a hexahydro-6aβ-methylcyclopenta[f][1]benzopyran-7(8H)-one (1.0 g.) in tetrahydrofuran (20 ml.) is added at 20°C. within 20 minutes with stirring and under a nitrogen atmosphere. After stirring for 1 hour at 50°C., the reaction mixture is poured onto ice (50 g.) ammonium chloride (5 g. ). Extraction with ether (3 portions, 200 ml. each), washing with water (3 times, 50 ml. each), drying over sodium sulfate, filtration and evaporation gives 3-ethyl-7a,6aβ-dimethyl-1,2,3,5,6,6a,7,8-octahydrocyclopenta[f][1]benzopyran7-ol which is further purified by preparative thin layer chromatography on silica gel plates.

EXAMPLE 40

A solution of 6a,a-trans-a1trans13-ethyl-1,2,3,5,6,6a,7,8,9,9a-decahydro-6aβ-methylcyclopenta[f][1]benzopyran-7-ol (1.5 g.) in dimethylformamide (15 ml.) is slowly (30 minutes) added at 25° to a stirred mixture of chromic acid (0.3 g.), dimethylformamide (30 ml.) and concentrated sulfuric acid (1 drop). Stirring is continued for another 3 hours. After work-up (extraction of the reaction mixture with benzene, washing with water and evaporation of the benzene extracts in vacuo at 40°6a,9a-trans-3-ethyl-1,2,3,5,6,6a,9,9a-octahydro-6aβ-methylcyclopenta[f][1]benzopyran7(8H)-one is obtained as an oil. After purification by column chromatography on aluminum oxide, this ketone is dissolved in tetrahydrofuran (25 ml.) and added (within 25 minutes) to a solution of lithium acetylide (prepared from 0.11 g. of lithium wire and acetylene in 50 ml. of liquid ammonia) at −35°C. with stirring. Stirring is then continued for 15 hours at the reflux temperature of the reaction mixture. After adding dry ammonium chloride (3 g.) and ether (50 ml.) to the reaction mixture, the ammonia was allowed to evaporate. After washing the ether phase with water (3 times), followed by filtration and evaporation in vacuo at 40°, 6a,9a-trans-7a-ethynyl-3-ethyl-1,2,3,5,6,6a,7,8,9,9adecahydro-6aβ-methylcyclopenta[f][1]benzopyran-7-ol is obtained as an oil. Purification is achieved by thick layer chromatography on silica gel plates.

EXAMPLE 41

A mixture of 4.9 grams of 3-ethyl-6aβ-methyl-1,2,5,6,6a,7,8-octahydrocyclopenta[f][1]benzopyran-7-ol produced in a manner similar to that described in Example 29, 160 milliliters of methanol, 1.6 milliliters of 3N sodium hydroxide, and 0.8 gram of 5 per cent palladium-on-charcoal was stirred at room temperature in a nitrogen atmosphere. The hydrogen uptake stopped after 2 hours at which time 520 milliliters had been adsorbed. After addition of 0.3 milliliter of acetic acid, the catalyst was filtered off and the filtrate evaporated to dryness to yield 4.9 grams of product consisting predominantly of 6a,9a-trans-3-ethyl-6aβ-methyl-1,2,3,5,6,6a,7,8,9,9a-decahydrocyclopenta[f][1]-benzopyran-7-ol.

EXAMPLE 42

Employing apparatus and procedures similar to those described in Example 41, but substituting the product of Example 30 for that of Example 29, there is produced predominantly 6a,9a-trans-3,6aβ-diethyl-1,2,3,5,6,6a,7,8,9,9a-decahydrocyclopenta[f][1]-benzopyran-7-ol.

EXAMPLE 43

Employing apparatus and procedures similar to those described in Example 41 but substituting the product of Example 31 for that of Example 29, there is produced predominantly 6a,9a-trans-3,6aβ-dimethyl-1,2,3,5,6,6a,7,8,9,9a-decahydrocyclopenta[f][1]benzopyran-7-ol.

EXAMPLE 44

Employing apparatus and procedures similar to those described in Example 41 but substituting the product of Example 32 for that of Example 29, there is produced predominantly 6a,9a-trans-6aβ-methyl-3-propyl-1,2,3,5,6,6a,7,8,9,9a-decahydrocyclopenta[f][1]benzopyran-7-ol.

EXAMPLE 45

Employing apparatus and procedures similar to those described in Example 41 but substituting the product of Example 33 for that of Example 29, there is produced predominantly 6a,10a-trans-3-ethyl-6aβ-methyl-1,2,3,5,6,6a,8,9,10,11a-decahydro-7H-naphtho[2,1-b]pyran-7-ol.

EXAMPLE 46

Employing apparatus and procedures similar to those described in Example 41 but substituting the product of Example 34 for that of Example 29, there is produced predominantly 6a,10a-trans3,6aβ-diethyl-1,2,3,5,6,6a,8,9,10,10a-decahydro-7H-naphtho[2,1-b]pyran-7-ol.

EXAMPLE 47

The dienol of Example 35 was dissolved in 50 milliliters of toluene and then hydrogenated as described in Example 41, employing 378 milligrams of a 5 per cent palladium-on-charcoal catalyst.. After the uptake of 111 milliliters of hydrogen, there was obtained 1.39 grams of optically active 6a,9a-trans-3-pentyl6aβ-methyl-1,2,3,5,6,6a,7,8,9,9a-decahydrocyclopenta[f][1]benzopyran-7-ol.

EXAMPLE 48

A solution of 7β-acetoxy-3-(4-acetoxypentyl)-6aβ-methyl-1,2,3,5,6,6a,7,8-octahydrocyclopenta[f][1]-benzopyran (1.31 g.; chromatographed) in toluene (50 ml.) was hydrogenated under normal conditions using 5 per cent palladium-on-charcoal catalyst (262 mg.). The uptake (88 ml.) of hydrogen stopped after 5 hours. The workup by extraction with ether (3 times), washing of the combined extracts with sodium bicarbonate solution and water, drying over sodium sulfate, filtration, and evaporation of the filtrate at 50°C. in vacuo gave crude 6a,9a-trans-7β-acetoxy-3-(4-acetoxypentyl)-6aβ-methyl-1,2,3,5,6,6a,7,8,9,9a-decahydrocyclopenta[f][1]benzopyran as an oil.

EXAMPLE 49

A solution of 11,11-ethylenedioxy-7-hydroxy-1-dodecen-3-one (6.7 g.; prepared as described in Example 7) in 25 ml. of toluene was treated with 2-methyl-1,3-cyclopentadione (3.50 g.), pyridine (2.7 ml.), and hydroquinone (140 mg.), and the resulting mixture refluxed for 8 hours using Dean-Stark apparatus.

At the end of the reflux period, the reaction mixture was chilled, the 2-methyl-1,3-cyclopentadione removed by filtration, and the filtrate concentrated in vacuo (water aspirator, 40°). The crude product 3-[4,4-(ethylenedioxy)pentyl]-1,2,3,5,6,6ahexahydro-6a$\beta$-methylcyclopenta[f][1]benzopyran-7(8H)-one (8.15 g.) was chromatographed on 82 g. of neutral alumina Grade III and the column eluted with hexane-10% ether. The eulted fractions 2–10 contained the desired product which was recrystallized once from isopropyl ether-hexane giving almost colorless crystals of 3-[4,4-(ethylenedioxy)pentyl]-1,2,3,5,6,6a-hexahydro-6a$\beta$-methylcyclopenta[f][1]benzopyran-7(8H)-one, a sample of which upon being recrystallized from hexane-ether melted at 69°–72°.

EXAMPLE 50

To lithium aluminum hydride (0.38 g.) in tetrahydrofuran (90 ml.) at 0°, a solution of the 3-[4,4-(ethylenedioxy)pentyl]-1,2,3,5,6,6a-hexahydro-6a$\beta$-methylcyclopenta[f][1]benzopyran-7(8H)-one (3.7 g.) in 75 ml. tetrahydrofuran was added over a period of 15 minutes.

Upon completion of the addition of 3-[4,4-(ethylenedioxy)-pentyl]-1,2,3,5,6,6a-hexahydro-6a$\beta$-methylcyclopenta[f][1]-benzopyran-7(8H)-one, the mixture was stirred at 0° for 1 hour. A small amount of water was then added to the reaction mixture. Concentration of the reaction mixture in vacuo gave a yellow liquid which crystallized upon standing. The product, 3-[4,4-(ethylenedioxy)pentyl]-1,2,3,5,6,6a,7,8-octahydro-6a$\beta$-methylcyclopenta-[f][1]benzopyran-7-ol. was collected by filtration.

A sample of the product, after recrystallization four times from dilute methanol and once from ether-hexane, melted at 91°–93°.

EXAMPLE 51

3-[4,4-(ethylenedioxy)pentyl]-1,2,3,5,6,6a,7,8-octahydro-6a$\beta$-methylcyclopenta[f][1]benzopyran-7-ol (10 g.) was dissolved in 250 ml. of toluene and hydrogenated in the presence of 1.7 g. of 5% palladium-on-charcoal catalyst. During ca. 9 hour period 710 ml. of $H_2$ were consumed. The hydrogenation was performed at room temperature.

At the end of the reaction period the catalyst was removed by filtration, and the solvent removed in vacuo. The crude product was chromatographed on 100 g. of neutral alumina Grade III, and the column eluted with hexane-ether (1:2) giving purified product, 6a,9a-trans-3-[4,4-(ethylenedioxy)pentyl]-1,2,3,5,6,6a,7,8,9,9a-decahydro-6a$\beta$-methylcyclopenta[f][1]benzopyran-7-ol.

EXAMPLE 52

A mixture of 465 milligrams of 3-ethyl-6a$\beta$-methyl-1,2,3,5,6,6a,8-hexahydrocyclopenta[f][19 benzopyran-7(8H)-one, as produced in a manner similar to that described in Example 8, 20 milliliters of toluene, and 150 milligrams of 5 per cent palladium-on-charcoal was hydrogenated under ambient conditions. The hydrogen uptake ceased after 1 hour, after which time 50 milliliters had been adsorbed. After filtering the reaction mixture and evaporation of the filtrate, there was obtained the product monoenol ether as an oil containing predominantly 6a,9a-cis-3-ethyl-6a$\beta$-methyl-1,2,3,5,6,6a,9,9a-octahydrocyclopenta-[f][1]benzopyran-7(8H)-one.

EXAMPLE 53

Employing apparatus and procedures similar to those described in Example 52 but substituting the product of Example 19 for that of Example 8, there is produced predominantly 6a,9a-cis-3,6a$\beta$-diethyl-1,2,3,5,6,6a,9,9a-octahydrocyclopenta[f][1]benzopyran-7(8H)-one.

EXAMPLE 54

Employing apparatus and procedures similar to those described in Example 52 but substituting the product of Example 22 for that of Example 8, there is produced predominantly 6a,9a-cis-3,6a$\beta$-dimethyl-1,2,3,5,6,6a,9,9a-octahydrocyclopenta[f][1]benzopyran-7(8H)-one.

EXAMPLE 55

Employing apparatus and procedures similar to those described in Example 47 but substituting the product of Example 23 for that of Example 7, there is produced predominantly 6a,9a-cis-6a$\beta$-methyl-3-propyl-1,2,3,5,6,6a,9,9a-octahydrocyclopenta[f][1]benzopyran-7(8H)-one.

EXAMPLE 56

Employing apparatus and procedures similar to those described in Example 52 but substituting the product of Example 20 for that of Example 8, there is produced predominantly 6a,10a-cis-3-ethyl-6a$\beta$-methyl-1,2,3,5,6,6a,8,9,10,10a-decahydro-7H-naphtho[2,1-b]pyran-7-one.

EXAMPLE 57

Employing apparatus and procedures similar to those described in Example 52 but substituting the product of Example 21 for that of Example 8, there is produced predominantly 6a,10a-cis-3,6a$\beta$-diethyl-1,2,3,5,6,6a,8,9,10,10a-decahydro-naphtho[2,1-b]pyran-7-one.

EXAMPLE 58

A solution of the 4.9 grams of hydrogenation product obtained in Example 41 in 100 milliliters of acetone and 15 milliliters of 1N sulfuric acid was held at 25°C. for 30 minutes. After extraction of the reaction mixture with ether, washing with water and sodium bicarbonate solution, drying over sodium sulfate, filtration and evaporation, there was obtained 5.1 grams of crude 6a,9a-trans-3-ethyl-6a$\beta$-methylperhydrocyclopenta[f][1]benzopyran-4a,7 -diol. This product on crystallization from an ether-hexane mixture at 0°C. yielded 3.5 grams, melting point 113°–116°C. A second crop weighing 0.4 gram, melting point 114°–117°C., was obtained from the mother liquor. The melting point was increased from 121°–122.5°C. after several additional recrystallizations.

By employing similar procedures but substituting methanol or acetic acid for the water, there are obtained the corresponding 4a-methoxy- and 4a-acetoxy-derivatives, respectively.

EXAMPLE 59

Employing apparatus and procedures similar to those described in Example 58 but substituting the product of Example 42 for that of Example 41, there is produced predominantly 6a,9a-trans-3,6aβ-diethylperhydrocyclopenta[f][1]benzopyran-4a,7-diol.

EXAMPLE 60

Employing apparatus and procedures similar to those described in Example 58 but substituting the product of Example 43 for that of Example 41, there is produced predominantly 6a,9a-trans-3,6aβ-dimethylperhydrocyclopenta[f][1]benzopyran-4a,7-diol.

EXAMPLE 61

Employing apparatus and procedures similar to those described in Example 58 but substituting the product of Example 44 for that of Example 41, there is produced predominantly 6a,9a-trans-6aβ-methyl-3-propylperhydrocyclopenta[f][1]benzopyran-4a,7-diol.

EXAMPLE 62

Employing apparatus and procedures similar to those described in Example 58 but substituting the product of Example 45 for that of Example 41, there is produced predominantly 6a,10a-trans-3-ethyl-6aβ-methylperhydronaphtho[2,1-b]pyran-4a,7-diol.

EXAMPLE 63

Employing apparatus and procedures similar to those described in Example 58 but substituting the product of Example 46 for that of Example 41, there is produced predominantly 6a,10a-trans-3,6aβ-diethylperhydronaphtho[2,1-b]pyran-4a,7-diol.

EXAMPLE 64

A 1.25-gram portion of the crude hydrogenation product obtained as described in Example 47 was dissolved in 25 milliliters of acetone and treated with 1N sulfuric acid as described in Example 58. After standing at 25°C. for 45 minutes and workup of the reaction mixture, there was obtained 1.20 grams of optically active 6a,9a-trans-3-pentyl-6aβ-methylperhydrocyclopenta[f][1]benzopyran-4a,7-diol as an oil.

EXAMPLE 65

A solution of 6-[4-(t-butoxy)pentyl]-tetrahydropyran-2-ol (5 g.) in tetrahydrofuran (50 ml.) was added within 30 minutes at 5° to a solution of vinyl magnesium chloride in tetrahydrofuran, prepared from magnesium (2.0 g.) and 4 g. of vinyl chloride, dissolved in tetrahydrofuran (50 ml.). After stirring overnight at room temperature, the reaction solution was treated with ammonium chloride-ice and then extracted with chloroform (3 times, each time 100 ml.). The organic phase was washed with water, dried and evaporated in vacuo giving crude 3,7-dihydroxy-11-(t-butoxy)-dodec-1-ene.

Crude 3,7-dihydroxy-11-(t-butoxy)-dodec-1-ene (5.8 g., prepared as described above) was dissolved in benzene (200 ml.) and the reaction mixture was then stirred for 2 hours at 25° after addition of activated manganese dioxide (58 g.). Filtration and evaporation of the filtrate at 30° in vacuo afforded crude 7-hydroxy-11-(t-butoxy)-dodec-1-en-3-one.

EXAMPLE 66

A mixture of crude 6a,9a-trans-7β-acetoxy-3-(4-acetoxypentyl)-6aβ-methyl-1,2,3,5,6,6a,7,8,9,9a-decahydrocyclopenta[f][1]benzopyran (1.3 g., obtained by the procedure of Example 48), acetone (30 ml.) and 1N sulfuric acid (15 ml.) was allowed to stand for 1 hour at room temperature. The workup by extraction with ether (3 times), washing of the combined extracts with sodium bicarbonate solution and water, drying over sodium sulfate, filtration, and evaporation of the filtrate at 50°C. in vacuo afforded crude 6a,9a-trans-3-(4-acetoxypentyl)-7β-acetoxy-6aβ-methylperhydrocyclopenta[f][1]benzopyran-4a-ol, which was purified by chromatography on alumina (67.5 g.). Fractions (68 ml. each) were taken as follows: 1-3 = hexane-ether (9:1), 4-6 = hexane-ether (4:1), 7-9 = hexane-ether (2:1) and 10-12 = hexane-ether (1:1). Thin layer chromatography analysis showed fractions 4-10 (1.02 g. after evaporation) to be pure 6a,9a-trans-3-(4-acetoxypentyl)-7β-acetoxy-6aβ-methylperhydrocyclopenta[f][1]benzopyran-4a-ol.

EXAMPLE 67

6a,9a-Trans-3-[4,4-(ethylenedioxy)pentyl]-1,2,3,5,6,6a,7,8,9,9a-decahydro-6aβ-methylcyclopenta[f][1]benzopyran-7-ol (9.04 g., obtained and purified as described in Example 51) was dissolved in acetone (180 ml.) and to this solution 90 ml. of 1N $H_2SO_4$ was added. The reaction mixture was allowed to remain at room temperature for 4 hours before it was neutralized with sodium bicarbonate solution, diluted with ca. 180 ml. of water, and extracted 3 times, each time with 200 ml. of chloroform. The extract was washed three times with water, dried, and the solvent removed to afford a slightly pink-colored, viscous liquid.

This crude product was chromatographed on 240 g. neutral aluminum Grade III, and the column eluted with hexane-ether (1:2 and 1:9) followed by chloroform-ether (1:1). Several of the eluted fractions contained the desired product, 6a,9a-trans-3-[4,4-(ethylenedioxy)pentyl]-6aβ-methylperhydrocyclopenta[f][1]-benzopyran-4a,7β-diol.

EXAMPLE 68

Crude 7-hydroxy-11-(t-butoxy)-dodec-1-en-3-one (4.6 g., obtained as described in Example 65) was dissolved in toluene (46 ml.) and to this solution there was added 2-methylcyclopentane-1,3-dione (3 g.), pyridine (4.6 ml.) and hydroquinone (100 mg.). The reaction mixture was then refluxed for 8 hours, using a Dean-Stark water trap. The workup and chromatography purification was performed as described in Example 8 and afforded 3-[4-(t-butoxy)-pentyl]-6aβ-methyl-1,2,3,5,6,6a-hexahydrocyclopenta[f][1]benzopyran-7(8H)-one.

In order to remove the protective t-butylether group, a 1 g. sample of the product obtained above was refluxed for 5 hours under a nitrogen atmosphere in tetrahydrofuran (50 ml.) containing 10 ml. of 1N hydrochloric acid. Workup by extraction with ether, washing with water and evaporation to dryness in vacuo at 60° yielded 3-(4-hydroxypentyl)-6aβ-methyl-1,2,3,5,6,6a-hexahydrocyclopenta[f][1]benzopyran-7(8H)-one.

A sample of the so-prepared 3-(4-hydroxypentyl)-6aβ-methyl-1,2,3,5,6,6a-hexahydrocyclopenta[f][1-]benzopyran-7(8H)-one (0.5 g.) was dissolved in ether (10 ml.) and reduced by reaction with a solution of lithium aluminum hydride (0.1 g.) in ether (10 ml.) at 0° (1 hour stirring). After addition of 10 drops of water, the reaction mixture was filtered and the filtrate evaporated giving 3-(4-hydroxypentyl)-6aβ-methyl-1,2,3,5,6,6a,7,8-octahydrocyclopenta[f][1]benzopyran-7-ol.

EXAMPLE 69

Employing apparatus and procedures similar to those described in Example 58 but substituting the ketone of Example 52 for the 7-ol of Example 41, there is produced predominantly 6a,9a-cis-3-ethyl-4a-hydroxy-6aβ-methylperhydrocyclopenta[f][1]benzopyran-7-one.

EXAMPLE 70

Employing apparatus and procedures similar to those described in Example 58 but substituting the ketone of Example 53 for the diol of Example 41, there is produced predominantly 6a,9a-cis-3,6aβ-diethyl-4a-hydroxyperhydrocyclopenta[f][1]benzopyran-7-one.

EXAMPLE 71

Employing apparatus and procedures similar to those described in Example 58 but substituting the ketone of Example 54 for the diol of Example 41, there is produced predominantly 6a,9a-cis-3,6aβ-dimethyl-4a-hydroxyperhydrocyclopenta[f][1]benzopyran-7-one.

EXAMPLE 72

Employing apparatus and procedures similar to those described in Example 58 but substituting the ketone of Example 56 for the diol of Example 41, there is produced predominantly 6a,10a-cis-3-ethyl-4a-hydroxy-6aβ-methylperhydronaphtho[2,1-b]pyran-7-one.

EXAMPLE 73

Employing apparatus and procedures similar to those described in Example 58 but substituting the ketone of Example 57 for the diol of Example 41, there is produced predominantly 6a,10a-cis-3,6aβ-diethyl-4a-hydroxyperhydronaphtho[2,1-b]pyran-7-one.

EXAMPLE 74

A mixture of 117 milligrams of 3-ethyl-6aβ-methyl-1,2,3,5,6,6a-hexahydrocyclopenta[f][1]benzopyran-7-ol produced in a manner similar to that described in Example 29, 10 milliliters of isopropanol, 5 milliliters of 1N sulfuric acid, and 20 milligrams of 5 per cent palladium-on-charcoal was hydrogenated at standard temperature and pressure. Workup of the reaction product in the manner described in Example 58, followed by crystallization from an ether-hexane mixture, gave 64 milligrams of 6a,9a-trans-3-ethyl-6aβ-methylperhydrocyclopenta[f][1]benzopyran-4a,7-diol, melting point 108°–112°C.

By employing similar procedures, but substituting methanol or acetic acid for the water, there are obtained the corresponding 4a-methoxy- and 4a-acetoxy- derivatives, respectively.

EXAMPLE 75

A solution of 255 milligrams of 6a,9a-trans-3-ethyl-6aβ-methylperhydrocyclopenta[f][1]benzopyran-4a,7-diol produced as described in Example 58 in 10 milliliters of dichloromethane was treated with a solution of 200 milligrams of chromic acid in 5 milliliters of 3N sulfuric acid and stirred at room temperature for 18 hours. The resulting reaction mixture was worked up as described in Example 58 to yield a crude product which was purified by chromatography on silica gel. Recrystallization of the thus-recovered product from an ether-hexane mixture yielded a sample of 6a,9a-trans-3-ethyl-4a-hydroxy-6aβ-methylperhydrocyclopenta[f][1]benzopyran-7-one melting at 120°–121.5°C.

EXAMPLE 76

A solution of 6.88 grams of chromic acid in 3.45 milliliters of 6N sulfuric acid was added over a 20-minute period to a stirred solution of 3.5 grams of 6a,9a-trans-3-ethyl-6aβ-methylperhydrocyclopenta[f][1]benzopyran-4a,7-diol, produced as described in Example 58, in 143 milliliters of acetone at 25°C. After stirring the reaction mixture for an additional 2¼ hours and workup as described in Example 58, there was worked up 3.0 grams of 3a,7a-trans-4-(3'-oxopentyl)-7aβ-methyl-perhydroinden-1,5-dione. A solution of this product in 172 milliliters of toluene was treated with 792 milligrams of p-toluenesulfonic acid and refluxed for 3 hours using a Dean-Stark water separator. Workup and purification as described in Example 58 yielded 2.68 grams of desA-androst-9-en-5,17-dione, which on crystallization from an ether-isopropyl ether mixture, melted at 101°–102.5°C.

EXAMPLE 77

The product of Example 64 was oxidized with a mixture of 2.04 grams of chromic acid, 45 milliliters of acetone, and 10.2 milliliters of 6N sulfuric acid in the manner described in Example 76 to yield 900 milligrams of 4-(3'-oxo-octyl)-7aβ-methyl-3aβ-perhydroinden-1,5-dione. This triketone was treated with 205 milligrams of para-toluenesulfonic acid in 50 milliliters of toluene as described in Example 69 to yield 790 milligrams of d-(+)-19-butyl-desA-androst-9-en-5,17-dione. After purification by chromatographing on silica gel, the product had an optical rotation $[\alpha]_D^{25} = +60.5°$ as determined from a 30 per cent solution in chloroform.

EXAMPLE 78

To a solution of chromatographed 6a,9a-trans-3-(4-acetoxypentyl)-7β-acetoxy-6aβ-methylperhydrocyclopenta[f][1]benzopyran-4a-ol (1.0 g.) in acetone (30 ml.), a mixture of chromic acid (1.0 g.) in 6N sulfuric acid (5.3 ml.) was added at 20°C. (ice-cooling) with stirring during 5 minutes. After this addition, the mixture was stirred for another 2 hours at room temperature. The workup by extraction with ether (3 times), washing of the combined extracts with sodium bicarbonate solution and water, drying over sodium sulfate, filtration, and evaporation of the filtrated at 50°C. in vacuo afforded crude 3a,7a-trans-4-(7-acetoxy-3-oxooctyl)-1β-acetoxy-7aβ-methyl-perhydroindan-5-one as an oil. This product was used for the next step.

A mixture of 3a,7a-trans-4-(7-acetoxy-3-oxooctyl)-1β-acetoxy-7aβ-methyl-perhydroindan-5-one (crude oxidation product; 940 mg.), benzene (20 ml.) and p-toluenesulfonic acid (94 mg.) was refluxed for 3 hours. Workup by extraction with ether (3 times), washing of the combined extracts with sodium bicarbonate solution and water, drying over sodium sulfate, filtration, and evaporation of the filtrate at 50°C. in vacuo gave crude 17β-acetoxy-10-(3-acetoxybutyl)-

19-nor-desA-androst-9-en-5-one (870 mg.) which was purified by chromatography on silica gel (87 g.). Fractions (87 ml. each) were taken as follows: 1–3 = hexane-ether (4:1), 4–6 = hexane-ether (2:1), 7–9 = hexane-ether (1:1), 10–12 = hexane-ether (1:2) and 13–15 = hexane-ether (1:4). Thin layer chromatographic analysis showed fractions 9–13 (583 mg. after evaporation) to be almost pure 17β-acetoxy-10-(3-acetoxybutyl)-19-nor-desA-androst-9-en-5-one.

EXAMPLE 79

A solution of chromatographed 17β-acetoxy-10-(3-acetoxybutyl)-19-nor-desA-androst-9-en-5-one (535 mg.) in absolute ethanol (30 ml.) and triethylamine (0.15 ml.) was hydrogenated under normal conditions using 5 per cent palladium-on-charcoal catalyst (55 mg.). The uptake (31 ml.) of hydrogen stopped after about 5 hours. Workup by extraction with ether (3 times), washing of the combined extracts with sodium bicarbonate solution and water, drying over sodium sulfate, filtration, and evaporation of the filtrate at 50°C. in vacuo gave 17β-acetoxy-10-(3-acetoxybutyl)-19-nor-desA-androstan-5-one as an oil (535 mg.). This crude product was used for the next step.

A mixture of crude 17β-acetoxy-10-(3-acetoxybutyl)-19-nor-desA-androstan-5-one (535 mg.), ethanol (20 ml.) and 20 per cent sodium hydroxide solution (2.0 ml.) was allowed to stand at room temperature for 20 hours. Workup by extraction with ether (3 times), washing of the combined extracts with sodium bicarbonate solution and water, drying over sodium sulfate, filtration, and evaporation of the filtrate at 50°C. in vacuo afforded crude 17β-hydroxy-10-(3-hydroxybutyl)-19-nor-desA-androstan-5-one (373 mg.). This crude product was used for the next step.

To a solution of crude 17β-hydroxy-10-(3-hydroxybutyl)-19-nor-desA-androstan-5-one (373 mg.) in acetone (15 ml.) a mixture of chromic acid (634 mg.) in 6N sufluric acid (3.2 ml.) was added over a period of 10 minutes with stirring and ice-cooling (20°C.). After this addition the reaction mixture was stirred for another hour at room temperature. Workup by extraction with ether (3 times), washing of the combined extracts with sodium bicarbonate solution and water, drying over sodium sulfate, filtration, and evaporation of the filtrate at 50°C. in vacuo gave crude 10-(3-oxobutyl)-19-nor-desA-androstan-5,17-dione (307 mg.). Thin layer chromatographic analysis showed two major spots plus three minor spots. The two major spots were separated by chromatography on silica gel (30 g.). Elution with benzene-ether (2:1) afforded a by-product. Elution with benzene-ether (1:1) afforded the desired product 10-(3-oxobutyl)-19-nor-desA-androstan-5,17-dione.

EXAMPLE 80

A mixture of 10-(3-oxobutyl)-19-nor-desA-androstan-5,17-dione (chromatographed product; 96.7 mg.), toluene (4 ml.) and p-toluenesulfonic acid (9.7 mg.) was refluxed for 3 hours. Workup by extraction with ether (3 times), washing of the combined extracts with sodium bicarbonate solution and water, drying over sodium sulfate, filtration, and evaporation of the filtrate at 50°C. in vacuo gave crude 19-nor-androst-4-en-3,17-dione. This material was purified by chromatography on silica gel (8.5 g.). Elution with benzene-ether (1:1) afforded 19-nor-androst-4-en-3,17-dione (67.2 mg.). Upon recrystallization from ether-hexane d,1-19-nor-androst-4-en-3,17-dione melted at 156.5°–158°C.

To a stirred solution of 19-nor-androst-4-en-3,17-dione (56.8 mg.; chromatographed product) in tetrahydrofuran (2.5 ml.), tri-tert.-butoxylithium aluminum hydride (105 mg.) was added at 0°C. in one portion. After stirring for 30 minutes at 0°C., the reaction mixture was worked up by extraction with ether (3 times), washing of the combined extracts with sodium bicarbonate solution and water, drying over sodium sulfate, filtration, and evaporation of the filtrate at 50°C. in vacuo to give rac. 19-nortestosterone as an oil. This material was chromatographed on silica gel (5.7 g.). Elution with benzene-ether (1:1) and benzene-ether (1:2) afforded rac. 19-nortestosterone which upon recrystallization from ether-hexane yielded rac. 19-nortestosterone melting at 116.5°–120°C.

EXAMPLE 81

31.05 g. of 6a,9a-trans-3-ethyl-6aβ-methylperhydrocyclopenta[f][1]benzopyran-4a,7-diol was dissolved in 490 ml. of acetone. A solution of chromium trioxide (32.4 g.) in 162 ml. of 6N sulfuric acid was then dissolved into the resultant solution with stirring at 20°C. (cooling with ice bath) during the course of 20 minutes. After stirring the reaction mixture for 2 hours at 20°C., 100 ml. of water was added. The reaction mixture was then extracted with 400 ml. of benzene and then twice, each time with 300 ml. of benzene. The benzene extracts were twice washed, each time with 200 ml. of water and the combined benzene extracts were then dried over sodium sulfate and evaporated to dryness at 45°C. in vacuo yielding 29.5 g. of 4-(3'-oxopentyl)-7aβ-methyl-3aα-perhydroinden-1,5-dione as a yellow oil. This was dissolved in 295 ml. of benzene and treated with 2.95 g. of para-toluene-sulfonic acid. This mixture was then refluxed for 3 hours, after which it was cooled to 20°C., washed twice, each time with 100 ml. of water, twice, each time with 100 ml. of saturated sodium bicarbonate solution, and twice again, each time with 100 ml. of water. The aqueous phases were twice re-extracted, each time with 150 ml. of benzene; the combined benzene extracts were dried over sodium sulfate. After evaporation to dryness at 45°C., crude desA-androst-9-en-15,17-dione was obtained as a brown oil. This crude product was then purified by column chromatography with aluminum oxide (265 g., active Grade III). The first three fractions were eluted with hexane-benzene (4:1) and contained predominantly desA-androst-9-en-5,17-dione; fractions 4–6 were eluted with hexane-benzene (1:1) and fractions 7–9 with benzene. These fractions contained purified desA-androst-9-en-5,17-dione. Fractions 4–9 were evaporated to dryness at 45°C. in vacuo and the residue was dissolved in isopropyl ether (5 ml.) and diluted with hexane until the solution became turbid. After seeding with desA-androst-9-en-5,17-dione, light beige crystals precipitated. The crystals were filtered off after a few hours at room temperature and washed with an equal amount of hexane-isopropyl ether (2:1) yielding, d,1-desA-androst-9-en-5,17-dione as yellow crystals melting at 100.5°–102.0°C.

EXAMPLE 82

Employing procedures similar to those described in Example 29 but substituting 3-methyl-6aβ-ethyl-1,2,3,5,6,6a-hexahydrocyclopenta[f][1]benzopyran-7(8H)-one for the 3-ethyl-6aβ-methyl-1,2,3,5,6,6a- hexahydrocyclopenta[f][1]benzopyran-7(8H)-one, there is produced 3-methyl-6aβ-ethyl-1,2,3,5,6,6a,7,8-octahydrocyclopenta[f][1]benzopyran-7-ol.

EXAMPLE 83

Employing apparatus and procedures similar to those described in Example 41 but substituting the product of Example 82 for that of Example 29, there is produced predominantly 6a,9a-trans-3-methyl-6aβ-ethyl-1,2,3,5,6,6a,7,8,9,9a-decahydrocyclopenta[f][1]benzopyran-7-ol.

EXAMPLE 84

Employing apparatus and procedures similar to those described in Example 41 but substituting the product of Example 39 for that of Example 29, there is produced predominantly 6a,9a-trans-3-ethyl-6aβ,7α-dimethyl-1,2,3,5,6,6a,7,8,9,9a-decahydrocyclopenta[f][1]benzopyran-7-ol.

EXAMPLE 85

Employing apparatus and procedures similar to those described in Example 58 but substituting the product of Example 40 for that of Example 41, there is produced predominantly 6a,9a-trans-3-ethyl-7α-ethynyl-6aβ-methylperhydrocyclopenta[f][1]benzopyran-4a,7-diol.

EXAMPLE 86

Employing apparatus and procedures similar to those described in Example 58 but substituting the product of Example 83 for that of Example 41, there is produced predominantly 6a,9a-trans-6aβ-ethyl-3-methylperhydrocyclopenta[f][1]benzopyran-4a,7-diol.

EXAMPLE 87

Employing apparatus and procedures similar to those described in Example 58 but substituting the product of Example 84 for that of Example 41, there is produced predominantly 6a,9a-trans-6aβ,7α-dimethyl-3-ethylperhydrocyclopenta[f][1]benzopyran-4a,7-diol.

EXAMPLE 88

Employing apparatus and procedures similar to those described in Example 76 but substituting the product of Example 59 for that of Example 58, there is prepared 3a,7a-trans-4-(3'-oxopentyl)-7aβ-ethylperhydroinden-1,5-dione which is then converted to 18-nor-13β-ethyl-desA-androst-9-en-5,17-dione.

EXAMPLE 89

Employing apparatus and procedures similar to those described in Example 76 but substituting the product of Example 60 for that of Example 58, there is prepared 3a,7a-trans-4-(3'-oxobutyl)-6aβ-methylperhydroinden-1,5-dione which is then converted to 19-nor-desA-androst-9-en-5,17-dione.

EXAMPLE 90

Employing apparatus and procedures similar to those described in Example 76 but substituting the product of Example 61 for that of Example 58, there is prepared 3a,7a-trans-4-(3'-oxohexyl)-7aβ-methylperhydroinden-1,5-dione which is then converted to 19-nor-10-ethyl-desA-androst-9-en-5,17-dione.

EXAMPLE 91

Employing apparatus and procedures similar to those described in Example 76 but substituting the product of Example 62 for that of Example 58, there is prepared 4a,8a-trans-5-(3'-oxopentyl)-8aβ-methylperhydronaphthalen-1,6-dione which is then converted to desA-D-homo-9-en-5,17-dione.

EXAMPLE 92

Employing apparatus and procedures similar to those described in Example 76 but substituting the product of Example 63 for that of Example 58, there is prepared 4a,8a-trans-5-(3'-oxopentyl)-7aβ-ethylperhydronaphthalen-1,6-dione which is then converted to 18-nor-13β-ethyl-desA-D-homoandrost-9-en-5,17-dione.

EXAMPLE 93

Employing apparatus and procedures similar to those described in Example 76 but substituting the product of Example 86 for that of Example 58, there is prepared 3a,7a-trans-4-(3'-oxobutyl)-7aβ-ethylperhydroinden-1,5-dione which is then converted to 18-nor-19-nor-13β-ethyl-desA-androst-9-en-5,17-dione.

EXAMPLE 94

Employing apparatus and procedures similar to those described in Example 76 but substituting the product of Example 87 for that of Example 58, there is prepared 3a,7a-trans-1β-hydroxy-4-(3'-oxopentyl)-1,7aβ-dimethylperhydroinden-5-one which is then converted to 17β-hydroxy-17α-methyl-desA-androst-9-en-5-one.

EXAMPLE 95

3-(4-oxopentyl)-1,2,3,5,6,6a-hexahydro-6aβ-methylcyclopenta[f][1]benzopyran-7(8H)-one (12 g.) is dissolved in 300 ml. of toluene and hydrogenated in the presence of 2.0 g. of 5% palladium-on-charcoal catalyst. During ca. 9 hour period 850 ml. of $H_2$ is consumed. The hydrogenation is performed at room temperature.

At the end of the reaction period the catalyst is removed by filtration, and the solvent removed in vacuo. The crude product is chromatographed on 120 g. of neutral alumina Grade III, and the column eluted with hexane-ether (1:2) giving a purified 6a,9a-cis-3-(4-oxopentyl)-1,2,3,5,6,6a,9,9a-octahydro-6aβ-methylcyclopenta[f][1]benzopyran-7(8H)-one.

EXAMPLE 96

A solution of 6a,9a-cis-3-(4-oxopentyl)-6aβ-methyl-1,2,3,5,6,6a,9,9a-octahydrocyclopenta[f][1]benzopyran-7(8H)-one (680 mg.) in tetrahydrofuran (30 ml.) is added at 0°C. within 15 minutes to a mixture of lithium aluminum hydride (131 mg.) in tetrahydrofuran (20 ml.), with stirring and under a nitrogen atmosphere. The reaction mixture is then stirred for an additional 30 minutes at 0°C. and then worked up by careful addition of water, filtration and evaporation of the filtrate in vacuo at 38°C. yielding crude 6a,9a-cis-3-(4-hydroxypentyl)-6aβ-methyl-1,2,3,5,6,6a,7,8,9,9a-decahydrocyclopenta[f][1]benzopyran-7-ol.

EXAMPLE 97

A solution of crude 6a,9a-cis-3-(4-hydroxypentyl)-6aβ-methyl-1,2,3,5,6,6a,7,8,9,9a-decahydrocyclopenta[f][1]-benzopyran-7-ol (760 mg., obtained by the procedure of Example 96) in pyridine (7.5 ml.) is treated with acetic acid anhydride (3.75 ml.) at room temperature. After standing at room temperature for 20 hours the reaction mixture is treated with methanol (12 ml.) at 0°C. After standing for 30 minutes it is then extracted with benzene (3 times), the combined benzene extracts are washed with $H_2O$, in HCl, saturated $NaHCO_3$ solution and again with $H_2O$. The benzene extract is then evaporated and the residue purified by chromatography on alumina (26.7 g.). Elution with hexane and hexaneether (9:1) affords 6a,9a-cis-7β-acetoxy-3-(4-acetoxypentyl)-6aβ-methyl-1,2,3,5,6,6a,7,8,9,9a-decahydro-cyclopenta[f][1]benzopyran.

EXAMPLE 98

A mixture of crude 6a,9a-cis-7β-acetoxy-3-(4-acetoxypentyl)-6aβ-methyl-1,2,3,5,6,6a,7,8,9,9a-decahydro-cyclopenta[f][1]-benzopyran (650 mg., obtained by the procedure of Example 97), acetone (15 ml.) and 1N sulfuric acid (7.5 ml.) is allowed to stand for 1 hour at room temperature. The workup by extraction with ether (3 times), washing of the combined extracts with sodium bicarbonate solution and water, drying over sodium sulfate, filtration, and evaporation of the filtrate at 50°C. in vacuo affords crude 6a,9a-cis-3-(4-acetoxypentyl)-7β-acetoxy-6aβ-methyl-perhydrocyclopenta[f][1]benzopyran-4a-ol, which is purified by chromatography on alumina (33.7 g.). Fractions (34 ml. each) are taken as follows: 1–3 = hexane-ether (9:1), 4–6 = hexane-ether (4:1), 7–9 = hexane-ether (2:1) and 10–12 = hexane-ether (1:1). The fractions containing 6a,9a-cis-3-(4-acetoxypentyl)-7β-acetoxy-6aβ-methylperhydrocyclopenta[f][1]benzopyran-4a-ol are identified by thin layer chromatography analysis.

EXAMPLE 99

To a solution of chromatographed 6a,9a-cis-3-(4-acetoxypentyl)-7β-acetoxy-6aβ-methylperhydrocyclopenta[f][1]benzopyran-4a-ol (500 mg.) in acetone (15 ml.), a mixture of chromic acid (500 mg.) in 6N sulfuric acid (2.65 ml.) is added at 20°C. (ice-cooling) with stirring during 5 minutes. After this addition, the mixture is stirred for another 2 hours at room temperature. The workup by extraction with ether (3 times), washing of the combined extracts with sodium bicarbonate solution and water, drying over sodium sulfate, filtration, and evaporation of the filtrate at 50°C. in vacuo affords crude 3a,7a-cis-4-(7-acetoxy-3-oxooctyl)-1β-acetoxy-7aβ-methyl-perhydroindan-5-one as an oil. This product is used for the next step.

A mixture of 3a,7a-cis-4-(7-acetoxy-3-oxooctyl)-1β-acetoxy-7aβ-methyl-perhydroindan-5-one (crude oxidation product; 470 mg.), benzene (10 ml.) and p-toluenesulfonic acid (47 mg.) is refluxed for 3 hours. Workup by extraction with ether (3 times), washing of the combined extracts with sodium bicarbonate solution and water, drying over sodium sulfate, filtration, and evaporation of the filtrate at 50°C. in vacuo gives crude 17β-acetoxy-10-(3-acetoxybutyl)-19-nor-14β-desA-androst-9-en-5-one which is purified by chromatography on silica gel (43.5 g.). Fractions (44 ml. each) were taken as follows: 1–3 = hexane-ether (4:1), 4–6 = hexane-ether (2:1), 7–9 = hexane-ether (1:1), 10–12 = hexane-ether (1:2) and 13–15 = hexane-ether (1:4). The fractions (242 mg.) containing 17β-acetoxy-10-(3-acetoxybutyl)-19-nor-14β-desA-androst-9-en-5-one are identified by thin layer chromatography analysis.

EXAMPLE 100

A solution of chromatographed 17β-acetoxy-10-(3-acetoxybutyl)-19-nor-14β-desA-androst-9-en-5-one (217 mg.) in absolute ethanol (15 ml.) and triethylamine (0.075 ml.) is hydrogenated under normal conditions using 5 per cent palladium-on-charcoal catalyst (27.5 mg.). The uptake (16 ml.) of hydrogen stops after about 5 hours. Workup by extraction with ether (3 times), washing of the combined extracts with sodium bicarbonate solution and water, drying over sodium sulfate, filtration, and evaporation of the filtrate at 50°C. in vacuo gives 17β-acetoxy-10-(3-acetoxybutyl)-19-nor-14β-desA-androstan-5-one as an oil. This crude product is used for the next step.

A mixture of crude 17β-acetoxy-10-(3-acetoxybutyl)-19-nor-14β-desA-androstan-5-one (217 mg.), ethanol (10 ml.) and 20 per cent sodium hydroxide solution (1.0 ml.) is allowed to stand at room temperature for 20 hours. Workup by extraction with ether (3 times), washing of the combined extracts with sodium bicarbonate solution and water, drying over sodium sulfate, filtration, and evaporation of the filtrate at 50°C. in vacuo affords crude 17β-hydroxy-10-(3-hydroxybutyl)-19-nor-14β-desA-androstan-5-one. This crude product is used for the next step.

To a solution of crude 17β-hydroxy-10-(3-hydroxybutyl)-19-nor-14β-desA-androstan-5-one (188 mg.) in acetone (7.5 ml.) a mixture of chromic acid (317 mg.) in 6N sulfuric acid (1.6 ml.) is added over a period of 10 minutes with stirring and ice-cooling (20°C.). After this addition the reaction mixture is stirred for another hour at room temperature. Workup by extraction with ether (3 times), washing of the combined extracts with sodium bicarbonate solution and water, drying over sodium sulfate, filtration, and evaporation of the filtrate at 50°C. in vacuo gives crude 10-(3-oxobutyl)-19-nor-14β-desA-androstan-5,17-dione which is purified by chromatography on silica gel (15 g.). Elution with benzene-ether (2:1) and then with benzene-ether (1:1) gives the desired product 10-(3-oxobutyl)-19-nor-14β-desA-androstan-5,17-dione.

EXAMPLE 101

A mixture of 10-(3-oxobutyl)-19-nor-14β-desA-androstan-5,17-dione (chromatographed product; 48.3 mg.), toluene (2 ml.) and p-toluenesulfonic acid (4.8 mg.) is refluxed for 3 hours. Workup by extraction with ether (3 times), washing of the combined extracts with sodium bicarbonate solution and water, drying over sodium sulfate, filtration, and evaporation of the filtrate at 50°C. in vacuo gives crude 19-nor-14β-androst-4-en-3,17-dione. This material is purified by chromatography on silica gel (4.4 g.). Elution with benzene-ether (1:1) affords 19-nor-14β-androst-4-en-3,17-dione (33.6 mg.).

To a stirred solution of 19-nor-14β-androst-4-en-3,17-dione (28.4 mg.; chromatographed product) in tetrahydrofuran (1.3 ml.), tri-tert.-butoxylithium aluminum hydride (53 mg.) is added at 0°C. in one portion. After stirring for 30 minutes at 0°C., the reaction mixture is worked up by extraction with ether (3 times), washing of the combined extracts with sodium bicarbonate solution and water, drying over sodium sulfate, filtration, and evaporation of the filtrate at 50°C. in vacuo to give rac. 19-nor-14β-testosterone as an oil. This material is chromatographed on silica gel (2.8 g.). Elution with benzene-ether (1:1) and benzene-ether (1:2) affords rac. 19-nor-14β-testosterone.

EXAMPLE 102

6a,9a-trans-3-[4,4-(ethylenedioxy)pentyl]-6aβ-methylperhydrocyclopenta[f][1]benzopyran-4a,7β-diol (1.2 g.) was dissolved in acetone (12 ml.) and this solution was added within 15 minutes to a solution of chromic acid (1.0 g.) in dimethylformamide (20 ml.) containing 1N sulfuric acid (2ml.). The reaction mixture was then stirred for 5 hours at room temperature, poured onto ice and extracted 3 times, each time with 100 ml. of ether. After washing with water and sodium bicarbonate solution, the ether extracts were combined, dried over sodium sulfate, filtered and evaporated to dryness in vacuo at 35°C. yielding crude 3a,7a-trans-4-[7,7-(ethylenedioxy)-3-oxooctyl]-7aβ-methyl-perhydroindan-1,5-dione.

The so-obtained crude 3a,7a-trans-4-[7,7-(ethylenedioxy)-3-oxooctyl]-7aβ-methyl-perhydroindan-1,5-dione was cyclized by refluxing it in a solution of methanol (50 ml.) containing 5 ml. of 3N sodium hydroxide. The reaction mixture was then stirred for 5 hours at room temperature, poured onto ice and extracted 3 times, each time with 100 ml. of ether. After washing with water and sodium bicarbonate solution, the ether extracts were combined, dried over sodium sulfate, filtered and evaporated to dryness in vacuo at 35° yielding crude 10-[3,3-(ethylenedioxy)butyl]-19-nor-desA-androst-9-en-5,17-dione. This product, which exhibited a UV-absorption at 248 mμ (in ethanol) was purified by column chromatography on alumina (30 g.; Grade III).

EXAMPLE 103

A solution of optically active 3-ethyl-6aβ-methyl-1,2,3,5,6,6a-hexahydrocyclopenta[f][1]benzopyran-7(8H)-one (1.053 g.; chromatographed) in tetrahydrofuran (25 ml.; passed through a column of alumina) was added at 0°C. within 15 minutes to a mixture of lithium aluminum hydride (105.3 mg.) in tetrahydrofuran (30 ml.; passed through a column of alumina), with stirring and under a nitrogen atmosphere. The reaction mixture was then stirred for an additional 30 minutes at 0°C. and then worked up by careful addition of water, filtration and evaporation of the filtrate in vacuo at 38° yielding crude optically active 3-ethyl-6aβ-methyl-1,2,3,5,6,6a,7,8-octahydrocyclopenta[f][1]benzopyran-7-ol (1.0 g.). Thin layer chromatography analysis (silica gel plates, solvent benzene-ethylacetate 1:1, detection 50 per cent aqueous p-toluenesulfonic acid solution, 120°C. for 15 minutes, then iodine at room temperature) showed one major spot plus traces of starting material. The crude was then purified by chromatography on alumina (30 g.). Elution with hexane-ether (9:1) and (4:1) afforded a total of 760 mg. pure optically active 3-ethyl-6aβ-methyl-1,2,3,5,6,6a,7,8-octahydrocyclopenta[f][1]benzopyran-7-ol. The best fraction (No. 9) had a rotation of $[\alpha]_D^{25}$ −147.3° (c = 1.0; CHCl$_3$).

EXAMPLE 104

A solution of optically active 3-ethyl-6aβ-methyl-1,2,3,5,6,6a,7,8-octahydrocyclopenta[f][1]benzopyran-7-ol (700 mg.; chromatographed) in toluene (30 ml.) was hydrogenated under normal conditions using a 5 per cent palladium-on-charcoal catalyst (70 mg.). The uptake (80 ml.) of hydrogen stopped after about 10 hours. The catalyst was filtered off and washed with toluene. After evaporation crude optically active 6a,9a-trans-3-ethyl-6aβ-methyl-1,2,3,5,6,6a,7,8,9,9a-decahydrocyclopenta[f][1]benzopyran7-ol (700 mg.) was obtained. Thin layer chromatography analysis showed one major spot plus several minor spots. This crude product was used for the next step.

A mixture of crude optically active 6a, 9a-trans-3-ethyl-6aβ-methyl-1,2,3,4,5,6,6a,7,8,9,9a-decahydrocyclopenta[f][1]benzopyran-7-ol (700 mg.; prepared as above), acetone (14 ml.) and 1N sulfuric acid (7 ml.) was allowed to stand for 1 hour at room temperature. Extraction with ether or benzene (3 portions), washing with sodium bicarbonate solution and water, drying over sodium sulfate, filtration and evaporation to dryness at 45°C. in vacuo afforded crude optically active 6a, 9a-trans-3-ethyl-6aβ-methylperhydrocyclopenta[f][1]benzopyran-4a,7-ol (672 mg.). Thin layer chromatography analysis (silica gel plates, solvent benzene-ethylacetate 1:1, detection 50 per cent aqueous p-toluenesulfonic acid solution, 120°C. for 15 minutes, then iodine at room temperature) showed one major spot plus several minor spots. This crude product was used for the next step.

To a solution of crude optically active 6a, 9a-trans-3-ethyl-6aβ-methylperhydrocyclopenta[f][1]benzopyran-4a,7-ol (672 mg.; prepared as above) in actone (30 ml.), a mixture of chromic acid (1.32 g.) in 6N sulfuric acid (6.6 ml.) was added at 20°C. with stirring, during 10 minutes. After this addition was completed, the mixture was stirred for another 2 hours at room temperature. Extraction with ether or benzene (3 portions), washing with sodium bicarbonate solution and water, drying over sodium sulfate, filtration and evaporation to dryness at 45°C. in vacuo afforded crude optically active 4-(3'-oxopentyl)-7aβ-methyl-3aαperhydroinden-1,5-dione 9525 mg.). Thin layer chromatography analysis showed one major spot plus two minor spots. This crude product was used for the next step.

A mixture of optically active 4-(3'-oxopentyl)-7aβ-methyl3aα-perhydroinden-1,5-dione (crude oxidation product prepared as above; 525 mg.), toluene (30 ml.) and p-toluenesulfonic acid (139 mg.) was refluxed for 3 hours. Extraction with ether or benzene (3 portions), washing with sodium bicarbonate solution and water, drying over sodium sulfate, filtration and evaporation to dryness at 45°C. in vacuo gave crude optically active desA-androst-9-en-5,17-dione (433 mg.). This crude product was purified by chromatography on silica gel (13.0 g.). Fractions (13 ml. each) were taken as follows: 1–5 = hexane-ether (1:1), 6–10 = hexane-ether (1:2), 11–15=hexane-ether (1:4) and 16–18 straight ether. Fractions 9–16 yielded a total of 320 mg. of optically active desA-androst-9-en-5,17-dione. Fractions 9 and 10 (159 mg.) were recrystallized from ether-hexane to give optically active desA-androst-9-en-5,17-dione melting at 100°–102°, $[\alpha]_D^{25}$ + 27.3°(c=1.0; CHCl$_3$).

To a stirred solution of optically active desA-androst-9-en-5,17-dione (320 mg.; chromatographed) in tetrahydrofuran (14 ml.), tri-tert.-butoxy lithium hydride (631 mg.) was added at 0°C. in one portion. After stirring for 45 minutes at 0°C., the reaction mixture was worked up by extraction with ether or benzene (3 portions), washing with sodium bicarbonate solution and water, drying over sodium sulfate, filtration and evaporation to dryness at 45°C. in vacuo giving crude optically active 17β-hydroxy-desA-androst-9-en-5-one (320 mg.) which was purified by chromatography on alumina (32 g.). Fractions (32 ml. each) were taken as follows: 1–3 = hexane-benzene (1:1), 4–6 = hexane-benzene (1:4), 7–9 = straight benzene, 10–12 = benzene-ether (9:1), 13–15 = benzeneether (4:1) and 16–18 = straight ether. Fractions 10–15 yielded optically active 17β-hydroxy-des--androst-9-en-5-one. This material was dissolved in methanol (10 ml.) and treated at 25°C. with 20 per cent aqueous NaOH solution (2.0 ml.) for 15 hours. After extraction with ether or benzene (3 portions), washing with sodium bicarbonate solution and water, drying over sodium sulfate, filtration and evaporation to dryness at 45°C. in vacuo crude optically active 17β-hydroxy-desA-androst-9-en-5-one was obtained which was again purified by chromatography on alumina as described above. Fractions 8–11 yielded optically active 17β-hydroxy-desA-androst9-en-5-one. This material was then recrystallized from benzenehexane to give white crystals of optically active 17β-hydroxydesA-androst-9-en-5-one, which was recrystallized from benzene, m.p. 165°–168°, $[\alpha]_D^{25}$ −44.2° (c= 0.50; CHCl$_3$).

EXAMPLE 105

70 G. of 2,3-butanediol was refluxed with 78.0 g. of 1-chloro-4-pentanone dissolved in 780 ml. of benzene to which 1.5 g. of p-toluenesulfonic acid was added. The butanediol was found by NMR analysis to be a mixture of meso and racemic forms in a ratio of 2:3 respectively. Therefore, the butylenedioxy protective moiety comprises a mixture of isomers. The reaction mixture was refluxed for 90 minutes yielding the chloro-ketal, 1-chloro-4-[(2',3')-butylenedioxy]-pentane. The product was obtained by distillation employing a Vigreaux column and consisted of a mixture of the meso and racemic isomers.

EXAMPLE 106

41.25 G. of the product 1-chloro-4-[(2',3')-butylenedioxy]-pentane of Example 105 was dissolved in 400 ml. of tetrahydrofuran at 62°–65°. The tetrahydrofuran was freshly filtered through a bed of alumina, activity 1, neutral before use. To this solution was added 5.85 g. of magnesium metal activated with 1 crystal of iodine and 2 drops of bromoethane and a solution of 18.05 g. of glutaraldehyde in 180 ml. of tetrahydrofuran at 0°. The glutaraldehyde was extracted from a 25 per cent aqueous solution with methylene chloride solution, evaporated and dried over sodium sulfate before addition to the reaction. The reaction mixture was agitated at 25° for 2 hours and then decanted onto ice and ammonium chloride. The product work-up proceeded by multiple extraction with 3 portions of benzene and washing the combined extracts with a solution of sodium bicarbonate and water. The organic phase was then dried over anhydrous sodium sulfate and evaporated in vacuo at 35°–40° giving 55.60 g. of the crude yellow oil, 6-[4,4-(2',3'butylenedioxy)-pentyl]-2-tetrahydropyranol.

EXAMPLE 107

45 G. of the crude lactol 6-[4,4-(2',3'-butylenedioxy)-pentyl]-2-tetrahydropyranol prepared in the previous Example was added to 250 ml. of 20 percent aqueous sodium sulfite solution at 25°. The pH was adjusted to 6.5 by adding glacial acetic acid and then made slightly at alkaline to a pH of 7.5 employing 1 normal sodium hydroxide. After stirring for one hour, the mixture was extracted 3 times with 50 ml. each of ether, and the extraction procedure was repeated employing water. The aqueous extracts were combined and added to 40 ml. of benzene thus forming a two-phase system, while the pH was adjusted to 12.0 using 20 per cent aqueous sodium hydroxide with rapid stirring. The organic phase is worked up by extraction with three portions of benzene, washing with a solution of water and sodium bicarbonate, drying over sodium sulfate, filtration and evaporation in vacuo at 35°–40° affording 28.5 g. of a yellow oil which showed one spot on thin layer chromatographic analysis. The structure was found to be compatible with 6-[4,4-(2',3'-butylenedioxy)-pentyl]-2-tetrahydropyranol by infrared analysis.

EXAMPLE 108

The product 3,7-dihydroxy-11,11-(2',3')-butylenedioxydodec-1-ene is obtained by adding to 145 ml. of a 21 per cent solution of vinyl magnesium chloride (based on the magnesium ions present) in tetrahydrofuran, 28.5 g. of 6-[4,4(2',3'-butylenedioxy)-pentyl]-2-tetrahydropyranol, which is dissolved in 285 ml. of tetrahydrofuran solution at 25° over a period of 15 minutes. After stirring for 12 hours at 25°, the reaction mixture was poured onto an ice-ammonium chloride mixture and then extracted with three portions of benzene, washed with a solution of water and saturated sodium bicarbonate. The organic phase was then dried over sodium sulfate, filtered, and evaporated in vacuo at 35°. Upon evaporation, 33 g. of 3,7-dihydroxy-11,11-(2',3')-butylenedioxy-dodec-1-ene were produced in the form of an oil which showed on spot using thin layer chromatography.

EXAMPLE 109

The product 2-92'-diethylaminoethyl)-6-[4,4-(2',3')-butylenedioxy-pentyl]-2-tetrahydropyranol is obtained by treating 10 g. of 3,7-dihydroxy-11,11-(2',3') butylenedioxy-dodec-1-ene obtained in Example 108 with 50 g. of manganese dioxide in a solution of 300 ml. of benzene and 78 ml. of diethylamine at 75° for 1 hour. The product obtained was found to be uniform by thin layer chromatography.

EXAMPLE 110

12.4 G. of 2-(2'-diethylaminoethyl)-6-[4,4-92',3')-butylenedioxy-pentyl]-2-tetrahydropyranol obtained in Example 109 was refluxed with 4 g. of 2-methyl-1,3-cyclopentanedione in a solution of 400 ml. of a 1 to 1 mixture of xylene and toluene to which 125 ml. of glacial acetic acid was added. The refluxing continued for 1 hour yielding 12.2 g. of crude 3-[4,4-(2',3')-butylenedioxy-penty]-6aβ-methyl-1,2,3,5,6,6a-hexahydrocyclopenta [f][1]benzopyran-7(8H)-one. This product was purified by column chromatography on alumina oxide (600g., grade III). Elution with a hexane-ether mixture (9:1) and evaporation in vacuo at 35°afforded 6.5 g. of a pure 3-[4,4-(2',3')-butylenedioxy-pentyl]-6aβ-methyl-1,2,3,5,6,6a -hexahydrocyclopenta[f][1]benzopyran-798H)-one.

EXAMPLE 111

6.4 G. of the dienolether 3-[4,4-(2',3')-butylenedioxypentyl]-6aβ-methyl-1,2,3,5,6,6a-hexahydrocyclopenta[f][1]benzopyran-7(8H)-one produced in Example 110 was dissolved into 100 ml of tetrahydrofuran. This solution was added cautiously to a suspension of a mixture of 1.3 g. of lithium aluminum hydride. suspended in 110 ml of tetrahydrofuran at 0°. The reaction which is exothermic was maintained at 0°C. by means of immersion in a bath which was kept at −15°C. 10 Ml. of water was then added to destroy the excess of the hydride after two hours at 0°. The resulting gelatinous precipitate was then filtered off and washed with tetrahydrofuran and ether solution to recover any product which may have adhered to the precipitate. The washings were combined with the filtrate which was then dried over sodium sulfate and evaporated affording product 3-[4,4-(2′,3′)-butylenedioxy-pentyl]-6a$\beta$-methyl-1,2,3,5,6,6a,7,8-octahydrocyclopenta[f][1]-benzopyran-7-ol.

EXAMPLE 112

By means of selective catalytic hydrogenation, 3-[4,4-92′,3′)-butylenedioxy-pentyl]-6a$\beta$-methyl-1,2,3,5,6,6a, 7,8-octahydrocyclopenta[f][1]benzopyran-7-ol produced in Example 111 above, was converted into 3-[4,4-92′,3′)-butylenedioxy-pentyl]-6a$\beta$-methyl-1,2,3,5,6,6a,7,8,9,9a-decahydrocyclopenta[f][1]benzopyran-7-ol. 3-[4,4-(2′,3′)-butylenedioxypentyl]-6a$\beta$-methyl-1,2,3,5,6,6a,7,8,9,9a-decahydrocyclopenta[f][1]benzopyran-7-ol was suspended in toluene to which a 5 per cent carbon catalyst was added. The hydrogen utake was completed in 3 hours. 200 Ml. of toluene were used per 6.5 g. of 3-[4,4-(2′,-3′)-butylenedioxy-pentyl]-6a$\beta$-methyl-1,2,3,5,6,6a,7,8-octahydrocyclopenta[f][1]benzopyran7-ol. The crude product was produced after washing of the catalyst, filtration and evaporation of the solvent. Purification was effected by column chromatography using 300 g. of alumina grade III. Fractions 5–10 which afforded the pure product as identified by thin layer chromatography was taken as follows 5–6 = hexane-ether (4:1); 7–10 = hexane-ether (2:1).

EXAMPLE 113

2.96 G. of 3-[4,4-92′,3′)-butylenedioxy-pentyl]-6a$\beta$-methyl-1,2,3,5,6,6a,7,8,9,9a-decahydrocyclopenta[f][1]benzopyran-7-ol produced in Example 112, was dissolved in 222 ml. of dioxane at 25°. 68 Ml. of 0.1 normal sulfuric acid was added to this solution and after 90 minutes, the reaction mixture was extracted with benzene (3 times), washed with a sodium bicarbonate water mixture, dried over sodium sulfate, filtered and evaporated to dryness at 35°in vacuo. The crude product thus produced was purified by column chromatography on alumina (162 g., Grade III), elution with hexane-ether (2:1) yielding 6a, 9a-trans3-[4,4-92′,3′)-butylenedioxy-pentyl]-6a$\beta$-methyl-perhydrocyclopenta [f][1]benzopyran-4a, 7-diol.

EXAMPLE 114

1.82 G. of 6a, 9a-trans-3-[4,4-(2′,3′)-butylenedioxypentyl]-6a$\beta$-methyl-perhydrocyclo-penta [f][1]benzopyran-4a,7-diol was dissolved in 55 ml. of acetone at 10°. To this solution was added 4.75 ml. of 3normal sulfuric acid containing 1.00 g. of chromium trioxide. The reaction mixture was stirred for 1 hour at 5°. Work-up by extraction with benzene (3 times), washing with a water and sodium bicarbonate solution, drying over sodium sulfate, filtration and evaporation of the filtrate in vacuo at 35° afforded crude 6a,9a-trans-3-[4-oxopentyl]-6a$\beta$-methyl-7-oxo-perhydrocyclopenta [f][1]benzopyran-4a-ol which was isolated as a syrup. The product was purified by column chromatography eluting with: fractions 1–3 = benzene; 4–6 = benzene-ether (9:1); 7–11 = benzene-ether (4:1); 12–14 = benzene-ether. The desired product was obtained in fractions 7–12 and identified by thin layer chromatography to be 6a,9a-trans-3-[4,4-(2′,3′)-butylenedioxy-pentyl]-6a$\beta$-methyl-7-oxo-perhydrocyclopenta[f][1benzopyran-4a-ol.

To a solution of 6a,9a-trans-3-[4,4-(2′,3′)-butylenedioxypentyl]-6a$\beta$-methyl-7-oxo-perhydrocyclopenta [f][1]benzopyran 4a-ol dissolved in 30 ml. of acetone at 10° was added a solution of 675 mg. of chromium trioxide and 3.5 ml. of 6 normal sulfuric acid. After stirring for one hour at 5°, the reaction mixture was extracted with benzene 93 times), washed with a water and sodium bicarbonate solution, dried over sodium sulfate, filtered and evaporated in vacuo at 35°affording a crude syrup, which is purified by chromatography on alumina (110 g., activity Grade III). Fractions were taken as follows: 1–3 = benzene; 4–8 = benzene-ether (9:1); 9–11 = benzene-ether (4:1); 12–14 = benzeneether (2:1). After evaporation, thin layer chromatographic analysis showed fractions 5–7 to be 3a,7a-trans-4-[3′-oxo-7′,7′-)2,3)-butylenedioxyoctyl]-7a$\beta$-methyl-perhydro-indan-1,5-dione.

EXAMPLE 115

400 Mg. of 3a, 7a-trans-4-[3′-oxo-7′,7′-92,3)-butylenedioxy-octyl]-7a$\beta$-methyl-perhydro-indan-1,5-dione produced in Example 114, is heated at 50°for one hour in the presence of 8 ml. of distilled tertiary butyl alcohol and 400 ml. of sodium hydroxide. The sodium hydroxide was pulverized and added rapidly to the tertiary butyl alcohol at 25°. All solids were powdered under the liquid surface and dissolved air was removed by alternate evacuation and replacement of the atmosphere in the flask with dry nitrogen. Starting material was added under a nitrogen atmosphere which was also the condition in which the reaction was performed. The reaction mixture was neutralized with two drops of acetic acic and extracted with benzene 93 times), washed with a water and sodium bicarbonate solution, dried over sodium sulfate, filtered and evaporated in vacuo at 35° affording crude 10-[3,3-92′,3′)-butylenedioxy-butyl]-19-nor-desA-androst-9-en-5,17-dione. This crude product was purified by chromatography on silica gel (37.0 g.) Fractions were taken as follows: 1–5 = hexane-ether (1:1); 6–10 = hexane-ether (1:2); 11–15 = hexaneether (1:4); 16–20 = hexane-ether (1:9); 21–25 = ether. Thin layer chromatography showed fractions 11–15 to be 10-[3,3-(2′,3′)-butylenedioxy-butyl]-19-nor-desA-androst-9-en-5,17-dione.

EXAMPLE 116

205 Mg of 10-[3,3-(2′,3′)-butylenedioxy-butyl]-19-nor-desA-androst-9-en-5,17-dione produced in Example 115, is dissolved in 15 ml. of absolute ethanol and 0.06 ml. of triethylamine employing a 5 per cent palladium on carbon catalyst (40 mg.). The reaction mixture is exposed to hydrogen gas under constant agitation for 5 hours at 25°. After filtration, removal of the catalyst by washing and evaporation to dryness, 10-[3,3-92′,3′)-butylenedioxy-butyl]-19-nor-desA-androstan-5,17-dione was identified by thin layer chromatographic analysis.

EXAMPLE 117

200.3 Mg of 10-[3,3-(2′,3′)-butylenedioxy-butyl]-19-nordesA-androstan-5,17-dione produced in Example 116 was dissolved in 2.5 ml. of absolute methanol and 2.5 ml. of 4 normal hydrochloric acid. The reaction mixture was allowed to reflux for three hours and after extraction with benzene (3 times), washing with a water and saturaated sodium bicarbonate solution, drying over sodium sulfate, filtering the solution and evaporating in vacuo at ⅝¾°, a semi-crude, semi-solid product 19-nor-androst-4-en-3,17-dione was formed. the product was purified by chromatography on silica gel. Fractions were taken as follows: 1–3 = benzene-ether (9:1); = benzene-ether (4:1); 7–9 = benzene-ether (2:1); 10–12 = benzene-ether (1:1); 13–15 = benzeneether (1:4). 19-Nor-androst-4-en-3,17-dione was isolated from fractions 9–11 by solvent evaporation. Recrystallization from ether-hexane affords 85.3 mg. of the pure compound, m.p. 157°–158°, UV: $\lambda_{max}^{ETOH}$ m$\epsilon(\epsilon)$ = 240 (18,000), Analysis — Theory — C — 79.48, H — 8.89; Found — C — 79.44, H — 8.76.

EXAMPLE 118

71.5 G. of 5-chloro-2-pentanone was dissolved in 250 ml. of ether and added to the slurry of 12 g. of lithium aluminum hydride at −40° over a 50 minuted period. The reaction mixture was agitated for an additional one-half hour at −30° and then a saturated aqueous solution of sodium sulfate (115 ml.) was added. The solids were then filtered off and washed with ether. Subsequent removal of the ether in vacuo yielded 5-chloro-2-pentanol.

EXAMPLE 119

238 G. of 5-chloro-2-pentanol produced in Example 118, was dissolved in 500 ml. of methylene chloride which was then added to a mixture of 24 ml. of concentrated sulfuric acid in 500 ml. of methylene chloride. 1 Liter of liquid isobutylene was then added and the mixture was allowed to stand at room temperature for 20 hours. The organic phase was washed with brine, aqueous sodium bicarbonate solution and dried over magnesium sulfate. Removal of the solvents in vacuo gave 5-chloro-2-tertiaryboxy-pentane.

EXAMPLE 120

10 G. of magnesium metal was activated with a crystal of iodine employed in vapor form and then the metal was covered with dry tetrahydrofuran (20 ml.). Five drops of dibromoethane was then added to the ether solution and the mixture was stirred at reflux for 15 minutes. 5-Chloro-2-tertiarybutoxy-pentane was then added to the reaction mixture in two stages as follows:

To initiate the reaction, 20 ml. of the chloro ether containing 63.5 g./250 ml. was added to the reaction mixture. After the reaction was underway (which can vary from between 15 minutes to 24 hours), the remainder of the solution consisting of 230 ml. was added over a period of 1 hour. The reaction mixture was then heated under reflux for an additional hour, cooled and filtered free of solids.

The above Grignard solution was added to a solution of 39 g. of gluteraldehyde, freshly distilled in tetrahydrofuran (400 ml.) at −25°. After agitating for an additional 15 minutes at −25°, the reaction was kept at 0°C. for 1 hour. 650 ml. of a 20 per cent aqueous ammonium chloride solution was then added and the pH was adjusted to 4 with a 100 ml. of 1 normal dilute hydrochloric acid. Extraction with ether gave 91 g. of a crude oil, the hemiacetal, 6-[4-tertiarybutoxypentyl]-2-tetrahydropyranol. The crude product was purified by stirring with 650 ml. of a 20 per cent solution of sodium sulfite and the pH was adjusted to 6.5 with glacial acetic acid. The pH was then readjusted to 7.5 by means of 20 per cent aqueous sodium hydroxide. After further agitation for one hour at 40°, the reaction mixture was extracted with ether. The aqueous layer was then adjusted to a pH of 12.5 with aqueous 20 per cent sodium hydroxide and again extracted with ether. Evaporation of the ether in vacuo gave the pure hemiacetal liquid, 6-[4-tertiarybutoxypentyl]-2-tetrahydropyranol.

EXAMPLE 121

4.5 G. of 6-[4-tertiarybutoxypentyl]-2-tetrahydropyranol produced in Example 120 was dissolved in 200 ml. of tetrahydrofuran and added slowly over a 20 minute period to a solution of 300 ml. of vinyl magnesium chloride in tetrahydrofuran at 0°. After agitation for an additional hour at room temperature, 200 ml. of ether was added which was followed by the addition of 100 ml. of a 20 per cent aqueous solution of ammonium chloride. Extraction with ether yielded a waxy solid, 3,7-dihydroxy-11-tertiarybutoxydodec-1-ene.

EXAMPLE 122

41.3 G. of 3,7-dihydroxy-11-tertiarybutoxy-dodec-1ene produced in Example 121 was dissolvedinbenzenesolutionandaddedtoaslurry of320 g. of activated manganese dioxide in 1600 ml. of benzene containing 120 ml. of diethylamine. The reaction mixture was stirred at room temperature for 20 hours and filtered free of solids. Removal of the solvents in vacuo gave a pale brown oil. The oil was dissolved in ether and extracted with aqueous 1N hydrochloric acid. Sodium hydroxide was added to the acid extract. Extraction into ether and evaporation of the solvent affords 2-[2'-diethylaminoethyl]-6-[4-t-butoxypentyl]-2-tetrahydropyranol.

EXAMPLE 123

To a refluxing solution of 22 grams of 2-ethyl-cyclopentane-1,3-dione in a solution of 440 ml. of xylene containing 220 ml. of acetic acid, was added 42.2 g. of the Mannich base 2-[2'-diethylaminoethyl]-6-[4-tertiarybutoxy-pentyl]-2-tetrahydropyranol. The mixture was heated at reflux for 1 hour, then cooled to room temperature and washed free of acetic acid by means of water. The solvents were removed in vacuo to yield crude 3-[4-tertiarybutoxy-pentyl]-6aβ-ethyl-1,2,3,5,6,6a-hexahydrocyclopenta[[f][1]benzopyran-7(8H)-one, which was present as a pale red oil. 38.8 G. of the pure material was obtained by means of chromatography on 1.2 kilograms of alumina (grade III, neutral).

EXAMPLE 124

3-[4-tertiarybutoxy-pentyl]-6aβ-ethyl-1,2,3,5,6,6a-hexahydrocyclopenta[f][1]benzopyran-7(8H)-one obtained in Example 123 was subjected to a reduction process wherein 3-[4-tertiarybutoxy-pentyl]-6aβ-ethyl-1,2,3,5,6a,7,8-octahydrocyclopenta [f][1]benzopyran-ol was produced. This consisted of adding a solution of 8.6 g. of 3-[4tertiarybutoxy-pentyl]-6aβ-ethyl-1,2,3,5,6,6a-hexahydrocyclopenta [f][1] benzopyran-7(8H)-one in 80 ml. of ether to a solution of 4 g. of a slurry of lithium aluminum hydride in 200 ml. of ether at −10°. After stirring for 1 hour at room temperature, 20 ml. of a saturated solution of sodium sulfate was added. The solids were then filtered off and washed with 150 ml. of ether. Removal of the solvents in vacuo gave 3-[4-tertiarybutoxy-pentyl]-6aβ-ethyl-1,2,3,5,6,6a,7,8-octahydrocyclopenta [f][1]benzopyran-7-ol. Purification by crystallization from hexane yielded the pure alcohol having a melting point of 71°–74°.

EXAMPLE 125

5.3 G. of 3-[4-tertiarybutoxy-pentyl]-6aβ-ethyl-1,2,3,5,6,6a,7,8-octahydrocyclopenta-[f][1]-benzopyran-7-ol produced in Example 124 was dissolved in 100 ml. of toluene containing 1.5 g. of a palladium-carbon catalyst and hydrogenated at atmospheric pressure and room temperature until no further hydrogen was consummed. This point occurred after 1.05 moles of hydrogen were consummed. The solids were then filtered off and the solvents removed in vacuo to furnish the oily enol ether, 6a,9a-trans-3-[4-tertiarybutoxy-pentyl]-6aβ-ethyl-1,2,3,5,6,6a,7,8,9,9a-decahydrocyclopenta[f][1]benzopyran-7-ol. This was shown to be a pure product by means of a thin layer chromatography using F 254 silica plates for the analysis.

EXAMPLE 126

35.9 G. of 6a,9a-trans-3-[4-tertiarybutoxy-pentyl]-6aβ-ethyl-1,2,3,5,6,6a,7,8,9,9a-decahydrocyclopenta[f][1]benzopyran-7-ol produced in Example 125 was dissolved in a solution of 700 ml. of acetone and treated with 200 ml. of 3 normal aqueous sulfuric acid. This mixture was allowed to stand at room temperature for two days. Dilution with brine, and extraction into ether and evaporation of the solvent in vacuo furnished a mixture of compounds 6a,9a-trans-3-[4-tertiarybutoxy-pentyl]-6aβ-ethylperhydrocyclopenta[f][1]benzopyran- 4a,7-diol, and 3a,7a-trans-4-[7'-tertiarybutoxy-3'-hydroxy-octyl]-7aβ-ethyl-perhydroindan-1,5-dione.

EXAMPLE 127

4.65 G. of crude mixture obtained in Example 126 was dissolved in 200 ml. of acetone and treated with 10 ml. of Jones chromic acid solution and stirred for 30 minutes at room temperature. The reaction mixture was diluted with brine and was isolated by extraction in ether. Removal of the solvent in vacuo gave 3a,7a-trans-4-[7'-tertiarybutoxy-3'-oxo-octyl]-7aβ-ethyl-perhydroindan-1,5-dione, as an oil which showed one spot on thin layer chromatographic analysis.

EXAMPLE 128

25.4 G. of 3a,7a-trans-4-[7'-tertiarybutoxy-3'-oxo-octyl]-7aβ-ethyl-perhydroindan-1,5-dione obtained in Example 127 was dissolved in 70 ml. tertiarybutyl alcohol and added to 250 ml. of tertiary butyl alcohol to which was added 1 g. of powdered sodium hydroxide. The reaction mixture was placed under a nitrogen atmosphere at 55°. After stirring at this temperature for 1 hour, the mixture was cooled, treated with brine and extracted into ether. Upon removal of the solvents in vacuo, and chromatography on neutral grade III alumina furnished pure diketone 10-[3-tertiarybutoxybutyl]-18-methyl-19-nor-desA-androst-9-en-5,17-dione.

EXAMPLE 129

The diketone, 10-[3-tertiary-butoxy-butyl]-18-methyl-19-nor-desA-androst-9-en-5,17-dione, produced in Example 128 was dissolved in 50 ml. of ethanol. 0.3 Ml. of triethylamine and 100 milligrams of a 5 percent palladium-carbon catalyst was then added to this solution. The reaction mixture was then hydrogenated at room temperature and pressure until hydrogen consumption ceased. The solids were filtered off and the solvents removed in vacuo to yield the saturated diketone, 10-[3-tertiary-butoxy-butyl]-18-methyl-19-nor-desA-androstan-5,17-dione, which showed only one spot on thin layer chromatography analysis.

EXAMPLE 130

500 Mg. of the diketone, 10-[3-tertiary-butoxybutyl]-18-methyl-19-nor-desA-androstan-5,17-dione was dissolved in 25 ml. of benzene containing a trace of p-toluenesulfonic acid (25 mg.) and the reaction mixture was heated under reflux for 2½ hours. The organic phase was washed free of acid and the solvent evaporated in vacuo. The crude residue was dissolved in 35 ml. acetone and treated with 15 ml. of 1 N aqueous sulfuric acid. After standing at room temperature for 35 minutes, the solution was diluted with brine, extracted with ether affording the waxy hemiketal, 6a,9a-trans-2-methyl-6aβ-ethyl-7-oxo-perhydrocyclopenta-[5,6]-naphtho-[2,1-b]-pyran-11a-ol. Further purification by crystallization from hexane gave pure product, m.p. 114°–116°.

EXAMPLE 131

750 Mg. of the hemiketal 6a,9a-trans-2-methyl-6aβ-ethyl-7-oxo-perhydrocyclopenta[5,6]naphtho-[2,1-b]-pyran-11a-ol produced in Example 130 was dissolved in 30 ml. of acetone. 1.26 G. of a solution of chromium trioxide which was dissolved in 6.5 ml. of 6 normal sulfuric acid, was added to the acetone mixture over a period of 10 minutes at room temperature and then agitated for one hour. The reaction mixture was diluted with brine and after extraction with ether and removal of the solvent in vacuo, an oil was produced. The oil was purified by chromatography on silica gel (60 g.) and after elution with a benzene-ether mixture (1:1) afforded 10-[3-oxo-butyl]-18-methyl-19-nor-desA-androstan-5,17-dione.

EXAMPLE 132

100 Mg. of 10[3-oxo-butyl]-18-methyl-19-nor-desA-androstan-5,17-dione produced in Example 131 was dissolved in 5 ml. of toluene. 10 Mg of p-toluenesulfonic acid was added to the toluene mixture and heated under reflux for 3 hours. The reaction mixture was then diluted with benzene, washed free of acid by means of aqueous sodium carbonate solution and dried in vacuo. The residue was purified by chromatography on silica gel (10 g.) and after crystallization from a hexane-ether mixture yielded 13β-ethyl-gon-4-en-3,17-dione, m.p. 156°–158°.

EXAMPLE 133

100 Mg. of 10-[3-oxo-butyl]-18-methyl-19-nor-desA-androstan-5,17-dione produced in Example 131 was dissolved in 5 ml. of tertiary butyl alcohol. This solution was added to a solution of 20 ml. of powdered sodium hydroxide dissolved in 5 ml. of tertiary butyl alcohol. The entire reaction mixture was agitated at 55° under a nitrogen atmosphere for 90 minutes. Dilution with water and extraction using ether furnished a crude oil which was purified by means of chromatography on silica gel (10 g.). Crystallization from hexane-ether yielded 13-β-ethyl-gon-4-en-3,17-dione, m.p. 156°–158°.

EXAMPLE 134

500 Mg. of 10-[3-tertiary-butoxy-butyl]-18-methyl-19-nor-desA-androstan15,17-dione produced in Example 129 was dissolved in 25 ml. of benzene containing a trace of p-toluenesulfonic acid. The reaction mixture was heated under reflux for 2½ hours. The organic phase was then washed free of the acid by means of aqueous sodium bicarbonate solution and the solvents were removed in vacuo. The residue was then dissolved in hexane and upon crystallization yielded 6a,9a-trans-2-methyl-6aβ-ethyl-2,3,4,4b,5,6,8,9,9a,9b,10,11-dodecahydro-cyclopenta[5,6]naphtho-[2,1-b]-pyran-7(6aH)-one melting point 111°–115°.

EXAMPLE 135

6a,9a-Trans-2-methyl-6aβ-ethyl-2,3,4,4b,5,6,8,9,9a,9b,10,11-dodecahydro-cyclopenta[5,6]naphtho[2,1-b]-pyran-7(6aH)-one produced in Example 134 was dissolved in 75 ml. of acetone at room temperature. 35 Ml. of 1 normal sulfuric acid was then added and the reaction mixture was left to stand for 35 minutes. Subsequent dilution with brine, extraction in ether and evaporation of the solvent in vacuo affords crude product, 6a,9a-trans-2-methyl-6aβ-ethyl-7-oxo-perhydrocyclopenta[5,6]naphtho[2,1-b]-pyran-11a-ol. The crude product was then dissolved in hexane and upon crystallization yielded pure hemiketal, 6a,9a-trans-2-methyl-6aβ-ethyl-7-oxo-perhydrocyclopenta[5,6]naphtho[2,1-b]-pyran-11a-ol, melting point 114°–116°.

EXAMPLE 136

500 Mg. of 13β-ethyl-gon-4-en-3,17-dione produced in Example 135, was dissolved in 10 ml. of a benzene-ether solvent mixture (1:1) and added to a solution of 50 ml. of liquid ammonia containing 0.1 ml. of acetone and 0.5 g. of potassium acetylide. The reaction mixture was agitated at the ammonia boiling point for 2 hours and then the ammonia was evaporated at room temperature. The organic materials were extracted with ether and then the solvent was evaporated in vacuo. The residue was purified by chromatography over 50 g. of silica gel and on elution with a benzene-ethyl acetate mixture, afforded 13β-ethyl-17α-ethynyl-17-hydroxy-gon-4-en-3-one.

EXAMPLE 137

3 G. of 6—(S)—[4-(S)(R)—tertiary-butoxy-pentyl]-valerolactone was dissolved in 30 ml. of toluene to which was added 25 ml. of a 25 percent solution of diisobutylaluminumhydride under a nitrogen atmosphere at −70°. The reaction mixture was agitated for 1 hour at this temperature and then poured onto an ice (40 g.) and acetic acid (10 ml.) mixture. The organic material was then extracted with benzene. Removal of the solvent in vacuo yielded the hemiacetal 6—(S)—[-4—(S)(R)—tertiary-butoxy-pentyl]-tetrahydropyran-2-ol.

EXAMPLE 138

Employing apparatus and procedures similar to those described in Examples 121 through 134 inclusive, but substituting the optically active product 6-(S)-[4-(S)(R)-tertiary-butoxypentyl]-tetrahydropyran-2-ol of Example 137 for the racemic form of the same compound of Example 120, there is prepared optically active 13β-ethyl-gon-4-en-3,17-dione. The racemic form of this compound was previously prepared in Example 134. Optically active 13β-ethyl-gon-4-en-3,17-dione can be converted to (+)-norgestrel by following the procedures employed in Example 136.

EXAMPLE 139

(±)-3-(4-Tertiarybutoxypentyl)-6aβ-methyl-1,2,3,4,5,6,6a-hexahydrocyclopenta[f][1]benzopyran-7(8H)-one (±)-2-(2-Diethylaminoethyl)-6-(4-tertiarybutoxypentyl)-tetrahydropyran-2-ol (28 g.) dissolved in xylene (140 ml.) was added to a mixture of 2-methylcyclopentan-1,3-dione (13.7 g.), xylene (280 ml.) and acetic acid (140 ml.) and heated at reflux for 45 min.

The cold reaction mixture was washed with water, aqueous sodium bicarbonate solution and dried over sodium sulphate.

Removal of the solvents and chromatography over alumina (870 g. grade III neutral) yielded the pure above-titled dienol ether (22g.) as an oil.

Calc. C, 76.27; H, 9.89 Found: C, 76.47; H, 10.03

The ultraviolet spectrum showed $\lambda_{max}$ 253 mμ ($\epsilon_{max}$ 17,700).

EXAMPLE 140

(±)-3-(4-Tertiarybutoxypentyl)-6aβ-methyl-1,2,3,5,6,6a,7,8-octahydrocyclopenta[f][1]benzopyran-7β-ol (±)-3-(4-Tertiarybutoxypentyl)-6aβ-methyl-1,2,3,5,6,6a-hexahydrocyclopenta[f][1]benzopyran-7(8H)-one (23.1 g.) dissolved in tetrahydrofuran (464 ml.) was added to a slurry of lithium aluminum hydride (4.6 g.) in tetrahydrofuran (232 ml.) at −10°.

The mixture was then stirred a further 45 min. at 0° and treated with water. The solids were filtered off and the solvents were removed to yield the alcohol (23.1 g.).

A sample of the titled product on crystallization from hexane had m.p. 97°–101°.

Calc. C, 75.78; H, 10.41 Found: C, 76.01; H, 10.28

U.V. $\lambda_{max}$252mμ ($\epsilon_{max}$; 18,700).

EXAMPLE 141

(±)-3-(4-Tertiarybutoxypentyl)-6aβ-methyl-1,2,3,5,6,6a,7,8,9,9a-decahydrocyclopenta[f][1]benzopyran-7β-ol (±)-3-(4-Tertiarybutoxypentyl)-6aβ-methyl-1,2,3,5,6,6a,7,8-octahydrocyclopenta[f][1]benzopyran-7-ol (22.5 g.) was dissolved in toluene (450 ml.) and treated with 5% Pd. on carbon (3.4 g.) and hydrogenated at room temperature and pressure.

After the uptake of one mole of hydrogen, the solids were filtered off and the solvents removed in vacuo to give the above-titled enol ether (23.1 g.) as a pale yellow oil.

A sample on chromatography over alumina (Neutral; grade III) yielded analytical material showing no strong u.v. adsorbtion.

Calc. C, 75.38; H, 10.93 Found: C, 75.15; H, 10.93

I.R. (chloroform) showed bands at 3625 (OH) and 1,680 cm$^{-1}$ (enol ether).

EXAMPLE 142

(±)-3-(4-Tertiarybutoxypentyl)-6aβ-methyl-perhydrocyclopenta[f][1]benzopyran-4a,7β-diol (±)-3-(4-Tertiarybutoxypentyl)-6aβ-methyl-1,2,3,5,6,6a,7,8,9,9a-decahydrocyclopenta[f][1]benzopyran-7β-ol (22.1 g.) in acetone (220 ml.) was treated with aqueous sulphuric acid (1N; 110 ml.) and left at room temperature for 3 hrs. Most of the acetone was removed in vacuo at 35° and the organic materials were isolated with ether.

Removal of the ether gave the above-titled hemiketal (21.5 g. as a glass).

A sample on chromatography over alumina (Neutral grade III) yielded material showing bands in the infrared at 3,625 cm$^{-1}$ (OH) and 1,200 cm$^{-1}$ (O-t-butyl) and no enol ether bands.

EXAMPLE 143

(±)-Trans-4-(3-oxo-7-tertiarybutoxy-octyl)-7aβ-methylperhydroindan-1,5-dione (±)-3-(4-Tertiarybutoxypentyl)-6aβ-methyl-perhydrocyclopenta [f][1]benzopyran-4a,7β-diol (17.4 g.) dissolved in acetone (700 ml.) was cooled to 15° and treated over 20 mins. with a solution of chromium trioxide (12.7 g.) dissolved in aqueous sulphuric acid (63.5 ml.)

After stirring a further 2 hrs. at room temperature, the products were isolated with benzene to yield the above-titled triketone (15.4 g.) as an oil.

A sample on distillation (molecules still B.P. 195°–205° at .01 mm.) showed bands in the infra red spectrum at 1735 (cyclopentanone),1708 (cyclohexanone and alkyl ketone) and 1200 cm$^{-1}$ (O-t-butyl).

Calc. C, 72.49; H, 9.95 Found: C, 72.21; H, 10.00

EXAMPLE 144

(±)-6-(3-Tertiarybutoxybutyl)-3aβ-methyl-4,5,8,,9,9a,9b-hexahydro-1H-benz[e]inden-3,7-(2H,3aH)-dione (±)-Trans-4-(3-oxo-7-tertiarybutoxy-octyl)-7aβ-methyl perhydroindan-1,5-dione (13.8 g.) dissolved in tertiarybutyl alcohol (38 ml.) was added to a solution of sodium hydroxide (544 mg.) in tertiary butyl alcohol (136 ml.) under nitrogen.

The mixture was stirred at 55° for 1 hr., treated with acetic acid (1 ml.) and the organic materials were isolated with benzene.

Removal of the benzene in vacuo gave the above-titled tricyclic material (11.9 g.) as a pale yellow oil.

The product showed strong absorbtion in the u.v. at $\lambda_{max}$ 247 m$\mu$ ($\epsilon_{max}$; 13,000) and had the characteristic bands in the infrared spectrum at 1,730 (cyclopentanone) and 1,660 and 1,600 cm$^{-1}$ (cyclohexenone).

EXAMPLE 145

(±)-2-Methyl-6aβ-methyl-2,3,4,6,8,9,9a,9b,10,11-decahydrocyclopenta[5,6]naphtho[2,1-b]pyran-7(6aH)-one (±)-6-(3-Tertiarybutoxybutyl)-3aβ-methyl-4,5,8,9.9a,9b-hexahydro-1H-benz[e]inden-3,7(2H,3aH)dione (10 g.) was dissolved in benzene (300 ml.) containing p-tolune sulphonic acid (500 mg.) and heated at reflux for 3½ hrs.

The cold reaction mixture was washed with aqueous sodium bicarbonate solution and the solvents were removed in vacuo to yield the above-titled dienol ether (8 g.) as an oil showing bands in the infra red spectrum at 1,735 (cyclopentanone) and 1,645 cm$^{-1}$ (dienol ether).

The u.v. spectrum showed $\lambda_{max}$ 249 m$\mu$ ($\epsilon_{max}$ 17,500).

EXAMPLE 146

(±)-2-Methyl-6aβ-methyl-2,3,4,4b,5,6,8,9,9a,9b,10,11-dodecahydrocyclopenta[5,6]naphtho[2,1-b]pyran-7(6aH)one (±)-2-Methyl-6aβ-methyl-2,3,4,6,8,9,9a,9b,10,11-decahydrocyclopenta[5,6]naphtho[2,1-b]pyran-7(6aH)-one (8 g.) was dissolved in toluene (200 ml.) containing triethylamine (1.5 ml.) and 5% Pd on charcoal (1.5 g.) and hydrogenated at room temperature and pressure until one mole of hydrogen had been consumed.

The solids were filtered off and the solvents removed in vacuo to yield the above-titled enol ether as an oil. Chromatography over alumina (Neutral; Grade III) yielded pure product (6 g.).

Calc. C, 78.98; H, 9.42 Found: C, 78.79; H, 9.55

Infra red spectrum showed bands at 1,740 (cyclopentanone) and 1680 cm$^{-1}$ (enol ether).

The same material was also prepared as follows:

(±)-6-(3-tertiarybutyoxybutyl)-3aβ-methyl-4,5,8,9,9a,9b-hexahydro-1H-benz[e]inden-3,7-(2H,3aH)-dione (1.5 g.) was dissolved in ethanol (25 ml.) containing triethylamine (.15 ml.) and 5% P/c. (200 mg.) and hydrogenated at room temperature and pressure until no more hydrogen was consumed.

The solids were filtered off and the solvents were removed in vacuo to yield racemic 6-(3)tertiarybutoxybutyl)-3aβ-methylperhydro-benz[e]indane-3,7-dione as an oil.

This material showing infra red bands at 1,735, 1,705 and 1,200 cm$^{-1}$ was dissolved in benzene (25 ml.) containing p-toluene sulphonic acid (100 mg.) and heated at reflux for 4 hrs.

After washing the cold reaction mixture with brine and removal of the solvents in vacuo, the residue was filtered through a column of alumina (Neutral; grade III) to yield the above-titled pure enol ether.

EXAMPLE 147

(±)-2-Methyl-6aβ-methyl-2,3,4,4b,5,6,8,9,9a,9b,10,11-dodecahydrocyclopenta[5,6]naphtho[2,1-b]pyran-7β-ol The enol ether 2-methyl-6aβ-methyl-2,3,4,4b,5,6,8,9,9a,9b, 10,11-dodecahydrocyclopenta[5,6]naphtho[2,1-b]pyran-7(6aH)one (3 g.) in ether (20 ml.) was added to a slurry of lithium aluminum hydride (600 mg.) in ether (25 ml.) at 10°.

After stirring a further one hour at room temperature, water was added and the solids were filtered off. Removal of the solvents yielded (3 g.) as a glass showing bands in the infrared at 3,600 (OH) and 1,680 cm$^{-1}$ (enol ether).

EXAMPLE 148

An ice-cold solution of 39.1 g. of (-)-9-oxo-5(S)-hydroxydecanoic acid lactone in pyridine (240 ml; anhydrous) was treated with an ice-cold solution of methoxyamine hydrochloride (35.6 g.) in pyridine (200 ml) at 10°C. under stirring. After stirring at room temperature for 30 min. the reaction mixture was treated with triethylamine (61 ml) at 0°C. during 15 min. The precipitated triethylamine hydrochloride was filtered off and washed several times with benzene. The filtrates were washed with brine and then dried over anhydrous sodium sulfate. Filtration and solvent removal afforded crude 9-methoxyimino-5(S)-hydroxydecanoic acid lactone as a yellow oil (44.4 g.). A sample was distilled (bp 110°–120°C., 0.05 mm Hg; short path) to give analytically pure product which had a $[\alpha]_D^{25}$ −44.56° (c=1.0817 in CHCl$_3$).

Calcd for C$_{11}$H$_{19}$O$_3$N: C, 61.94; H, 8.98; N, 6.57. Found: C, 62.18; H, 8.83; N, 6.52.

Ir (chloroform) showed an absorption at 1740 cm$^{-1}$ (lactone).

EXAMPLE 149

A solution of crude 9-methoxyimino-5-(S)-hydroxydecanoic acid lactone (144.4 g.) in tetrahydrofuran (850 ml; dry) was cooled under nitrogen in a dry ice-acetone bath to −60°C. A 2.24 molar vinyl magnesium-chloride in tetrahydrofuran solution (159 ml; 70% excess) was added at such a rate that the temperature remained at −50° to −55°C. during 10 min. The reaction mixture was then stirred for an additional 20 min. at −55 to −60°C. after which it was cooled to −70°C. and at this temperature carefully hydrolyzed with methanol (24 ml). The resulting mixture was poured into a mixture of saturated ammonium chloride solution (250 ml), ether (700 ml) and ice (100 g.). The aqueous phase was extracted several times with ether. The ethers were washed with brine and then dried over anhydrous sodium sulfate to give a solution containing 6(S)—(4-methoxyiminopentyl)-2-vinyl-tetrahydropyran-2-ol and its tautomer. Diethylamine (85 ml) was added to this ether solution and the mixture was allowed to stand at room temperature for 1 hr. Filtration and solvent removal affored crude 2(S)-diethylaminoethyl6(S)-(4-methoxyiminopentyl)-tetrohydropyran-2-ol (62.5 g.). This material was dissolved in acetone (850 ml) and treated with 2N sulfuric acid (610 ml) at 0°C. After the reaction mixture was allowed to stand at room temperature for 25 hr, it was concentrated to a volume of 650 ml at 30°C. in vacuo and then extracted with ether. The ether was washed with brine. The aqueous phase was treated with 10N sodium hydroxide solution (155 ml) at 0°C. The resulting mixture was extracted with ether, the ether was washed with brine and then dried over anhydrous sodium sulfate. Filtration and solvent removal afforded pure 2(S)-diethylaminoethyl-6(S)-(4-oxopentyl)-tetrahydropyran-2-ol as a yellow oil (45.5 g.). A sample was chromatographed on aluminum oxide (grade III). Elution with benzene-ether 9:1, 4:1 and 2:1 afforded an analytically pure sample of product as a colorless oil; $[\alpha]_D^{25}$ −39.91° (C=1.3832 in benzene).

Calcd for C$_{16}$H$_{31}$O$_3$N: C, 67.33; H, 10.94; N, 4.91 Found: C, 67.38; H, 10.66; N, 4.88

Ir (chloroform): shoulder at 3,100 cm$^{-1}$ (hydroxyl; strongly bonded); carbonyl at 1725 cm$^{-1}$.

EXAMPLE 150

A mixture of 2-methylcyclopentane-1,3-dione (22 g.), toluene (700 ml) and acetic acid (250 ml) was carefully degassed, placed under nitrogen and heated to 110°C. in an apparatus which was fitted with a Dean-Stark trap. To this mixture was added, with stirring and during 10 min., a solution of 2(S)-diethylaminoethyl6(S)-(4-oxopentyl)-tetrahydropyran-2-ol (45.0 g.) in toluene (200 ml). The resulting reaction mixture was stirred at 110°C. (bath) for 30 min. (Slight reflux but not enough for water to distill into Dean-Stark trap). The temperature was then raised to 130°C. for 1 hr. The cooled mixture was washed with water, saturated sodium bicarbonate solution and brine. The aqueous phases were re-extracted with benzene and the combined benzene dried over anhydrous sodium sulfate. Filtration and solvent removal afforded crude 3(S)-(4-oxopentyl)-6a$\beta$(S)-methyl-1,2,3,5,6,6a-hexahydrocyclopenta[f][1]benzopyran-7(8H)-one (44.0 g. crystals). This material was dissolved in methanol (300 ml) and treated with water (135 ml) under slow stirring. After 30 min. at room temperature more water (50 ml) was added. The crystals were filtered off after 3 ½ hr at room temperature, washed with a cold mixture of methanol-water 1:1 (50 ml) and then dried at room temperature over phosphorus pentoxide to afford pure product (24.4 g.) mp 70°–73°C., $[\alpha]_D^{25}$ −159.7° (c=2.03 in CHCl$_3$). The mother liquor of the crystallization was treated with water (40 ml) over a period of 1 hr. After standing at room temperature for 3 ½ hr the crystals were filtered off, washed with a cold mixture of methanol-water 1:1 (25 ml) and then dried over phosphoruspentoxide to give additional product (4.32 g.) $[\alpha]_D^{25}$ −150.3° (c= 1.05 in CHCl$_3$). This material was recrystallized as described above to give a second crop of pure product (3.2 g.) mp 74°–75°C., $[\alpha]_D^{25}$ −162.1° (c=1.21 in CHCl$_3$). Thus, a total of 27.6 g. of pure dienol ether was isolated. A sample was recrystallized twice from methanol-water to give analytically pure product as colorless needles, mp 74°–76°C., $[\alpha]_D^{25}$ −164.26° (c=0.9832 in CHCl$_3$).

Calcd for C$_{18}$H$_{24}$O$_3$: C, 74.96; H, 8.39 Found: C, 74.76; H, 8.38

Uv-max (ethanol) at 252 m$\mu$,$\epsilon$ 18750.

Ir (chloroform) showed absorptions at 1,642 cm$^{-1}$ (dienol ether), 1712 cm$^{-1}$ (4-oxopentyl) and 1740 cm$^{-1}$ (cyclopentanone).

EXAMPLE 151

A solution of 3(S)-(4-oxopentyl)-6a$\beta$(S)-methyl-1,2,3,5,6,6a-hexahydrocyclopenta[hexahydrocyclopenta[f][1]benzopyran-7(8H)-one (8.24 g.) in tetrahydrofuran (170 ml; dried over aluminum oxide grade I) was added at 0°–5°C. within 10 min. to a mixture of lithium aluminum hydride (4.35 g.) in tetrahydrofuran (400 ml), with stirring and under nitrogen. The reaction mixture was stirred for an additional 30 min. at room temperature and then worked up by careful addition of saturated aqueous sodium sulfate solution, filtration, and continuation of the filtrate. Thus, crystalline product 3(S)-(4-hydroxypentyl)-6a$\beta$(S)-methyl-1,2,3,5,6,6a,7,8-octahydrocyclopenta[f][1-]benzopyran-7$\beta$-ol was obtained (8.9 g.; yellow-tan crystals), $[\alpha]_D^{25}$ −164.1° (c=0.98 chloroform). A sample was recrystallized twice from ether isopropyl ether to afford analytically pure product as beige-colored crystals, mp 95°–102°C., $[\alpha]_D^{25}$ −180.44° (c=1.0142 in chloroform).

Calcd for C$_{18}$H$_{28}$O$_3$: C, 73.94; H, 9.66 Found: C, 73.66; H, 9.56

Uv-max (ethanol) at 252 m$\mu$, $\epsilon$17750.

Ir(CHCl$_3$) showed absorptions at 1,645 cm$^{-1}$ (dienolether) and 3,620 cm$^{-1}$ (hydroxyl).

EXAMPLE 152

A solution of 3(S)-(4-hydroxypentyl)-6aβ(S)-methyl-1,2,3,5,6,6a,7,8-octahydrocyclopenta[f][1]benzopyran-7β-ol (8.8 g.) in tetrahydrofuran (270 ml; dried over aluminum oxide grade I) was hydrogenated under normal conditions using 1.2 g. of 5 percent palladium-on-charcoal catalyst. The uptake (710 ml) of hydrogen stopped after about 3 ½ hr. The catalyst was filtered off and washed with tetrahydrofuran. Solvent removal gave crude 6a,9a-trans-3(s)-(4-hydroxypentyl)-6aβ(S)-methyl-1,2,3,5,6,6a,7,8,9,9a-decahydrocyclopenta[f][1]benzopyran-7β-ol as an oil (9.0 g.).

EXAMPLE 153

A solution of crude 6a,9a-trans-3(S)-(4-hydroxypentyl)16aβ(S)-methyl-1,2,3,5,6,6a,7,8,9,9a-decahydrocyclopenta[f][1]benzopyran-7β-ol (9.0 g.) in pyridine (80 ml) was treated with acetic anhydride (40 ml) at 0°C. with stirring. The reaction mixture was allowed to stand at room temperature for 18 hr. Then it was worked up by careful addition of methanol (40 ml) at 0°C. The resulting mixture was evaporated and the residue dissolved in benzene and and washed with saturated aqueous sodium bicarbonate and brine and then dried over anhydrous sodium sulfate. Filtration and solvent removal afforded crude 6a,9a-trans-7β-acetoxy-3(S)-(4-acetoxypentyl)-6aβ (S)-methyl-1,2,3,5,6,6a,7,8,9,9a-decahydrocyclopenta[f][1] benzopyran (10.0 g.) as an oil.

EXAMPLE 154

A mixture of crude 6a,9a-trans-7β-acetoxy-3(S)-(4-acetoxypentyl)-6aβ (S)-methyl-1,2,3,5,6,6a,7,8,9,9a-decahydrocyclopenta[f][1]-benzopyran (10.0 g.), acetone (170 ml) and 1 N sulfuric acid (50 ml) was allowed to stand at room temperature for 2 ½ hr. The reaction mixture was then cooled to 5°C. and treated with freshly prepared Jones' Reagent (14.2 ml). After addition, the mixture was stirred for 2 ½ hr. at room temperature. Under cooling sodium bisulfite was added until the color was green then the solution was adjusted to pH 6–7 with 10% sodium carbonate solution. Most of the acetone was evaporated at 35°C. in vacuo and the resulting aqueous solution was extracted with benzene, the benzene layer was washed with saturated sodium bicarbonate and brine and then dried over anhydrous sodium sulfate. Filtration and solvent removal afforded crude 3a,7a-trans-1β-acetoxy-4-[7'-acetoxy-3'oxo-octyl]-7aβ-methyl-perhydroindan-5-one (9.45 g.) as an oil.

EXAMPLE 155

A mixture of crude 3a,7a-trans-1β-acetoxy-4-[7'-acetoxy-3'-oxo-octyl]-7aβ-methyl-perhydroindan-5-one (8.7 g.), methanol (87 ml) and potassium hydroxide (2.6 g.) was refluxed for 1 ½ hr. under $N_2$. Water (87 ml) was then added and the resulting mixture was saturated with sodium chloride and then extracted with chloroform. The chloroform was washed with brine and then dried over anhydrous sodium sulfate. Filtration and solvent removal afforded crude 17β-hydroxy-10-[3-hydroxybutyl]-19-nor-des A-androst-9-en-5-one (7.0 g.) as an oil.

EXAMPLE 156

A mixture of crude 17β-hydroxy-10-[3-hydroxybutyl]-19-nor-des A-androst-9-en-5-one (7.0 g.), benzene (140 ml) and p-toluenesulfonic acid (200 mg) was stirred at room temperature for 2 hr. The reaction mixture was then washed with water, saturated sodium bicarbonate and brine and then dried over anhydrous sodium sulfate. Filtration and solvent removal afforded crude 2-(S)(R),6aβ(S)-dimethyl-2,3,4,6,8,9,9a,9b,10,11-decahydrocyclopenta[5,6]naphtho[2,1-b]pyran-7β-ol (5.6 g.) as an oil. This crude product was chromatographed on silica gel (280 g.). Elution with hexane-ether 2:1 and 1:1 afforded pure crystalline product (3.66 g.), mp 60°–71°C., $[\alpha]_D^{25}$ −141.3° (c=1.42 in $CHCl_3$).

Calcd for $C_{18}H_{26}O_2$: C, 78.76; H, 9.56 (274.406) Found: C, 78.58; H, 9.95

Uv max (ethanol) at 248 mμ,∈= 16,000.

Ir (chloroform) showed absorptions at 1,640 $cm^{-1}$ (dienolether) and 3,610 $cm^{-1}$ (hydroxyl).

EXAMPLE 157

A solution of 2-(S)(R),6aβ(S)-dimethyl-2,3,4,6,8,9,9a,9b,10,11-decahydrocyclopenta[5,6]naphtho[2,1-b]pyran-7β-ol (3.75 g.) in toluene (40 ml.) and triethylamine (0.37 ml.) was hydrogenated under normal conditions using 5% palladium on charcoal catalyst (550 mg.). The uptake (350 ml.) of hydrogen stopped after about 2 hr. The catalyst was filtered off and washed with toluene. Solvent removal gave crude 2-(S)(R),6aβ(S)-dimethyl-2,3,4,4b,5,6,8,9,9a,9b,10,11-dodecahydrocyclopenta[5,6]naphtho[2,1-b]pyran7β-ol as an oil (3.9 g.).

EXAMPLE 158

A total of 2.5 g. of crude 2-(S)(R),6a(S)-dimethyl-2,3,4,4b,5,6,8,9,9a,9b,10,11-dodecahydrocyclopenta[5,6]naphtho[2,1-b]-pyran-7β-ol was dissolved in 175 ml. of acetone and treated with 75 ml. of 1N aqueous sulfuric acid. After standing at room temperature for 35 minutes the solution was diluted with brine. Extraction with ether, separation of the organic phase, drying over anhydrous sodium sulfate and evaporation of the solvent yielded crude optically active 2-(S)(R),6aβ(S)-dimethyl-perhydrocyclopenta[5,6]naphtho[2,1-b]pyran-7β,11a-diol.

EXAMPLE 159

A total of 373 mg. of crude 2-(S)(R,6aβ(S)-dimethylperhydrocyclopenta[5,6]naphtho[2,1-b]pyran-7β,11a-diol in 15 ml. of acetone was treated with a mixture of 634 mg. of chromic acid in 3.2 ml. of 6N sulfuric acid over a period of 10 minutes with stirring and ice-cooling (20°C). After addition the mixture was stirred for another hour at room temperature. The usual workup gave 307 mg. of crude optically active 10-[3-oxobutyl]-19-nor-desA-androstan-5,17-dione. This material can be purified by chromatography on silica gel (30 g.). Elution with benzene-ether (2:1) followed by benzene-ether (1:1) afforded the desired product in the latter fractions (yield 96.7 mg. after evaporation).

EXAMPLE 160

A mixture of 96.7 mg. of optically active 10-[3-oxobutyl]-19-nor-desA-androstan-5,17-dione, 4 ml. of toluene and 9.7 mg. of p-toluenesulfonic acid was refluxed for 3 hr. The reaction mixture was then diluted with benzene, washed free of acid by means of aqueous sodium carbonate solution and the organic phase was dried over anhydrous sodium sulfate. After filtration and solvent removal crude (+)-19-nor-androst-4-en-3,17-dione was obtained. This material was triturated with a mixture of isopropyl ether and hexane, cooled to 0°C. and then filtered off to give beige crystals of product; m.p. 167°–170°C., $[\alpha]_D^{25}$ +127.1° (c = 1.0 CHCl$_3$). The mother liquor from the crystallization was evaporated and the residue was chromatographed on 4 g. of silica gel. Elution with benzene-ethyl acetate 4:1 and 2:1 gave, after trituration as above, additional product; m.p. 166°–170°C, $[\alpha]_D^{25}$ +124.2° (c = 0.5 CHCl$_3$). The combined crops were recrystallized twice from methanol-water to give white crystals; m.p. 168°–171°C, $[\alpha]_D^{25}$ +139.2° (c = 1.0 in CHCl$_3$). An analytical sample of (+)-19-nor-androst-4-en-3,17-dione was obtained by two recrystallizations from methanol-water and one from acetone-hexane; m.p. 169°–171°C, $[\alpha]_D^{25}$ +141.65°(c = 1.0145 in CHCl$_3$).

Calcd. for $C_{18}H_{24}O_2$: C, 79.48; H, 8.89 Found: C, 79.61; H, 8.63.

Uv$_{max}$ (ethanol) at 240 m$\mu$,$\epsilon$=17,350.

I claim:

1. A compound of the formula

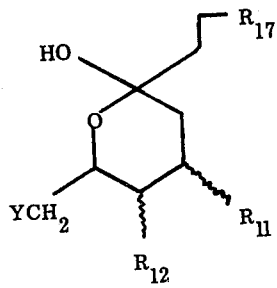

wherein Y is hydrogen; an alkyl group of from 1 to 6 carbons or a group of the formula $R_5CH_2C(R_3,R_4)CH(R_{14})CH(R_{15})-$ wherein $R_3$, when taken alone, is hydroxy or a conventional hydrolyzable ether or ester group convertible to a hydroxy group by hydrolysis, $R_4$, when taken alone is hydrogen, and $R_3$ and $R_4$, when taken together, are oxo or a conventional hydrolyzable ketal group convertible to an oxo moiety by hydrolysis; $R_5$, $R_{11}$, $R_{12}$, $R_{14}$ and $R_{15}$ are each independently hydrogen or lower alkyl; and $R_{17}$ is lower hydrocarbylamino or di(lower hydrocarbyl)amino.

2. The compounds of claim 1 wherein $R_3$ and $R_4$ taken together are oxo.

3. The compounds of claim 1 wherein $R_3$ and $R_4$ taken together represent an alkylenedioxy group having 1 to 4 carbon atoms.

4. The compounds of claim 1 wherein $R_3$ is t-butoxy and $R_4$ is hydrogen.

5. The compounds of claim 1 wherein $R_{17}$ is diethylamino.

6. The compounds of claim 1 wherein $R_{17}$ is an optically active amine radical or a salt thereof.

7. The compounds of claim 6 wherein $R_{17}$ is an enantiomer of a phenethylamine radical.

8. The compound of claim 5 which is 2(S)-diethylaminoethyl-6(S)-(4-oxopentyl)-tetrahydropyran-2-ol.

* * * * *